US012758571B2

(12) United States Patent
Shuldiner et al.

(10) Patent No.: US 12,758,571 B2
(45) Date of Patent: Oct. 13, 2026

(54) TREATMENT OF INCREASED LIPID LEVELS WITH STEROL REGULATORY ELEMENT BINDING TRANSCRIPTION FACTOR 1 (SREBF1) INHIBITORS

(71) Applicants: Regeneron Pharmaceuticals, Inc., Tarrytown, NY (US); University of Maryland, Baltimore, Baltimore, MD (US)

(72) Inventors: Alan Shuldiner, Tarrytown, NY (US); Nehal Gosalia, Tarrytown, NY (US); Cristopher Van Hout, Tarrytown, NY (US); Da-Wei Gong, Baltimore, MD (US); James A. Perry, Baltimore, MD (US)

(73) Assignees: Regeneron Pharmaceuticals, Inc., Tarrytown, NY (US); University of Maryland, Baltimore, Baltimore, MD (US)

( * ) Notice: Subject to any disclaimer, the term of this patent is extended or adjusted under 35 U.S.C. 154(b) by 124 days.

(21) Appl. No.: 18/047,026

(22) Filed: Oct. 17, 2022

(65) Prior Publication Data

US 2023/0263821 A1 Aug. 24, 2023

Related U.S. Application Data

(63) Continuation of application No. 16/823,634, filed on Mar. 19, 2020, now Pat. No. 11,504,390.

(60) Provisional application No. 62/879,138, filed on Jul. 26, 2019, provisional application No. 62/820,893, filed on Mar. 20, 2019.

(51) Int. Cl.
*A61K 31/7105* (2006.01)
*C12N 9/22* (2006.01)
*C12Q 1/6827* (2018.01)
*C12Q 1/6853* (2018.01)

(52) U.S. Cl.
CPC ............ *A61K 31/7105* (2013.01); *C12N 9/22* (2013.01); *C12Q 1/6827* (2013.01); *C12Q 1/6853* (2013.01); *C12N 2310/11* (2013.01); *C12N 2310/14* (2013.01); *C12N 2310/20* (2017.05); *C12N 2310/531* (2013.01)

(58) Field of Classification Search
CPC ............ C12N 2310/11; C12N 2310/14; C12N 2310/531; C12N 15/113; C12Q 1/6883
See application file for complete search history.

(56) References Cited

U.S. PATENT DOCUMENTS 6,602,710 B1 8/2003 Chang et al.
6,673,555 B1 1/2004 Grand-Perret et al.
7,919,613 B2 4/2011 Soutschek et al.
8,383,805 B2 2/2013 Soutschek et al.
9,102,940 B2 8/2015 Soutschek et al.
2003/0224347 A1 12/2003 Grand-Perret et al.
2003/0224348 A1 12/2003 Grand-Perret et al.
2005/0014177 A1 1/2005 Ranade et al.
2008/0249040 A1* 10/2008 McSwiggen ............ C12P 19/34 536/23.1
2013/0184324 A1 7/2013 Fitzgerald et al.
2016/0068840 A1 3/2016 Soutschek et al.
2016/0312216 A1 10/2016 Fitzgerald et al.
2017/0002421 A1 1/2017 Sgroi et al.
2021/0095277 A1 4/2021 Lindholm et al.

FOREIGN PATENT DOCUMENTS

WO 2003008625 1/2003
WO 2008011467 1/2008
WO 2008036638 3/2008
WO 2016141159 9/2016
WO 2017191165 5/2017
WO 2017100542 6/2017
WO 2017107545 6/2017
WO 2019148125 8/2019
WO 2019186558 10/2019

OTHER PUBLICATIONS

Laaksonen, Reijo, et al. "Genetic variant of the SREBF-1 gene is significantly related to cholesterol synthesis in man." Atherosclerosis 185.1 (2006)).*
Miranzadeh-Mahabadi et al. ("Association study between metabolic syndrome and rs8066560 polymorphism in the promoter region of sterol regulatory element-binding transcription factor 1 gene in Iranian children and adolescents." International Journal of Preventive Medicine 7.1 (2016): 41).*
Peng et al. ("Lack of association between SREBF-1c gene polymorphisms and risk of non-alcoholic fatty liver disease in a Chinese Han population." Scientific reports 6.1 (2016): 32110).*
Soyal et al. ("Targeting SREBPs for treatment of the metabolic syndrome." Trends in pharmacological sciences 36.6 (2015): 406-416).*
Fon Tacer et al. ("Nonalcoholic Fatty liver disease: focus on lipoprotein and lipid deregulation." Journal of lipids 2011.1 (2011): 783976).*
Miyagishi et al. (Antisense and Nucleic Acid Drug Development, 2003, 13:1-7).*
Vickers et al. (The Journal of Biological Chemistry, 2003, 278:7108-7118).*
Dean et al. (Oncogene, 2003, 22:9087-9096).*
Eberle et al., "SREBF-1 Gene Polymorphisms Are Associated With Obesity and Type 2 Diabetes in French Obese and Diabetic Cohorts", Diabetes, 2004, 53(8), pp. 2153-2157.

(Continued)

*Primary Examiner* — Kimberly Chong
(74) *Attorney, Agent, or Firm* — Armstrong Teasdale LLP

(57) ABSTRACT

The present disclosure provides methods of treating subjects having increased lipid levels, methods of identifying subjects having an increased risk of developing an increased lipid level, methods of detecting human Sterol Regulatory Element Binding Transcription Factor 1 (SREBF1) variant nucleic acid molecules and variant polypeptides, and SREBF1 variant nucleic acid molecules and variant polypeptides.

6 Claims, 6 Drawing Sheets

Specification includes a Sequence Listing.

(56) References Cited

OTHER PUBLICATIONS

Jensen et al., "Dose-dependent effects of siRNA-mediated inhibition of SCAP on PCSK9, LDLR, and plasma lipids in mouse and rhesus monkey", Journal of Lipid Research, 2016, 57(12), pp. 2150-2162.
Laaksonen et al., "Genetic variant of the SREBF-1 gene is significantly related to cholesterol synthesis in man", Atherosclerosis, 2006, 185(1), pp. 206-209.
Li et al., "SCAP knockdown in vascular smooth muscle cells alleviates atherosclerosis plaque formation via up-regulating autophagy in ApoE -/- mice", The FASEB Journal, 2019, 33(3), pp. 3437-3450.
Moon et al., "The Scap/SREBP Pathway Is Essential for Developing Diabetic Fatty Liver and Carbohydrate-Induced Hypertriglyceridemia in Animals", Cell Metabolism, 2011, 15(2), pp. 240-246.
Murphy et al., "siRNA-mediated inhibition of SREBP cleavage-activating protein reduces dyslipidemia in spontaneously dysmetabolic rhesus monkeys", Metabolism Clinical and Experimental, 2017, 71, pp. 202-212.
Salek et al., "Effects of SREBF-1a and SCAP polymorphisms of plasma levels of lipids, severity, progression and regression of coronary atherosclerosis and response to therapy with fluvastatin", Journal of Molecular Medicine, 2002, 80(11) pp. 737-744.
Snpdev, "Referecne SNP (refSNP) Cluster Report: rs746678809", 2018, http://www.ncbi.nlm.nih.gov/projects/SNP/snp_ref.cgi?do_not_redirect&rs=rs746678809.
Sun et al., "SCAP gene polymorphisms decrease the risk of non-alcoholic fatty liver disease in females with metabolic syndrome", Journal of Genetics, 2013, 92, pp. 565-570.
Yahagi et al., "Absence of sterol regulatory element-binding protein-1 (SREBP-1) ameliorates fatty livers but not obesity of insulin resistance in Lep(ob)/Lep(ob) mice", The Journal of Biological Chemistry, 2002, 277(22), pp. 19353-19357.
International Search Report and Written Opinion for PCT Application PCT/US2020/023532.
International Search Report and Written Opinion for PCT Application PCT/US2020/023564.
Non-Final Office Action dated Aug. 12, 2021 in related U.S. Appl. No. 16/823,832.
Notice of Allowance dated Jan. 18, 2022 in related U.S. Appl. No. 16/823,832.
Talebi et al., "Sustained SREBP-1-dependent lipogenesis as a key mediator of resistance to BRAF-targeted therapy". Nature Communications, 2018, 9.1, pp. 1-11.
Liu et al., "Delivery strategies of the CRISPR-Cas9 gene-editing system for therapeutic applications", Journal of Controlled Release, 2017, 266, pp. 17-26.
Horie et al., "MicroRNA-33b knock-in mice for an intron of sterol regulatory element-binding factor 1 (srebf1) exhibit reduced HDL-C in vivo", Sci Rep, 2014, 4(5312), pp. 1-7.
Enjoji et al., "Nutrition and nonalcoholic fatty liver disease: the significance of cholesterol", International Journal of Hepatology, 2012, pp. 1-6.
Lee et al., "The cellular function of SCAP in metabolic signaling", Exp Mol Med, 2020, 52, pp. 724-729.
Fitzgerald et al., "A Highly Durable RNAi Therapeutic Inhibitor of PCSK9", The New England Journal of Medicine, 2017, 376(1), pp. 41-51.
Kamisuki et al., "A Small Molecule That Blocks Fat Synthesis By Inhibiting the Activation of SREBP", Chemistry and Biology, 2009, 16, pp. 882-892.
Hawkins et al., "Pharmacologic Inhibition of Site 1 Protease Activity Inhibits Sterol Regulatory Element-Binding Protein Processing and Reduces Lipogenic Enzyme Gene Expression and Lipid Synthesis in Cultured Cells and Experimental Animals", Journal of Pharmacology and Experimental Therapeutics, 2008, 326, pp. 801-808.
Fiegenbaum et al., "Determinants of variable response to simvastatin treatment: the role of common variants of SCAP, SREBFa and SREBF-2 genes", The Pharmacogenomics Journal, 2005, 5, pp. 359-364.
NCBI Database, "Submitted SNP(ss) Details: ss2792494710", dbSNP Short Genetic Variations, 2017, http://www.ncbi.nlm.nih.gov/projects/SNP/snp_ss.cgi?subsnp_id=ss2792494710>, pp. 1-2.

* cited by examiner

A)

B)

C)

SEQUENCE LISTING

```
Sequence total quantity: 41
SEQ ID NO: 1            moltype = DNA  length = 24930
FEATURE                 Location/Qualifiers
source                  1..24930
                        mol_type = genomic DNA
                        organism = Homo sapiens
SEQUENCE: 1
gcggccgggg gaacccagtt tccgaggaac ttttcgccgg cgccgggccg cctctgaggc  60
cagggcagga cacgaacgcg cggagcggcg gcggcgactg agagccgggg ccgcggcggc  120
gctccctagg aagggccgta cgaggcggcg ggcccggcgg gcctcccgga ggaggcggct  180
gcgccatgga cgagccaccc ttcagcgagg cggctttgga gcaggcgctg ggcgagccgt  240
gcgatctgga cgcggcgctg ctgaccgaca tcgaaggtgc gtcagggcgg gcagggcttg  300
aagctgcgcc gggtggcgcg agtagggggc gcgcaggtgt ctccctggcc tttgtctccc  360
ccacgggcgc cagctccgtg ctgtgctcgc gcgggacttc ccggtgtctc tgagctcggt  420
gtcccgagcc tcaccgagcc tccctggttc ccgcgctagc gtctcgggcc gcgcgcttgt  480
gggtgagggc tcctgggccg ggccggggtc ccttggcggc tccgggccgg gacacgtgcg  540
cctctacgcg tcccaggccg ggtgccgccc gaccggtgac tctccagccc tgtgatggcc  600
acggctgaag ctggggaccc aggcgtcgcc gaagctccgc cccagcccca gccgtgacgt  660
aattgcgagg ttactcacgg tcattccctc cggcccgaga gttcagctcg gcgtcggagc  720
tcttgcgcat gcgcatgggc gctgcctcgc gcccttcccc cgcctcgtgt cgggttctcc  780
cggtctgcga cgggcacagc ctccgcactc attcactgac atccaccgaa tgccaggccc  840
cgtcttaggc accgagggtt tacagacaga cctgggtacc ccctctttta gggaacacaa  900
aaatctcccg ggaaaccaaa cgggtattta gttgtacctt gggtggagcg aggctggggg  960
agggcaggga tgtggctact ttgggtagag cggtcaggga cttctaagct gagacctgag  1020
ggtcaccccc aggaccagca aggaaagatg ttttccaggc cacggcaagg gaagggcaaa  1080
ggcctcgagg cagggcctaa gtgtgaggag ttagaggctt gcaaaggagt gaggtcaggg  1140
aggaggagga cgcaaaccga cttggtcggc cagggaaagg gcggagcaga acagtggcac  1200
cggcttccat ctttggagca tcaccctggc tgtgatgaga aggggtttgg ggccaatggt  1260
ggcaccaagt gccaattagg aggcccgttg cttccatttt gtagatagag caaacggaag  1320
cccctagcaa attgcctgca tggtttctgt gcaggagttt tagcagcact agctaagttg  1380
cacttggttg atgaggaaac tgaggccaag gtcgcaggaa caagatgcct agactcacag  1440
cctgaatgga catgtccatg gaacccgtgg ccaccctggg gttggcaaaa cagatatatc  1500
tatgccacca ccactcctgc cctactgcag ccttgcagat gagcccagct ggttgccagc  1560
cccagaagct tcccagccct ccctccttcc ccctggggct gggctagggg aggaccccag  1620
aggagaggcc ctgattgtga ggcttttcca aaacagcctc ccctatccct ggcacgaggg  1680
gttgtccttc actgccctct ggagtgatga accctgaaat cccaagccct agggagatct  1740
gggcctgact caactaccag ttccacatca ctgggcccag tgagtgtagt cccaagaggc  1800
aacgtgacca agccaggagg acatgcgctt tggggtcaga acttgaacct ggacactcct  1860
cacttccttt gtcatcctgc tcaagccctc tcaccctcta aaccttagtt tccacctcca  1920
```

-continued

```
gaaaaatgat gcaaaccctc ccttcatggg caagttggac aacagaaccc gttctgggcc  1980
acaggtctga tacagacctt tgtttgtttg tttgtttgtt ttctgcagtg gcgcaatttt  2040
ggctcactgc aagctcctcc tcctgggttc acgccattct cctgccttag tctcccaagt  2100
agctgggact acaggcgcca gccaccacgc ctggctaatt ttttgtattt ttagtagaga  2160
cggggtttca ctgtgctagc caggatggtc tcgatctcct gaccttgtga tccgcccgcc  2220
tcagcctccc aaagtgctgg gattacaggt gtgagccacc gctcccagcc cagacctttc  2280
ttactgacag aatctggtct gggccagagg tctgatacag acctttctta ctgactcatg  2340
gataaaaaca ttgtctctcc agaaccaaag gccaggcatg ggcagccatg tggcccaagg  2400
tctagtctat gagagagtgg gggcagtccc agccccttga agactggggg cagccccttc  2460
tcactaggca gggctcagct ttacccactt cagtagagga tttttcagtt tttattcaaa  2520
cttcctgttt ttcttcccaa ttacacacat ctttttttcat tgtagaaaac ttagaaaatg  2580
caagtgagca aaaagaagaa aataaaatct ttagacctgg ggtggtggct cacacctata  2640
atcccagcac ttgggaggtc gaagcaagag gatgacttgt gtccaggagt ttgagaccag  2700
cctgggcaac atgacaaaat cctgtctcta caaaaataaa aaattagctg ggtgtgggtg  2760
acatgtgcct gtagtctcag ctactctgga ggctgaagtg ggaggattgc ttgagcctgg  2820
acttagaggc tgcagtgagc tataaccatg ccgttgcact cagcctggat gacagagtga  2880
gattctgttt caaaaaaaac tttaaaccta ccacccagag ataagccctg ctaattatgt  2940
gaaagagctt ttcttctctc tctctctctc tctctgtgtg tttatatgtg tttggggatg  3000
ggtgcacact cttcataaac tttttttttt ttgagacagg gtctcgctct tttgcccatg  3060
ctgtagtcca gtggcatgat ctcagctcac tgcaaactct gcctctcagg ttcaagagat  3120
tctccagctc ccaagtagct gggattacag tcatgcaccg ccacgcctgg ttaaattttg  3180
tatttttagt agagatggcc atgttggcca ggctggtctc gaactcctga gctcaggtga  3240
tctgcccacc tcagcctctc aaaagtgctg ggattacagg gcatgaacca ccatgcccgg  3300
ccttcatcaa tttttaaaa acgactttat tgaggtatac tttatgtatc acaaaattta  3360
cccattttta gtatatcatt caatgatttt tagttaactt tttgagttgt gtgacaatta  3420
ctagctgtcg aacattttta tcacacagtg agatccctta tacttcttta gtcagttcct  3480
gttcctgctc ccagccccgg gcagctgtgg atctgtatgt gtgtgtgtat atatatatat  3540
atatatatat attttttttt tttttttttt tttttttttt ttgagacgga gtcttgctct  3600
gtcgcccagg ctggagtgca gtggtgcgat cttggctcac tgcaagctcc gcctcccagg  3660
ttcaaacagt tctgcctcag cctcccgagt agctgggatt acaggcacct gccaccacgc  3720
ccggctaatt tttttgtatt tttagtagag atggggtttc accatgttag ccaggatggt  3780
ctcgatctcc tgaccttgtg atctgcccac ctcggcctcc caacgttctg gaattacagg  3840
cgtgagccac cgcgcccggc tggatctgta tttttataaa ttaaaatagg gtccattggt  3900
tcacagctga ttggaatctg cttggttcca tgtcaacagc cagacgacag taaggtttcc  3960
tcttattacc cacctgattc cctgtcgatg gacacctagg ttgttttatc tttataaact  4020
gctgcagtgg acactgaggc cggttttttt ctttgttttt ttttttttgt ttgtttgttt  4080
ttgagacaga gtcttgctct gtcacccagg ctggagtgca gtggcgcgat ctcggctcac  4140
tgcaaactcc gcctcccggg ttcacaccat tctcctgcct cagcctcccg agtagcttgg  4200
gactataggt gcgtgccacc atgcctggct aatttttttgt atttttagta gagacggggt  4260
ttcaccgtgt tagccaggat ggtctcgatc tcctgacctc atgatctgcc cgcctcggcc  4320
tcccaaagtg ctgggattac aggcgtgagc cactgtgcct ggccactgag gccagtcttt  4380
gcccggatcc tcactgtgtt cctaggatga ggttctggga ggggaattgc tggtcagagg  4440
tcgagcctgc ttttgaagct tcttctacca ggagtggagc tgagcaggtt tgataaggtc  4500
tgaagatttg gggtggaaa tgccaggtcc cttgagagac atgagggata agaggggcc  4560
aggctggcct tgagtgccag agtgcagagc tgggctagat gtgaggacag tcggggtca  4620
gagcaggggc acaccgagct tcagttccct ctggctgctt ggatggagga tcgtaatgtg  4680
aacagaaaac actaattgag tacttactgt gtttcagaca gtgtgttgat aatcccactt  4740
aatcccctga caaccccaag taggtagaca tatgatgaag atgacggcct tgaggaccag  4800
agaggttaag tgatttgcct gagatcacac agccagatga tggcaaagcc agaattcaaa  4860
cccaggctgt gggctccaga gcctagctct taagctctta agcactgggc tcctaagaat  4920
ggggatgagg ggttgaggga ggctcctcca caggggctac tctgggggcc tggaagtggg  4980
tcacagaggg gtcagaggct atgtggctac ctccccatcc cagtccagag cagtgtttga  5040
gtcattagac tgggaaccag ccctggtgag ccagccaagg gccttgggcc ccatccggtc  5100
ctgctgcctg ccacagccaa actcttgtca tgtgaatgga tttggggatg gagctgcctc  5160
catgagtcct tgcatctgtg ggtgaaggca ctgccctggc tatagtgtcc ctgggtttga  5220
gtcctgcatc tgcaccaaga cctcaggtga gcctgtctcc ttctgggcct cagagtacct  5280
tgcagctgtc gggggaggat ggatcaggag atggccctgt acctgtgttg gggattattg  5340
ttaagcccgt ggcagtcttc acctccctgc tgaggattaa tttatccaat tttgcacaag  5400
cttatgagtg cagaagaggc agacggaaac agagttctgg ccaagagcct ggaacagggc  5460
ctcggggtct ctttcctatg cctggacccc gtcatgtctg ctctttgtct gtcggacccc  5520
agatgtctgc caagccccgt cagaggctgc ttcccagaaa gcccttctgg gtgtcacctt  5580
gccccgagca gtgcgttctc agagttctcc cgccctgatg tccctcccag catgcccagc  5640
ccagccacaa cagggccttg cttctagtca tgtgtctggc tgtttgctgg gtccaggcca  5700
gccctggtag ggcacaatgg gggcccgctc tgccacccca tacctctccc caggatatct  5760
catgccccag ttctctccct agttccacca agcactggca ctccttagaa aacacagctc  5820
tagactagtt actgccctag cttacagcac agaactcccc tggtctccaa ccattcatgg  5880
ctccctagtg ctccaagata aagttccctt gtctcagccg ggttgggagt taccttctgc  5940
ccaacattca cctagctgga cacaaacatc ctgagtgacc cggtcagctc caggcaggag  6000
tcactgccag cagaggcctg ggatctggac tttgcctgct gacaggtgga gcccaggccg  6060
gccagaggaa gtgcctctga ccttgtctcc tagcagccac gggccatgtg gacatgcctt  6120
ttgaccctgg gcactgacag tgtgtgacag cctgcaccat gtgctccaca ggggcggctg  6180
tgtgtgtcgg gggtgaggtg gggaaagcct taactggctc aggggtgaga ggtcagggag  6240
ccattgagac tggctccagg tgtgggtccc ctgctgggtt ggggcttgtg ggaggtggga  6300
cggggctggg ggtccatccc cctaggggga atttgtggcc taccccgaac cctgtttgag  6360
ctcctttcct aactgactcc ccgtccctgc acctgtctcc cagcaggcct tgcctctgca  6420
tgctgcccct gccaggctct ggggtccctg tgctccctgc agctagaagg ctgggatcag  6480
gggtcttaac aagcagccct actgtatgac cttggacaag tccaagaacc ttcaggttct  6540
taacaatgta aagggagcag tactaaaagc agcttcttgg aattgtgggg atccgatgag  6600
tgaaggctta agcagtgcat ggcacatagt aggccctgaa ccaatgccag ttagtgttat  6660
```

-continued

```
tattatcacc atttagccag atgcagtggc tcacgcctat aatcttattg actttagagg  6720
ctgaggttgg aggattgctt gagaccagga gttcaagacc agcctgggca acatagcaag  6780
gccctgtttg ttttagagaa aacaaacaaa tcaccattta gagcacctaa ccagtacctg  6840
gcacgcgata ggtttagctc aacaaatgtt agcagcaatt acccaaggag cctgtgctgg  6900
aagtttctag gatgtaccag gctatggttc caagttctga gcatctacca tgtggtggtc  6960
tggagttggt gagagacagg atggggctga ctaggccagt ggggagcacc ccccgccatg  7020
gggaacaagc accctatcct tggcttccat ggaagataat tgatgctggg cacagtggct  7080
cacgcctgta atcccagcac tttgggaggc tgaggcaggg ggatcgcttg agtctgggag  7140
ttcaagacca gcctgggcaa cattgtgaga cccaaactaa aaaaattagc ttggcatggt  7200
ggagtgtgcc tgtcgtccca gctactcagg aggctgaggc taaagctgga ggattgcttg  7260
agcccaggag gttgaggctg cagtgagcca tgatcatacc actacactcc agcctgggca  7320
acatagtgag gccctgtctc aaaacaaaca aacaaaaaga acctgctgag gaagcagtgt  7380
ttctggctgg gggaggacgg gcagagtggc catctggcca cagatggcgg tttctgtgca  7440
aaacacatca aggcagcctt ggaaatgtga gtgaaagcac cttcaaagtt ctggtcacag  7500
ccttgggact aagcaaagcc accaaaagta cataaaagac aatgaccatc acccagtgcc  7560
ggtgatgcta gaaggaaagg gaatacgttg tagggaaggt tgtaaagggc tttatctttt  7620
ccagactgga gcctggcagc tcgaaaacat cttgctgcct tcatatgagc tttaaaacaa  7680
gctgcagaga aacaactcaa gagggagaaa tatatatata tatgtgtgtg tgtgtgtatg  7740
tgtgagtgtg tgtgtgtgtg tgtatacata tatatatata tatatatata tatatatttt  7800
tttttttttt taagatggag tctcgttctg tcaccaggct ggagtgcagt ggtacaatct  7860
cggctcactg caacctccgc ctcctgggtt caaatgattc tcctgcgtca gcctcccaag  7920
cagctgggac tataggcaca taccaccacg cccagctaat ttttgtattt ttagtagagg  7980
ctggatttca ccatgttggc caggatggtt ttgatctcct gacctcgtga tctgcctgcc  8040
ttagcctccc aaagtgttgg gattacaggc gtgagccagt ttgtttttag agacggggtc  8100
ttgctctgtc acccaggctg gaataccatg gcacaatcac agctcgctgc aatgttgaac  8160
tcccgggttc aagggatcct cccacctcag cctccagagt aatggagact acaggctcat  8220
gccaccatgc ccagctattt ttaaaacttt gtagagatgg ggccttgcta cattgcccag  8280
gctggtcttg aactcctggg ctcaagtgat ctgcctgcct ttgcctccca aagtgctgtt  8340
attacaggtg tgagcccctg cgcctaacct tagcactgcc attttgactg aaaacaggtg  8400
cccagcagca ggggctactc ccagaattgc cactgcatca ggcccgtggg ttgttttcag  8460
ctgccagtga taagtatgtg ccctgggcca cctctcggac aaggtgtctg aattggtgcc  8520
gaccagcatc acatgtaatt gccatctcgc aggtgctgct gagggtaatt ccgcacacct  8580
gtagctccgg gaagagccta gtggggagga ggaaacgtgg ctctgaggtt tatagggtca  8640
gacggtcagt atgttgggag ctggcatgtg gaggggcaca gacaagggaa gaatgggagg  8700
tggcatcaga gcaagttttg atggaggaat aggaattcac caggtggaaa gggcattcct  8760
ggtggaggga acagcctggc cttcaatagc ttgtggtgtt cagaaagcag gcagggaaag  8820
ggaggcccag ggagacacca gttaggggat gggggtggag gcagacgagg gtggaggaag  8880
ccatggctgg agtctgcacg gcctctgact ggggtccctg ctgtggtcag ccctgtgctg  8940
ggtgaggctg gggtcacagc tggttcaggc cctgacagga ggggccccca gctgaggccc  9000
agcctctaat ttggcagggc aggtggatag gtctgggggg gtggtggtta ggaagcctcc  9060
aggaggaggc agtgccggag ctgagcctta aagagcttcg tgttgtcctc tctgtctttg  9120
cactctgcac acactcactg aactgcgaca aatgaggata gctggtcagg gcagaggcag  9180
gccggagttg gggctcactg ctgtccccca caggctgggg ctgaagggca ggctctgggg  9240
ccgcagaatg gggtttgtgt accagattct tcatatggca gctgtgggac tttgggcacg  9300
aggcctccgt ctgagcctta gtttcctcaa gaggacctgc gcccaggtgc acctggggct  9360
ccagccatgg gtgcgtccca ttccgggaag agctggcaca cacttgtgcc cccggggcag  9420
ccatgagtgc acaaagggca gcctgtgcca ctgctggata cacgaccagc tgagaacacg  9480
aggaccgccg actccagtta ggaggatcaa ggaagtgcct ggtgggagca gaacagcagg  9540
tggggtgcag cccagctccc tggagggatg gtgggcaccc atcctcaccc tgctgcctcc  9600
attagcaggc cgagagggtg tgctctggaa tcccatgagc acctgtgcca catcctcccc  9660
tgtggctgac ccttcttcac agttggtgca gctttgtggt ctgtagtgca gggatcaatt  9720
ggcaaatccc tttcccaccc attccctgga gaattggggt ccttggctca gatgacagac  9780
caacctgagt tggaatccca gctccttggt ggccgtcctg gcctccaccc cctcactgcc  9840
tccgctcctc ctatcctgcc cacgcccact gcagggcctt tgcacacact gtttcttctg  9900
ccctcccttc cggcccactc cctcatatca ttcagtcctc ctttcagatg tcacctccta  9960
agatgggctg ccctgaccac ctcatctata atggccccag tgcctggcac aggattggca  10020
cacagtagat attgtcagag atggatctgg gttctgtgga caaggctgtg ggggcaggtg  10080
aagagctccc tcttccagga ggttgtttgg ggttcaaggc cttgtttggg ttgtaggctt  10140
ctgtgctggt cagcgttggg ccctacaagc gcatgccatg aggcctgccc aggatttccc  10200
tcatggcctc acagaataca tcggccagag tcattaaagg gcgcctgcat ctgccttcag  10260
agagaggttt gaaggtagaa ctggggaggg atgccaggtg ggggttcagg tttcctgttg  10320
ggtcctgata gaatcagggc aggagaggaa gaagaagagg gaagaggagg aacccaggct  10380
tggggagggg tggcagggct tcacaagcct ggggaaggtg aactagggag cagttggggc  10440
caccatggcc cagagtctat gcctcctctt ccttcctgtg ttcagagtgt gtgtgggaac  10500
cacaagggcc ttctcagtgt tcataggga a gcccggttca cccatgggtg ggccgcaatt  10560
tgggtgccac agtgagcccc tagagaccag ctctcccagc ttccaggaca gggactaggg  10620
gaggcaagag aggctcttcc ttaaattgtg cacccaaggt gcctcagctg ccttactcta  10680
gactggcccc gttaactccc cttaaaaaaa aaaaaaaaaa gactcagtcg aatggtaatg  10740
gagctccaac gtgaatactg caagtatcag gcaactcact acctgacttt ccagttctaa  10800
accattctaa ttgctgtaga gagaactaac ctttgttgag actgttgagt gatggatgtt  10860
ttacacactt gctttcccag aattcccacc tctggagatc gtaggtgtgg gagctcagag  10920
ggtggggagt ggactgtccc catcacacag caagggaggg gctaaaggaa gagcagggcc  10980
tggcatgcag ccccagatag cccacttggg tgtgtctctg agggaggctg cagggctggc  11040
tctagagttt cctttttcag tcttaacctg gtgaccagct tccacagaaa ttggcacggt  11100
gactcatgcc tgtaatcgca acacattggg aggccgaggt gggaggatca cctgaggtca  11160
ggagttcgag accagcctgg ccaacgtggt gaaaccctgt ctctactaaa aatacaaaaa  11220
ttacatttca ttacaggtgt ggtggcgcac acctgtaatc ccagctactc aggaggctga  11280
ggcaggagag tcacttgaac ccgggaggta gaggttgcag tgagctgaga tcgtgtcact  11340
gcactccagc ctgggtgaca gagccagact ctgtctcaaa aaaaaaaaaa aaaaaaaaag  11400
```

-continued

```
aaattggcca gtagatcagc cccaggggag agtgagccag ggtttggcca ggccttgagt  11460
ttcagaggct ggccatggcc agtggcaccc aggcccttcc cccttcctcg gggcatctta  11520
gcttagtctg tgccctctgc ccaagggcca gccctctgtt cccaggtcac accccctcct  11580
cttggaaggc ccccccgcc ccaccccat cagagtcttt aatgactctg ctgcccctgg  11640
ggctcagaga gcaaccgccc tctcccatcg cgcttcctca gtgggatggg agggggttag  11700
agcaggaaga tgagacaaat aaagacacaa taagaggcag gaatatgtgg taaagccaag  11760
atgggtaagg ggaggggaca ggcttgactg ttcacagtgg ccctggccct gctgtctcag  11820
gctagtatct gcttgttggt ctcaccacat tctaggctca gaaactgggg agcaaagtaa  11880
tgaaagaacc aggctgggag gccatgggga actcatgcct ggagttcagc tctcagtgtg  11940
cttttgggtc aaggacgctt ccctgtctta agtcactcat gtcagagcct ttgccaagag  12000
caatgctgtg ttttgttttg ggggtgaggg aacacccgcg ggctgagggg agggttgggc  12060
catgctagag aggccgtctg ttgtccttga acctcccaaa gctgggaaat aagggcctgg  12120
gctggacggc ggtggcgagg acaggttgcg agagagacat ggctgggttt tcttgcttag  12180
ggtcctgaat agagagcaag gttgaggccg cagggacccc agcccccaat ggactgctga  12240
gtcgctgggt ctgcccaggg ttcaggcacc ctctcaggtt gcagccaact ggggtgtgga  12300
ccaggcagag gcgctggcct gcagtttggg gcagaggcag gctttgctgg tggtctactt  12360
ggctgcaaaa tcaactggcc aggctctgat cactttgtgt gtgtgtgtgt gtgtaacttt  12420
tacctttgac aaaagaggga agacaggccc aggcacctcc tcaaaagaac cctagagcct  12480
gtcacccctt ccttacccat cttctgtcct agggactgca gcccttcctg gcttcccagg  12540
gccctacaat gaatagtggg tcgggactca cttggtgact gctgggttgt gaggccttga  12600
gggggagggg cagacttcac ccatctggca gagggacatc ggtgctggca gtcaggaaac  12660
ccttatttcc aggcctcagt ttcccggaag tgacctgttt tcaggagtgg cctcatccca  12720
gaccatcagc cccgctgtgg tgaggggtgg ccccttcctg gggctgccct agaaggggga  12780
ggtccctgca cccaccgcag ctgccactcg gcagcccttg gccttaatta aacgcttctt  12840
gcgtactaag tgctgcaccc atattatctc ccttctacca ttcgacgcca gggagataat  12900
gactgtcctg ttttctggag gagtaaacgg agggttggag cggttaaggc tcgctcaggg  12960
tgccagcgaa ccagtgattt cgaacacaga gttctggtgt gttgggccag gacttctctg  13020
ctttgaccct ttaacgaagg gggcgggagc tgagggccag tgaccgccag taaccccggc  13080
agacgctggc accgagcggg ttaaaggcgg acgtccgcta gtaaccccaa ccccattcag  13140
cgccgcgggg tgaaactcga gcccccgccg ccgtggggag gtggggcggg ggccggggcc  13200
gggccctagc gaggcggcag cgcggccgct gattggccgc gcgcgctcac cccatgcccg  13260
gcccgcagcc ccgaagggcg gggcggggcg ggacctgcag gcggggcggg gctggggcgg  13320
ggctggggc ggggcggggc ggggcgggcg cgccgcagcg ctcaacggct tcaaaaatcc  13380
gccgcgcctt gacaggtgaa gtcggcgcgg ggaggggtag ggccaacggc ctggacgccc  13440
caagggcggg cgcagatcgc ggagccatgg attgcacttt cgaaggtatt tttggaggcc  13500
tccccaccag ccctttatac aatgcctccg tctcctgcag gttctcctgg ggtgggcggg  13560
catgcgggct acgcaacttg agcaggaaag agccccttcc cgagggagaa ggtgtgacag  13620
ttaccagctc gctggggaag tggagggcta cctccaacca aattagtgtc ccctgcaact  13680
caagggggaa gggtttgctt agagacccaa aagcagcatc ccgacctaag agggtttgga  13740
gggagagggt ggtcttctct acattctctg cacccgcttt gggacaggac caggaggaag  13800
cagggaggag ggcccgttgt ccctctgcca cagcgtctgc cctattcagc acccctgcct  13860
attgtgggca tcttagactt ttcaggaaga cagtgggagc cctagattgt caaaattgtc  13920
agtttttctt tcaggcctca gtttccccca tctatcgaag aggctcacac ggactggggt  13980
aaagggatgg gaaaccctgc agttgaaagt ccattatgac ttgatgactt gtgacctggg  14040
gggtccacaa accaggagag tttctacttg agaagccagg aagactgggg ctgccacccc  14100
atcctgttct gccaactgct ctaggaaatt cccctcctgc agtagcttcc ctgcctgggt  14160
acctgtcagt aggcaatgtt gggtctccac tcggtgccag ctgcctgcca agcaaagcct  14220
cgggcagccg taccaaaagg ggtttagtct tttctgttgt acagatgagg aaactggggc  14280
cagtgagagg aggctgttgg tccaggctcc acttcaagct ggtggtgggc agggctggga  14340
gctcaggctg gggatcctga gagcactgga ggcccccatg ggtcctgtag agcattctga  14400
cccagtgggt gccaccacga gtgggttaga gggccctggg ctgagccaga taggctgcta  14460
gtcaccagct gggggagagg gcccttggcc aggtggggct gaggtgggag tgtgtcccag  14520
tctgtatgag gaggaaggag tcaggacaga cagcacttgc ttttacagag atgaaatcaa  14580
agccctgagt ggccaggcct gggtcttgag gctacttggc tgcaggcaaa gcctggactt  14640
gagcccagaa ctctacacag agacacactg gttggccatg tggccagcag ctggcttggc  14700
cctaagcctt ggtctgttcc actgagtaat gggttggtga tggcagcctg gctcttggct  14760
tcttagtggg gcaagaaaag gcagagagac aatagatttg ggattttgta gacctgggtt  14820
tgaaccccac tgcatgctct tgggctgctt gtggtcctcc ctgagcctca gtgtcttttc  14880
ttgtctccaa gatgaggtga gctaatcttt tgaggtagtc tagggtagtg gccagtggtt  14940
ggggcattgg agtcaaaata gggtctggac tcagttgagt ctctgactct ataagaactt  15000
aggccagtaa gtcacctctc tacagctcag tttcttcacg tgtagaatgg ggccaatgat  15060
cacatcaccc tctcagctgt gggtgaggat taggggtcta gcctggcccc atcaatgtgg  15120
gtagccccac agcgggcctg gcttttggac cagacccacc cttctgacat gggcccccac  15180
ccttagagtc cttctagtgt ggatgaggac cctgctctga tctggggtcc tcttgggga  15240
cttccctgtc tgccattctc tttggggatc ctgcgctgcc ctaggaagag tgggcccagg  15300
ctgcacagtt ggtccttggt cacagaggat cccaccactt cttcagggcc tcaaggcaat  15360
cctgcctctc tctgcacccc tcttccccct gtaaactgag gggaggggaa aatcacccac  15420
tcctcagcag tttctaagtt gctttgtcaa attcagtgcc cagaggatcc tgctgggggt  15480
gcgttttagg atgagaccag gagtggccaa tggtggggtg tggggcccat cgctcctata  15540
tgaagacccc ctctgcccta gactgctcct ccctccccat ccccatctcc atcccaaaga  15600
ctggagctgc tggatctgtg gatggaggcg tgcccccgt ttcacacatt gagaaacagg  15660
ccccaagtgg agccagggaa ggctgcacct gggcctctgg attccttttg ttctgtgtgg  15720
ggttgggggt gatggactgt ggagagggca ggagagctgt ctggaagggt tggtcacctc  15780
atgggcaaat gcttggaagc tggtctgagt ccacggtgca gtgtgtatgt gtgtgtgtgt  15840
gtgtgtgtgt atgtgtgtgg actcagaggt ggatgtcttg tagaatgcat gccccatgaa  15900
gacaggagta aaagtttacc accatccaca tcaagctaca ggacactccc agctccccag  15960
aaagttgctt agttctaggc agggatttcc cttattcaca gccgggagca gtgcctggca  16020
tagtgtgggc actcagcact cagcacatgc tcactggatg agtgaatgaa tgtgagcctg  16080
ctgtttgctg tggactaagg atgtttctag atgtttgggc aaataccgga tggtgggaag  16140
```

```
agctcaggct ctgaagtctg cagtcttggg cccgaccctg ggctcagccc cagcctagct  16200
gtggggcaag attgtgagcc ttgtggtgcc caccttgtcc aggtattgtg atgcactcgc  16260
agcagcaggc attgctttag acagcacagg tgctcgcaaa atggctgtat gtccgggaac  16320
accagctcct gtgggtggct ttctgtcctg gtggcattgc ccacacatac agctgtgtgc  16380
caacaagggt tgtgcaaata aggttgtgtt tggatgtgtg tgatgccctg tttgggggtc  16440
agtctctgcc tcactcacgc accctcttct ccttttcaca gacatgcttc agcttatcaa  16500
caaccaagac agtgacttcc ctggcctatt tgacccaccc tatgctggga gtggggcagg  16560
gggcacagac cctgccagcc ccgataccag ctccccaggc agcttgtctc cacctcctgc  16620
cacattgagc tcctctcttg aagccttcct gagcgggccg caggcagcgc cctcacccct  16680
gtcccctccc cagcctgcac ccactccatt gaagatgtac ccgtccatgc ccgctttctc  16740
ccctgggcct ggtatcaagg aagagtcagt gccactgagc atcctgcaga cccccacccc  16800
acagcccctg ccaggggccc tcctgccaca gagcttccca gccccagccc caccgcagtt  16860
cagctccacc cctgtgttag gctaccccag ccctccggga ggcttctcta caggtaaggg  16920
ggatgtgtgg cgggagggga cacccggggt ggggcttcca ggagcacagg aagaagcttc  16980
tgctgtgatg tgagtagagg tctgtgcagg ctttagaaac tggggctcca ctcggctgct  17040
tgagatgccc tgttactagc agtcctggtg tgcttgttgc cggggtaggc gcaacctcgc  17100
actggaggcc tggcttgaag ccagtgcatt tgcatcagag cccaggcagg gactgtccat  17160
aggaagccac atggggcaat gactcatcca aggccagtcg gtgatagaga cctgaagagc  17220
aggttgaaag tgggagaggg aggtctgtgt ctgcagcccc atgctttatt tctgcaggaa  17280
gccctcccgg gaacacccag cagccgctgc ctggcctgcc actggcttcc ccgccagggg  17340
tcccgcccgt ctccttgcac acccaggtcc agagtgtggt cccccagcag ctactgacag  17400
tcacagctgc ccccacggca gcccctgtaa cgaccactgt gacctcgcag atccagcagg  17460
tcccggtgag gggtctggc caggggttgg ggagggggca gccccagccc agacacacag  17520
cttacagcca agcctctccc accctcaggt cctgctgcag ccccacttca tcaaggcaga  17580
ctcgctgctt ctgacagcca tgaagacaga cggagccact gtgaaggcgg caggtctcag  17640
tcccctggtc tctggcacca ctgtgcagac agggcctttg ccggtgggtg acgtgggcag  17700
ggcataaggg agtggggtct acacacacac acacatgccc acctggtaac atgtgcctgg  17760
ccctgcagac cctggtgagt ggcggaacca tcttggcaac agtcccactg gtcgtagatg  17820
cggagaagct gcctatcaac cggctcgcag ctggcagcaa ggccccggcc tctgcccaga  17880
gccgtggaga gaagcgcaca gcccacaacg ccattgagaa gcgctaccgc tcctccatca  17940
atgacaaaat cattgagctc aaggatctgg tggtgggcac tgaggcaaag gtgtggagag  18000
gcctgcaggg gcacagaccg gggtgtccct aggaaggaac agatcagggg caactggaag  18060
gaagagaggg agtgagactg agcctggaca agcagggaat tggaattcag cctccccagg  18120
cctggccagc ctcgtttatt tagttaaact ggtttgcagg cctcttcaat aaaggtgggg  18180
ctgtgctagg cattggggat gcagcaatga acaagacaga caaaaattgt ccctcaaaga  18240
agagccgacc ttctggtggg ggagatggac agtaggcagg atgaataagt gctcgagacc  18300
accacgtttg gctcgttgca gagaaagcag gaagaggatg gtgagggtcc cctggtggta  18360
gccagggaag gcctccctga gatggcggca ggcacagcag cagctagcca gaccctgctg  18420
tctgcatctt acattctaac cctatgcccg gcctgggagg tgggtgctac taggcgagga  18480
acggttcagg tagaaggaac aagtgcaaag gtcctgaggc agtaatgttg caaagcagct  18540
ccgcaccccc ttgctagggc tctccaaccc cacaaccccc gacctgacag gccacctgtg  18600
cgctccccct ccctcccaca ccgtgcagct gaataaatct gctgtcttgc gcaaggccat  18660
cgactacatt cgctttctgc aacacagcaa ccagaaactc aagcaggaga acctaagtct  18720
gcgcactgct gtccacaaaa gcagtgagtc ctggctttat tgagctccag tctggcctct  18780
tctctagcct tgctccacct cccggcccca ccccatccct agccccaccc cacccttggt  18840
tctggcccac cctctgccct gcccacctca cccttggctg tagccctgca ttcagctcta  18900
gtcccttggt tacctctggt cctgaaagag acctggtgcc tccctttggc cctaacccag  18960
ccccatcaaa gcgtcctggg ctagctttag gagctacagt agtccctagg cctccaaggg  19020
cctaggctct gatttggggt cacatatcca gcctttactc ctggctctgt tcctttcggc  19080
ccacagaatc tctgaaggat ctggtgtcgg cctgtggcag tggagggaac acagacgtgc  19140
tcatggaggg cgtgaagact gaggtggagg acacactgac ccccaccccc tcggatgctg  19200
gctcaccttt ccagagcagc cccttgtccc ttggcagcag gggcagtggc agcggtggca  19260
gtggcagtga ctcggagcct gacagcccag tctttgagga cagcaaggtt gggccctgcc  19320
acggtgcccc cttccccact cccagccata tcctctgagc ctcatgacag ggccgggaag  19380
accctaacag atcctacctc ccatttcata gacagaataa ctgaggcctg gagccacgtg  19440
gggtcccaca gtaaggtggg cagaatcctg acccccccct tcccagcccc atgctctctg  19500
gggtccctcc gattctgccc tcaccaccct gcccaacccc accaggcaaa gccagagcag  19560
cggccgtctc tgcacagccg gggcatgctg gaccgctccc gcctggccct gtgcacgctc  19620
gtcttcctct gcctgtcctg caacccccttg gcctccttgc tgggggcccg ggggcttccc  19680
agcccctcag ataccaccag cgtctaccat agccctgggc gcaacgtgct gggcaccgag  19740
agcagaggtg ggaccggcca gcctgggcat ctttgggagg gacactcggg gtgagccccc  19800
aggcttgtga acttggggct ctggatttcc tgggagctgt gtccccagct ttccctctgt  19860
ccatagatgg ccctggctgg gcccagtggc tgctgccccc agtggtctgg ctgctcaatg  19920
ggctgttggt gctcgtctcc ttggtgcttc tctttgtcta cggtgagcca gtcacacggc  19980
cccactcagg ccccgccgtg tacttctgga ggcatcgcaa gcaggctgac ctggacctgg  20040
cccgggtaag gggctggccc cggcagagtg ggcagggcag ggaccccagg ctgtgaaggt  20100
gctgggtgtc aacccttgtt cctgctccct gtgcacacca tgaatctgtc ccgtcctccc  20160
tgtgcctagc cacgcatccg cagaccccca ccacccctcc agagcctgct gtggacggct  20220
cttctgagct ttggggcagc tgctctgacc tcacttttct cacctggaaa accctcatcc  20280
acagggagac tttgcccagg ctgcccagca gctgtggctg gccctgcggg cactgggccg  20340
gcccctgccc acctcccacc tggacctggc ttgtagcctc ctctggaacc tcatccgtca  20400
cctgctgcag cgtctctggg tggccgctg gctggcaggc cgggcagggg gcctgcagca  20460
ggactgtgct ctgcgagtgg atgctagcgc cagcgcccga gacgcagccc tggtctacca  20520
taagctgcac cagctgcaca ccatgggtag gactgagcgt ggggcgggct ccgaggtgct  20580
ccctgctgcc tgtgctccac ccacagcctc atgcctgctt gccttccagg gaagcacaca  20640
ggcgggcacc tcactgccac caacctggcg ctgagtgccc tgaacctggc agagtgtgca  20700
ggggatgccg tgtctgtggc gacgctggcc gagatctatg tggcggctgc attgagagtg  20760
aagaccagtc tcccacgggc cttgcatttt ctgacagtga gtgggttggg gggctggggg  20820
cttatccctg cagctctctc cagaggctcc ctgggtaaga gctacacggg atgtggcagt  20880
```

```
ggttaccagg gggactccag gccaagctgg gactcggccc ggggtctggc cccaggctgt  20940
gtccactgtg acagcccagt accctcccct acagcgcttc ttcctgagca gtgcccgcca  21000
ggcctgcctg gcacagagtg gctcagtgcc tcctgccatg cagtggctct gccaccccgt  21060
gggccaccgt ttcttcgtgg atggggactg gtccgtgctc agtaccccat gggagagcct  21120
gtacagcttg gccgggaacc caggtgctct cttacccctt ccctgtcccc tctcctgtcc  21180
ctcatcctca ttcctgtcct gtcccttgtc gcctgaatct ctggctgtct ctggccaccc  21240
cagtccttct ccctgccatg ggttgttgct gtgggggttg caggaaggga aaggcctggg  21300
tgcctctcgt tcccattggg gctttcagaa gcacatgcag ggattgatgg gcagatggct  21360
aattggagaa gtgaccccag gcagtgccgc tgtggagtaa ggaagcggag ccaacaatgg  21420
catcttctca agtcggtttt cctttggaag cagtgtaggg caggcctcag tgttgtctcc  21480
tggccaaggc tggtgctggt gatagttatg tccacccgct ttcccctgtc cttggcaggg  21540
gctgcaccca ggggcatgcc ggcacttccc agtggcccta ggtgtggccc cagcccaccc  21600
aggaaaaagc ccttagcttg gagaggaggg tggggccctg ctccccaccc cactcacctc  21660
ctcctctcca cagtggaccc cctggcccag gtgactcagc tattccggga acatctctta  21720
gagcgagcac tgaactgtgt gacccagccc aaccccagcc ctgggtcagc tgatggggac  21780
aagtaagtgt cgttgtgccc tcctccaggc aaggcccctc cggcgggatt ctgagaatag  21840
ctctggcctc aaccctgtgg agagagccca gagctgggct accgtgcgtg ccatgcacgc  21900
ttcattcctc tctgagtttc ctctccccac cagcctgtgg gaggagacag tggcactttg  21960
cagagccagg ggccaggctg tactctggag ggcaggtggg gagcacctc ctaggacccc  22020
tgccatctgt tccgacagcc agctctctcc ttccacaggg aattctcgga tgccctcggg  22080
tacctgcagc tgctgaacag ctgttctgat gctgcggggg ctcctgccta cagcttctcc  22140
atcagttcca gcatggccac caccaccggt gagtccccgg cccctgtcct ggctcccttc  22200
tcagctcccc cgtgcagcgt gactgagggt tcaggggacc ctccctcttc tgcaggcgta  22260
gacccggtgg ccaagtggtg ggcctctctg acagctgtgg tgatccactg gctgcggcgg  22320
gatgaggagg cggctgagcg gctgtgcccg ctggtggagc acctgccccg ggtgctgcag  22380
gagtctgagt gagtgcacgg caggttcctc ctgcctggtc ccgggctcag ccttcctcat  22440
cccctgggca ctgtgcctca ctcagccttt gttctgtgca ggaggagtca ccaccttttt  22500
tcctcaggga actcgagcca gggaagtggg gggcactcag ccagggcttg tggactggtc  22560
tgactggcac tcttctgccc tggtcccaac aggagacccc tgcccagggc agctctgcac  22620
tccttcaagg ctgcccgggc cctgctgggc tgtgccaagg cagagtctgg tccagccagc  22680
ctgaccatct gtgagaaggc cagtgggtac ctgcaggaca gcctggctac cacaccagcc  22740
agcagctcca ttgacaaggt gaggggtggg gtcaggggcc tggcagggct gggggattca  22800
gctttccatt ccctggttcc tctccccagc ccccaggggc tgcagaagac catggggtta  22860
gcccaagcag cacaggatag ggggtccagc agaccctgct ttttggctaa ggcttctgtc  22920
cagaggagag gggttgcccc tatctggcct cagtttcccc atccctggga ggagggggt  22980
ggatggtgtg gtaggatccc tttggaggcc ctgcatcagg agggctggac agctgctccc  23040
gggccggtgg cgggtgtggg ggccgagaga ggcgggcggc cccgcggtgc attgctgttg  23100
cattgcacgt gtgtgaggcg ggtgcagtgc ctcggcagtg cagcccggag ccggcccctg  23160
gcaccacggg cccccatcct gcccctccca gagctggagc cctggtgacc cctgccctgc  23220
ctgccacccc caggccgtgc agctgttcct gtgtgacctg cttcttgtgg tgcgcaccag  23280
cctgtggcgg cagcagcagc ccccggcccc ggccccagca gcccagggca ccagcagcag  23340
gccccaggct tccgcccttg agctgcgtgg cttccaacgg gacctgagca gcctgaggcg  23400
gctggcacag agcttccggc ccgccatgcg gagggtgagt gcccgatggc cctgtcctca  23460
agacggggag tcaggcagtg gtggagatgg agagccctga gcctccactc tcctggcccc  23520
caggtgttcc tacatgaggc cacggcccgg ctgatggcgg gggccagccc cacacggaca  23580
caccagctcc tcgaccgcag tctgaggcgg cgggcaggcc ccggtggcaa aggaggtgag  23640
ggggcagctg ctgaccaggg atgtgctgtc tgctcagcag ggaagggcgc acatgggatg  23700
tgataccaag ggaggctgtg tgtgtgtcag acgggacaga caggcctggc gcagtggctc  23760
acacctagca ctttgggagg ctcagttggg aggacagctt gagcccagga gttggaggcc  23820
gcagtgagcc tgagtgacag ggagagtccc tgtctcaaaa aaaaaaaaag accaagcatc  23880
ttcttgatgg ttacctgatg acaattcctt tcacaaggaa tcagtggggt gactgtcatt  23940
tgtgggatac atgactgcac gtgcgtgact cagtctgtgg actttgtgtg tgggctgaga  24000
ctagggtggg gagaggggaa cccgccaggc ccccgccagg tacctgtgtg ccaggtacag  24060
gcggctggtg ccgtggcttg tgtgtgggca gggctcccgc gggggcgtgg ccagcttgag  24120
acccatccct gacacatcct cgtgtgcgca ggcgcggtgg cggagctgga gccgcggccc  24180
acgcggcggg agcacgcgga ggccttgctg ctggcctcct gctacctgcc ccccggcttc  24240
ctgtcggcgc ccgggcagcg cgtgggcatg ctggctgagg cggcgcgcac actcgagaag  24300
cttggcgatc gccggctgct gcacgactgt cagcagatgc tcatgcgcct gggcggtggg  24360
accactgtca cttccagcta gaccccgtgt ccccggcctc agcacccctg tctctagcca  24420
ctttggtccc gtgcagcttc tgtcctgcgt cgaagctttg aaggccgaag gcagtgcaag  24480
agactctggc ctccacagtt cgacctgcgg ctgctgtgtg ccttcgcggt ggaaggcccg  24540
aggggcgcga tcttgaccct aagaccggcg gccatgatgg tgctgacctc tggtggccga  24600
tcggggcact gcaggggccg agccattttg gggggccccc ctccttgctc tgcaggcacc  24660
ttagtggctt ttttcctcct gtgtacaggg aagagagggg tacatttccc tgtgctgacg  24720
gaagccaact tggctttccc ggactgcaag cagggctctg ccccagaggc ctctctctcc  24780
gtcgtgggag agagacgtgt acatagtgta ggtcagcgtg cttagcctcc tgacctgagg  24840
ctcctgtgct actttgcctt ttgcaaactt tattttcata gattgagaag ttttgtacag  24900
agaattaaaa atgaaattat ttataatctg                                  24930
```

```
SEQ ID NO: 2            moltype = DNA  length = 24930
FEATURE                 Location/Qualifiers
source                  1..24930
                        mol_type = genomic DNA
                        organism = Homo sapiens
SEQUENCE: 2
gcggccgggg gaacccagtt tccgaggaac ttttcgccgg cgccgggccg cctctgaggc  60
cagggcagga cacgaacgcg cggagcggcg gcggcgactg agagccgggg ccgcggcggc  120
gctccctagg aagggccgta cgaggcggcg ggcccggcgg gcctcccgga ggaggcggct  180
gcgccatgga cgagccaccc ttcagcgagg cggctttgga gcaggcgctg ggcgagccgt  240
```

```
gcgatctgga cgcggcgctg ctgaccgaca tcgaaggtgc gtcagggcgg gcagggcttg  300
aagctgcgcc gggtggcgcg agtagggggc gcgcaggtgt ctccctggcc tttgtctccc  360
ccacgggcgc cagctccgtg ctgtgctcgc gcgggacttc ccggtgtctc tgagctcggt  420
gtcccgagcc tcaccgagcc tccctggttc ccgcgctagc gtctcgggcc gcgcgcttgt  480
gggtgagggc tcctgggccg ggccggggtc ccttggcggc tccgggccgg gacacgtgcg  540
cctctacgcg tcccaggccg ggtgccgccc gaccggtgac tctccagccc tgtgatggcc  600
acggctgaag ctggggaccc aggcgtcgcc gaagctccgc cccagcccca gccgtgacgt  660
aattgcgagg ttactcacgg tcattccctc cggcccgaga gttcagctcg gcgtcggagc  720
tcttgcgcat gcgcatgggc gctgcctcgc gcccttcccc cgcctcgtgt cgggttctcc  780
cggtctgcga cgggcacagc ctccgcactc attcactgac atccaccgaa tgccaggccc  840
cgtcttaggc accgagggtt tacagacaga cctgggtacc ccctctttta gggaacacaa  900
aaatctcccg ggaaaccaaa cgggtattta gttgtacctt gggtggagcg aggctggggg  960
agggcaggga tgtggctact ttgggtagag cggtcaggga cttctaagct gagacctgag  1020
ggtcaccccc aggaccagca aggaaagatg ttttccaggc cacggcaagg gaagggcaaa  1080
ggcctcgagg cagggcctaa gtgtgaggag ttagaggctt gcaaaggagt gaggtcaggg  1140
aggaggagga cgcaaaccga cttggtcggc cagggaaagg gcggagcaga acagtggcac  1200
cggcttccat ctttggagca tcaccctggc tgtgatgaga aggggtttgg ggccaatggt  1260
ggcaccaagt gccaattagg aggcccgttg cttccatttt gtagatagag caaacggaag  1320
cccctagcaa attgcctgca tggtttctgt gcaggagttt tagcagcact agctaagttg  1380
cacttggttg atgaggaaac tgaggccaag gtcgcaggaa caagatgcct agactcacag  1440
cctgaatgga catgtccatg gaacccgtgg ccaccctggg gttggcaaaa cagatatatc  1500
tatgccacca ccactcctgc cctactgcag ccttgcagat gagcccagct ggttgccagc  1560
cccagaagct tcccagccct ccctccttcc ccctggggct gggctagggg aggaccccag  1620
aggagaggcc ctgattgtga ggcttttcca aaacagcctc ccctatccct ggcacgaggg  1680
gttgtccttc actgccctct ggagtgatga accctgaaat cccaagccct agggagatct  1740
gggcctgact caactaccag ttccacatca ctgggcccag tgagtgtagt cccaagaggc  1800
aacgtgacca agccaggagg acatgcgctt tggggtcaga acttgaacct ggacactcct  1860
cacttccttt gtcatcctgc tcaagccctc tcaccctcta aaccttagtt tccacctcca  1920
gaaaaatgat gcaaaccctc ccttcatggg caagttggac aacagaaccc gttctgggcc  1980
acaggtctga tacagacctt tgtttgtttg tttgtttgtt ttctgcagtg gcgcaatttt  2040
ggctcactgc aagctcctcc tcctgggttc acgccattct cctgccttag tctcccaagt  2100
agctgggact acaggcgcca gccaccacgc ctggctaatt ttttgtattt ttagtagaga  2160
cggggtttca ctgtgctagc caggatggtc tcgatctcct gaccttgtga tccgcccgcc  2220
tcagcctccc aaagtgctgg gattacaggt gtgagccacc gctcccagcc cagacctttc  2280
ttactgacag aatctggtct gggccagagg tctgatacag acctttctta ctgactcatg  2340
gataaaaaca ttgtctctcc agaaccaaag gccaggcatg ggcagccatg tggcccaagg  2400
tctagtctat gagagagtgg gggcagtccc agccccttga agactggggg cagccccttc  2460
tcactaggca gggctcagct ttacccactt cagtagagga tttttcagtt tttattcaaa  2520
cttcctgttt ttcttcccaa ttacacacat ctttttttcat tgtagaaaac ttagaaaatg  2580
caagtgagca aaaagaagaa aataaaatct ttagacctgg ggtggtggct cacacctata  2640
atcccagcac ttgggaggtc gaagcaagag gatgacttgt gtccaggagt ttgagaccag  2700
cctgggcaac atgacaaaat cctgtctcta caaaaaataa aaattagctg ggtgtgggtg  2760
acatgtgcct gtagtctcag ctactctgga ggctgaagtg ggaggattgc ttgagcctgg  2820
acttagaggc tgcagtgagc tataaccatg ccgttgcact cagcctggat gacagagtga  2880
gattctgttt caaaaaaaac tttaaaccta ccacccagag ataagccctg ctaattatgt  2940
gaaagagctt ttcttctctc tctctctctc tctctgtgtg tttatatgtg tttggggatg  3000
ggtgcacact cttcataaac ttttttttt ttgagacagg gtctcgctct tttgcccatg  3060
ctgtagtcca gtggcatgat ctcagctcac tgcaaactct gcctctcagg ttcaagagat  3120
tctccagctc ccaagtagct gggattacag tcatgcaccg ccacgcctgg ttaaattttg  3180
tatttttagt agagatggcc atgttggcca ggctggtctc gaactcctga gctcaggtga  3240
tctgcccacc tcagcctctc aaaagtgctg ggattacagg gcatgaacca ccatgcccgg  3300
ccttcatcaa ttttttaaaa acgactttat tgaggtatac tttatgtatc acaaaattta  3360
cccattttta gtatatcatt caatgatttt tagttaactt tttgagttgt gtgacaatta  3420
ctagctgtcg aacattttta tcacacagtg agatccctta tacttcttta gtcagttcct  3480
gttcctgctc ccagccccgg gcagctgtgg atctgtatgt gtgtgtgtat atatatatat  3540
atatatatat attttttttt ttttttttt ttttttttt ttgagacgga gtcttgctct  3600
gtcgcccagg ctggagtgca gtggtgcgat cttggctcac tgcaagctcc gcctcccagg  3660
ttcaaacagt tctgcctcag cctcccgagt agctgggatt acaggcacct gccaccacgc  3720
ccggctaatt tttttgtatt tttagtagag atggggtttc accatgttag ccaggatggt  3780
ctcgatctcc tgaccttgtg atctgcccac ctcggcctcc caacgttctg gaattacagg  3840
cgtgagccac cgcgcccggc tggatctgta tttttataaa ttaaaatagg gtccattggt  3900
tcacagctga ttggaatctg cttggttcca tgtcaacagc cagacgacag taaggtttcc  3960
tcttattacc cacctgattc cctgtcgatg gacacctagg ttgttttatc tttataaact  4020
gctgcagtgg acactgaggc cggttttttt ctttgttttt ttttttttgt ttgtttgttt  4080
ttgagacaga gtcttgctct gtcacccagg ctggagtgca gtggcgcgat ctcggctcac  4140
tgcaaactcc gcctcccggg ttcacaccat tctcctgcct cagcctcccg agtagcttgg  4200
gactataggt gcgtgccacc atgcctggct aattttttgt atttttagta gagacggggt  4260
ttcaccgtgt tagccaggat ggtctcgatc tcctgacctc atgatctgcc cgcctcggcc  4320
tcccaaagtg ctgggattac aggcgtgagc cactgtgcct ggccactgag gccagtcttt  4380
gcccggatcc tcactgtgtt cctaggatga ggttctggga ggggaattgc tggtcagagg  4440
tcgagcctgc ttttgaagct tcttctacca ggagtggagc tgagcaggtt tgataaggtc  4500
tgaagatttg ggggtggaaa tgccaggtcc cttgagagac atgagggata agagggggcc  4560
aggctggcct tgagtgccag agtgcagagc tgggctagat gtgaggacag tcgggggtca  4620
gagcaggggc acaccgagct tcagttccct ctggctgctt ggatggagga tcgtaatgtg  4680
aacagaaaac actaattgag tacttactgt gtttcagaca gtgtgttgat aatcccactt  4740
aatcccctga caaccccaag taggtagaca tatgatgaag atgacggcct tgaggaccag  4800
agaggttaag tgatttgcct gagatcacac agccagatga tggcaaagcc agaattcaaa  4860
cccaggctgt gggctccaga gcctagctct taagctctta agcactgggc tcctaagaat  4920
ggggatgagg ggttgaggga ggctcctcca caggggctac tctgggggcc tggaagtggg  4980
```

-continued

```
tcacagaggg gtcagaggct atgtggctac ctccccatcc cagtccagag cagtgtttga  5040
gtcattagac tgggaaccag ccctggtgag ccagccaagg gccttgggcc ccatccggtc  5100
ctgctgcctg ccacagccaa actcttgtca tgtgaatgga tttggggatg gagctgcctc  5160
catgagtcct tgcatctgtg ggtgaaggca ctgccctggc tatagtgtcc ctgggtttga  5220
gtcctgcatc tgcaccaaga cctcaggtga gcctgtctcc ttctgggcct cagagtacct  5280
tgcagctgtc gggggaggat ggatcaggag atggccctgt acctgtgttg gggattattg  5340
ttaagcccgt ggcagtcttc acctccctgc tgaggattaa tttatccaat tttgcacaag  5400
cttatgagtg cagaagaggc agacggaaac agagttctgg ccaagagcct ggaacagggc  5460
ctcggggtct ctttcctatg cctggacccc gtcatgtctg ctctttgtct gtcggacccc  5520
agatgtctgc caagccccgt cagaggctgc ttcccagaaa gcccttctgg gtgtcacctt  5580
gccccgagca gtgcgttctc agagttctcc cgccctgatg tccctcccag catgcccagc  5640
ccagccacaa cagggccttg cttctagtca tgtgtctggc tgtttgctgg gtccaggcca  5700
gccctggtag ggcacaatgg gggcccgctc tgccacccca tacctctccc caggatatct  5760
catgccccag ttctctccct agttccacca agcactggca ctccttagaa aacacagctc  5820
tagactagtt actgccctag cttacagcac agaactcccc tggtctccaa ccattcatgg  5880
ctccctagtg ctccaagata aagttccctt gtctcagccg ggttgggagt taccttctgc  5940
ccaacattca cctagctgga cacaaacatc ctgagtgacc cggtcagctc caggcaggag  6000
tcactgccag cagaggcctg ggatctggac tttgcctgct gacaggtgga gcccaggccg  6060
gccagaggaa gtgcctctga ccttgtctcc tagcagccac gggccatgtg gacatgcctt  6120
ttgaccctgg gcactgacag tgtgtgacag cctgcaccat gtgctccaca ggggcggctg  6180
tgtgtgtcgg gggtgaggtg gggaaagcct taactggctc aggggtgaga ggtcagggag  6240
ccattgagac tggctccagg tgtgggtccc ctgctgggtt ggggcttgtg ggaggtggga  6300
cggggctggg ggtccatccc cctaggggga atttgtggcc taccccgaac cctgtttgag  6360
ctcctttcct aactgactcc ccgtccctgc acctgtctcc cagcaggcct tgcctctgca  6420
tgctgcccct gccaggctct ggggtccctg tgctccctgc agctagaagg ctgggatcag  6480
gggtcttaac aagcagccct actgtatgac cttggacaag tccaagaacc ttcaggttct  6540
taacaatgta aagggagcag tactaaaagc agcttcttgg aattgtgggg atccgatgag  6600
tgaaggctta agcagtgcat ggcacatagt aggccctgaa ccaatgccag ttagtgttat  6660
tattatcacc atttagccag atgcagtggc tcacgcctat aatcttattg actttagagg  6720
ctgaggttgg aggattgctt gagaccagga gttcaagacc agcctgggca acatagcaag  6780
gccctgtttg ttttagagaa aacaaacaaa tcaccattta gagcacctaa ccagtacctg  6840
gcacgcgata ggtttagctc aacaaatgtt agcagcaatt acccaaggag cctgtgctgg  6900
aagtttctag gatgtaccag gctatggttc caagttctga gcatctacca tgtggtggtc  6960
tggagttggt gagagacagg atggggctga ctaggccagt ggggagcacc ccccgccatg  7020
gggaacaagc accctatcct tggcttccat ggaagataat tgatgctggg cacagtggct  7080
cacgcctgta atcccagcac tttgggaggc tgaggcaggg ggatcgcttg agtctgggag  7140
ttcaagacca gcctgggcaa cattgtgaga cccaaactaa aaaaattagc ttggcatggt  7200
ggagtgtgcc tgtcgtccca gctactcagg aggctgaggc taaagctgga ggattgcttg  7260
agcccaggag gttgaggctg cagtgagcca tgatcatacc actacactcc agcctgggca  7320
acatagtgag gccctgtctc aaaacaaaca aacaaaaaga acctgctgag gaagcagtgt  7380
ttctggctgg gggaggacgg gcagagtggc catctggcca cagatggcgg tttctgtgca  7440
aaacacatca aggcagcctt ggaaatgtga gtgaaagcac cttcaaagtt ctggtcacag  7500
ccttgggact aagcaaagcc accaaaagta cataaaagac aatgaccatc acccagtgcc  7560
ggtgatgcta gaaggaaagg gaatacgttg tagggaaggt tgtaaagggc tttatctttt  7620
ccagactgga gcctggcagc tcgaaaacat cttgctgcct tcatatgagc tttaaaacaa  7680
gctgcagaga aacaactcaa gagggagaaa tatatatata tatgtgtgtg tgtgtgtatg  7740
tgtgagtgtg tgtgtgtgtg tgtatacata tatatatata tatatatata tatatatttt  7800
tttttttttt taagatggag tctcgttctg tcaccaggct ggagtgcagt ggtacaatct  7860
cggctcactg caacctccgc ctcctgggtt caaatgattc tcctgcgtca gcctcccaag  7920
cagctgggac tataggcaca taccaccacg cccagctaat ttttgtattt ttagtagagg  7980
ctggatttca ccatgttggc caggatggtt ttgatctcct gacctcgtga tctgcctgcc  8040
ttagcctccc aaagtgttgg gattacaggc gtgagccagt ttgtttttag agacggggtc  8100
ttgctctgtc acccaggctg gaataccatg gcacaatcac agctcgctgc aatgttgaac  8160
tcccgggttc aagggatcct cccacctcag cctccagagt aatggagact acaggctcat  8220
gccaccatgc ccagctattt ttaaaacttt gtagagatgg ggccttgcta cattgcccag  8280
gctggtcttg aactcctggg ctcaagtgat ctgcctgcct ttgcctccca aagtgctgtt  8340
attacaggtg tgagcccctg cgcctaacct tagcactgcc attttgactg aaaacaggtg  8400
cccagcagca ggggctactc ccagaattgc cactgcatca ggcccgtggg ttgttttcag  8460
ctgccagtga taagtatgtg ccctgggcca cctctcggac aaggtgtctg aattggtgcc  8520
gaccagcatc acatgtaatt gccatctcgc aggtgctgct gagggtaatt ccgcacacct  8580
gtagctccgg gaagagccta gtggggagga ggaaacgtgg ctctgaggtt tatagggtca  8640
gacggtcagt atgttgggag ctggcatgtg gaggggcaca gacaagggaa gaatgggagg  8700
tggcatcaga gcaagttttg atggaggaat aggaattcac caggtggaaa gggcattcct  8760
ggtggaggga acagcctggc cttcaatagc ttgtggtgtt cagaaagcag gcagggaaag  8820
ggaggcccag ggagacacca gttaggggat gggggtggag gcagacgagg gtggaggaag  8880
ccatggctgg agtctgcacg gcctctgact ggggtccctg ctgtggtcag ccctgtgctg  8940
ggtgaggctg gggtcacagc tggttcaggc cctgacagga ggggccccca gctgaggccc  9000
agcctctaat ttggcagggc aggtggatag gtctgggggg gtggtggtta ggaagcctcc  9060
aggaggaggc agtgccggag ctgagcctta aagagcttcg tgttgtcctc tctgtctttg  9120
cactctgcac acactcactg aactgcgaca aatgaggata gctggtcagg gcagaggcag  9180
gccggagttg gggctcactg ctgtccccca caggctgggg ctgaagggca ggctctgggg  9240
ccgcagaatg gggtttgtgt accagattct tcatatggca gctgtgggac tttgggcacg  9300
aggcctccgt ctgagcctta gtttcctcaa gaggacctgc gcccaggtgc acctggggct  9360
ccagccatgg gtgcgtccca ttccgggaag agctggcaca cacttgtgcc cccggggcag  9420
ccatgagtgc acaaagggca gcctgtgcca ctgctggata cacgaccagc tgagaacacg  9480
aggaccgccg actccagtta ggaggatcaa ggaagtgcct ggtgggagca gaacagcagg  9540
tggggtgcag cccagctccc tggagggatg gtgggcaccc atcctcaccc tgctgcctcc  9600
attagcaggc cgagagggtg tgctctggaa tcccatgagc acctgtgcca catcctcccc  9660
tgtggctgac ccttcttcac agttggtgca gctttgtggt ctgtagtgca gggatcaatt  9720
```

-continued

```
ggcaaatccc tttcccaccc attccctgga gaattggggt ccttggctca gatgacagac  9780
caacctgagt tggaatccca gctccttggt ggccgtcctg gcctccaccc cctcactgcc  9840
tccgctcctc ctatcctgcc cacgcccact gcagggcctt tgcacacact gtttcttctg  9900
ccctcccttc cggcccactc cctcatatca ttcagtcctc ctttcagatg tcacctccta  9960
agatgggctg ccctgaccac ctcatctata atggccccag tgcctggcac aggattggca  10020
cacagtagat attgtcagag atggatctgg gttctgtgga caaggctgtg ggggcaggtg  10080
aagagctccc tcttccagga ggttgtttgg ggttcaaggc cttgtttggg ttgtaggctt  10140
ctgtgctggt cagcgttggg ccctacaagc gcatgccatg aggcctgccc aggatttccc  10200
tcatggcctc acagaataca tcggccagag tcattaaagg gcgcctgcat ctgccttcag  10260
agagaggttt gaaggtagaa ctggggaggg atgccaggtg ggggttcagg tttcctgttg  10320
ggtcctgata gaatcagggc aggagaggaa gaagaagagg gaagaggagg aacccaggct  10380
tggggagggg tggcagggct tcacaagcct ggggaaggtg aactagggag cagttggggc  10440
caccatggcc cagagtctat gcctcctctt ccttcctgtg ttcagagtgt gtgtgggaac  10500
cacaagggcc ttctcagtgt tcataggaa gcccggttca cccatgggtg ggccgcaatt  10560
tgggtgccac agtgagcccc tagagaccag ctctcccagc ttccaggaca gggactaggg  10620
gaggcaagag aggctcttcc ttaaattgtg cacccaaggt gcctcagctg ccttactcta  10680
gactggcccc gttaactccc cttaaaaaaa aaaaaaaaaa gactcagtcg aatggtaatg  10740
gagctccaac gtgaatactg caagtatcag gcaactcact acctgacttt ccagttctaa  10800
accattctaa ttgctgtaga gagaactaac ctttgttgag actgttgagt gatggatgtt  10860
ttacacactt gctttcccag aattcccacc tctggagatc gtaggtgtgg gagctcagag  10920
ggtggggagt ggactgtccc catcacacag caagggaggg gctaaaggaa gagcagggcc  10980
tggcatgcag ccccagatag cccacttggg tgtgtctctg agggaggctg cagggctggc  11040
tctagagttt cctttttcag tcttaacctg gtgaccagct tccacagaaa ttggcacggt  11100
gactcatgcc tgtaatcgca acacattggg aggccgaggt gggaggatca cctgaggtca  11160
ggagttcgag accagcctgg ccaacgtggt gaaaccctgt ctctactaaa aatacaaaaa  11220
ttacatttca ttacaggtgt ggtggcgcac acctgtaatc ccagctactc aggaggctga  11280
ggcaggagag tcacttgaac ccgggaggta gaggttgcag tgagctgaga tcgtgtcact  11340
gcactccagc ctgggtgaca gagccagact ctgtctcaaa aaaaaaaaaa aaaaaaaaag  11400
aaattggcca gtagatcagc cccaggggag agtgagccag ggtttggcca ggccttgagt  11460
ttcagaggct ggccatggcc agtggcaccc aggcccttcc cccttcctcg gggcatctta  11520
gcttagtctg tgccctctgc ccaagggcca gccctctgtt cccaggtcac accccctcct  11580
cttggaaggc ccccccgcc ccacccccat cagagtcttt aatgactctg ctgcccctgg  11640
ggctcagaga gcaaccgccc tctcccatcg cgcttcctca gtgggatggg agggggttag  11700
agcaggaaga tgagacaaat aaagacacaa taagaggcag gaatatgtgg taaagccaag  11760
atgggtaagg ggaggggaca ggcttgactg ttcacagtgg ccctggccct gctgtctcag  11820
gctagtatct gcttgttggt ctcaccacat tctaggctca gaaactgggg agcaaagtaa  11880
tgaaagaacc aggctgggag gccatgggga actcatgcct ggagttcagc tctcagtgtg  11940
cttttgggtc aaggacgctt ccctgtctta agtcactcat gtcagagcct ttgccaagag  12000
caatgctgtg ttttgttttg ggggtgaggg aacacccgcg ggctgagggg agggttgggc  12060
catgctagag aggccgtctg ttgtccttga acctcccaaa gctgggaaat aagggcctgg  12120
gctggacggc ggtggcgagg acaggttgcg agagagacat ggctgggttt tcttgcttag  12180
ggtcctgaat agagagcaag gttgaggccg cagggacccc agcccccaat ggactgctga  12240
gtcgctgggt ctgcccaggg ttcaggcacc ctctcaggtt gcagccaact ggggtgtgga  12300
ccaggcagag gcgctggcct gcagtttggg gcagaggcag gctttgctgg tggtctactt  12360
ggctgcaaaa tcaactggcc aggctctgat cactttgtgt gtgtgtgtgt gtgtaacttt  12420
tacctttgac aaaagaggga agacaggccc aggcacctcc tcaaaagaac cctagagcct  12480
gtcacccctt ccttacccat cttctgtcct agggactgca gcccttcctg gcttcccagg  12540
gccctacaat gaatagtggg tcgggactca cttggtgact gctgggttgt gaggccttga  12600
gggggagggg cagacttcac ccatctggca gagggacatc ggtgctggca gtcaggaaac  12660
ccttatttcc aggcctcagt ttcccggaag tgacctgttt tcaggagtgg cctcatccca  12720
gaccatcagc cccgctgtgg tgaggggtgg ccccttcctg gggctgccct agaaggggga  12780
ggtccctgca cccaccgcag ctgccactcg gcagcccttg gccttaatta aacgcttctt  12840
gcgtactaag tgctgcaccc atattatctc ccttctacca ttcgacgcca gggagataat  12900
gactgtcctg ttttctggag gagtaaacgg agggttggag cggttaaggc tcgctcaggg  12960
tgccagcgaa ccagtgattt cgaacacaga gttctggtgt gttgggccag gacttctctg  13020
ctttgaccct ttaacgaagg gggcgggagc tgagggccag tgaccgccag taacccccggc  13080
agacgctggc accgagcggg ttaaaggcgg acgtccgcta gtaaccccaa ccccattcag  13140
cgccgcgggg tgaaactcga gcccccgccg ccgtggggag gtggggcggg ggccggggcc  13200
gggccctagc gaggcggcag cgcggccgct gattggccgc gcgcgctcac cccatgcccg  13260
gcccgcagcc ccgaagggcg gggcggggcg ggacctgcag gcggggcggg gctggggcgg  13320
ggctggggc ggggcggggc ggggcgggcg cgccgcagcg ctcaacggct tcaaaaatcc  13380
gccgcgcctt gacaggtgaa gtcggcgcgg ggaggggtag ggccaacggc ctggacgccc  13440
caagggcggg cgcagatcgc ggagccatgg attgcacttt cgaaggtatt tttggaggcc  13500
tccccaccag ccctttatac aatgcctccg tctcctgcag gttctcctgg ggtgggcggg  13560
catgcgggct acgcaacttg agcaggaaag agccccttcc cgagggagaa ggtgtgacag  13620
ttaccagctc gctggggaag tggagggcta cctccaacca aattagtgtc ccctgcaact  13680
caagggggaa gggtttgctt agagacccaa aagcagcatc ccgacctaag agggtttgga  13740
gggagagggt ggtcttctct acattctctg cacccgcttt gggacaggac caggaggaag  13800
cagggaggag ggcccgttgt ccctctgcca cagcgtctgc cctattcagc acccctgcct  13860
attgtgggca tcttagactt ttcaggaaga cagtgggagc cctagattgt caaaattgtc  13920
agtttttctt tcaggcctca gtttccccca tctatcgaag aggctcacac ggactggggt  13980
aaagggatgg gaaaccctgc agttgaaagt ccattatgac ttgatgactt gtgacctggg  14040
gggtccacaa accaggagag tttctacttg agaagccagg aagactgggg ctgccacccc  14100
atcctgttct gccaactgct ctaggaaatt cccctcctgc agtagcttcc ctgcctgggt  14160
acctgtcagt aggcaatgtt gggtctccac tcggtgccag ctgcctgcca agcaaagcct  14220
cgggcagccg taccaaaagg ggtttagtct tttctgttgt acagatgagg aaactggggc  14280
cagtgagagg aggctgttgg tccaggctcc acttcaagct ggtggtgggc agggctggga  14340
gctcaggctg gggatcctga gagcactgga ggccccccatg ggtcctgtag agcattctga  14400
cccagtgggt gccaccacga gtgggttaga gggccctggg ctgagccaga taggctgcta  14460
```

```
gtcaccagct gggggagagg gcccttggcc aggtggggct gaggtgggag tgtgtcccag  14520
tctgtatgag gaggaaggag tcaggacaga cagcacttgc ttttacagag atgaaatcaa  14580
agccctgagt ggccaggcct gggtcttgag gctacttggc tgcaggcaaa gcctggactt  14640
gagcccagaa ctctacacag agacacactg gttggccatg tggccagcag ctggcttggc  14700
cctaagcctt ggtctgttcc actgagtaat gggttggtga tggcagcctg gctcttggct  14760
tcttagtggg gcaagaaaag gcagagagac aatagatttg ggattttgta gacctgggtt  14820
tgaaccccac tgcatgctct tgggctgctt gtggtcctcc ctgagcctca gtgtcttttc  14880
ttgtctccaa gatgaggtga gctaatcttt tgaggtagtc tagggtagtg gccagtggtt  14940
ggggcattgg agtcaaaata gggtctggac tcagttgagt ctctgactct ataagaactt  15000
aggccagtaa gtcacctctc tacagctcag tttcttcacg tgtagaatgg ggccaatgat  15060
cacatcaccc tctcagctgt gggtgaggat taggggtcta gcctggcccc atcaatgtgg  15120
gtagccccac agcgggcctg gcttttggac cagacccacc cttctgacat gggcccccac  15180
ccttagagtc cttctagtgt ggatgaggac cctgctctga tctggggtcc tcttggggga  15240
cttccctgtc tgccattctc tttggggatc ctgcgctgcc ctaggaagag tgggcccagg  15300
ctgcacagtt ggtccttggt cacagaggat cccaccactt cttcagggcc tcaaggcaat  15360
cctgcctctc tctgcacccc tcttcccccct gtaaactgag gggaggggaa aatcacccac  15420
tcctcagcag tttctaagtt gctttgtcaa attcagtgcc cagaggatcc tgctgggggt  15480
gcgttttagg atgagaccag gagtggccaa tggtggggtg tggggcccat cgctcctata  15540
tgaagacccc ctctgcccta gactgctcct ccctccccat ccccatctcc atcccaaaga  15600
ctggagctgc tggatctgtg gatggaggcg tgccccccgt ttcacacatt gagaaacagg  15660
ccccaagtgg agccagggaa ggctgcacct gggcctctgg attccttttg ttctgtgtgg  15720
ggttgggggt gatggactgt ggagagggca ggagagctgt ctggaagggt tggtcacctc  15780
atgggcaaat gcttggaagc tggtctgagt ccacggtgca gtgtgtatgt gtgtgtgtgt  15840
gtgtgtgtgt atgtgtgtgg actcagaggt ggatgtcttg tagaatgcat gccccatgaa  15900
gacaggagta aaagtttacc accatccaca tcaagctaca ggacactccc agctccccag  15960
aaagttgctt agttctaggc agggatttcc cttattcaca gccgggagca gtgcctggca  16020
tagtgtgggc actcagcact cagcacatgc tcactggatg agtgaatgaa tgtgagcctg  16080
ctgtttgctg tggactaagg atgtttctag atgtttgggc aaataccgga tggtgggaag  16140
agctcaggct ctgaagtctg cagtcttggg cccgaccctg ggctcagccc cagcctagct  16200
gtggggcaag attgtgagcc ttgtggtgcc caccttgtcc aggtattgtg atgcactcgc  16260
agcagcaggc attgctttag acagcacagg tgctcgcaaa atggctgtat gtccgggaac  16320
accagctcct gtgggtggct ttctgtcctg gtggcattgc ccacacatac agctgtgtgc  16380
caacaagggt tgtgcaaata aggttgtgtt tggatgtgtg tgatgccctg tttggggggtc  16440
agtctctgcc tcactcacgc accctcttct ccttttcaca gacatgcttc agcttatcaa  16500
caaccaagac agtgacttcc ctggcctatt tgacccaccc tatgctggga gtggggcagg  16560
gggcacagac cctgccagcc ccgataccag ctccccaggc agcttgtctc cacctcctgc  16620
cacattgagc tcctctcttg aagccttcct gagcgggccg caggcagcgc cctcacccct  16680
gtcccctccc cagcctgcac ccactccatt gaagatgtac ccgtccatgc ccgctttctc  16740
ccctgggcct ggtatcaagg aagagtcagt gccactgagc atcctgcaga cccccaccccc  16800
acagcccctg ccaggggccc tcctgccaca gagcttccca gccccagccc caccgcagtt  16860
cagctccacc cctgtgttag gctaccccag ccctccggga ggcttctcta caggtaaggg  16920
ggatgtgtgg cgggagggga cacccggggt ggggcttcca ggagcacagg aagaagcttc  16980
tgctgtgatg tgagtagagg tctgtgcagg ctttagaaac tggggctcca ctcggctgct  17040
tgagatgccc tgttactagc agtcctggtg tgcttgttgc cggggtaggc gcaacctcgc  17100
actggaggcc tggcttgaag ccagtgcatt tgcatcagag cccaggcagg gactgtccat  17160
aggaagccac atggggcaat gactcatcca aggccagtcg gtgatagaga cctgaagagc  17220
aggttgaaag tgggagaggg aggtctgtgt ctgcagcccc atgctttatt tctgcaggaa  17280
gccctcccgg gaacacccag cagccgctgc ctggcctgcc actggcttcc ccgccagggg  17340
tcccgcccgt ctccttgcac acccaggtcc agagtgtggt cccccagcag ctactgacag  17400
tcacagctgc ccccacggca gcccctgtaa cgaccactgt gacctcgcag atccagcagg  17460
tcccggtgag gggtctggc caggggttgg ggaggggggca gccccagccc agacacacag  17520
cttacagcca agcctctccc accctcaggt cctgctgcag ccccacttca tcaaggcaga  17580
ctcgctgctt ctgacagcca tgaagacaga cggagccact gtgaaggcgg caggtctcag  17640
tcccctggtc tctggcacca ctgtgcagac agggcctttg ccggtgggtg acgtgggcag  17700
ggcataaggg agtggggtct acacacacac acacatgccc acctggtaac atgtgcctgg  17760
ccctgcagac cctggtgagt ggcggaacca tcttggcaac agtcccactg gtcgtagatg  17820
cggagaagct gcctatcaac cggctcgcag ctggcagcaa ggccccggcc tctgcccaga  17880
gccgtggaga gaagcgcaca gcccacaacg ccattgagaa gtgctaccgc tcctccatca  17940
atgacaaaat cattgagctc aaggatctgg tggtgggcac tgaggcaaag gtgtggagag  18000
gcctgcaggg gcacagaccg gggtgtccct aggaaggaac agatcagggg caactggaag  18060
gaagagaggg agtgagactg agcctggaca agcagggaat tggaattcag cctccccagg  18120
cctggccagc ctcgtttatt tagttaaact ggtttgcagg cctcttcaat aaaggtgggg  18180
ctgtgctagg cattggggat gcagcaatga acaagacaga caaaaattgt ccctcaaaga  18240
agagccgacc ttctggtggg ggagatggac agtaggcagg atgaataagt gctcgagacc  18300
accacgtttg gctcgttgca gagaaagcag gaagaggatg gtgagggtcc cctggtggta  18360
gccagggaag gcctccctga gatggcggca ggcacagcag cagctagcca gaccctgctg  18420
tctgcatctt acattctaac cctatgcccg gcctgggagg tgggtgctac taggcgagga  18480
acggttcagg tagaaggaac aagtgcaaag gtcctgaggc agtaatgttg caaagcagct  18540
ccgcaccccc ttgctagggc tctccaaccc cacaaccccc gacctgacag gccacctgtg  18600
cgctccccct ccctcccaca ccgtgcagct gaataaatct gctgtcttgc gcaaggccat  18660
cgactacatt cgctttctgc aacacagcaa ccagaaactc aagcaggaga acctaagtct  18720
gcgcactgct gtccacaaaa gcagtgagtc ctggctttat tgagctccag tctggcctct  18780
tctctagcct tgctccacct cccggcccca ccccatccct agccccaccc cacccttggt  18840
tctggcccac cctctgccct gcccacctca cccttggctg tagccctgca ttcagctcta  18900
gtcccttggt tacctctggt cctgaaagag acctggtgcc tccctttggc cctaacccag  18960
ccccatcaaa gcgtcctggg ctagctttag gagctacagt agtccctagg cctccaaggg  19020
cctaggctct gatttggggt cacatatcca gcctttactc ctggctctgt tcctttcggc  19080
ccacagaatc tctgaaggat ctggtgtcgg cctgtggcag tggagggaac acagacgtgc  19140
tcatggaggg cgtgaagact gaggtggagg acacactgac cccacccccc tcggatgctg  19200
```

```
gctcaccttt ccagagcagc cccttgtccc ttggcagcag gggcagtggc agcggtggca  19260
gtggcagtga ctcggagcct gacagcccag tctttgagga cagcaaggtt gggccctgcc  19320
acggtgcccc cttccccact cccagccata tcctctgagc ctcatgacag ggccgggaag  19380
accctaacag atcctacctc ccatttcata gacagaataa ctgaggcctg gagccacgtg  19440
gggtcccaca gtaaggtggg cagaatcctg accccccccct tcccagcccc atgctctctg  19500
gggtccctcc gattctgccc tcaccaccct gcccaacccc accaggcaaa gccagagcag  19560
cggccgtctc tgcacagccg gggcatgctg gaccgctccc gcctggccct gtgcacgctc  19620
gtcttcctct gcctgtcctg caacccccttg gcctccttgc tgggggcccg ggggcttccc  19680
agcccctcag ataccaccag cgtctaccat agccctgggc gcaacgtgct gggcaccgag  19740
agcagaggtg ggaccggcca gcctgggcat ctttgggagg gacactcggg gtgagccccc  19800
aggcttgtga acttggggct ctggatttcc tgggagctgt gtccccagct ttccctctgt  19860
ccatagatgg ccctggctgg gcccagtggc tgctgccccc agtggtctgg ctgctcaatg  19920
ggctgttggt gctcgtctcc ttggtgcttc tctttgtcta cggtgagcca gtcacacggc  19980
cccactcagg ccccgccgtg tacttctgga ggcatcgcaa gcaggctgac ctggacctgg  20040
cccgggtaag gggctggccc cggcagagtg ggcagggcag ggaccccagg ctgtgaaggt  20100
gctgggtgtc aacccttgtt cctgctccct gtgcacacca tgaatctgtc ccgtcctccc  20160
tgtgcctagc cacgcatccg cagaccccca ccacccctcc agagcctgct gtggacggct  20220
cttctgagct tggggcagc tgctctgacc tcacttttct cacctggaaa accctcatcc  20280
acagggagac tttgcccagg ctgcccagca gctgtggctg gccctgcggg cactgggccg  20340
gcccctgccc acctcccacc tggacctggc ttgtagcctc ctctggaacc tcatccgtca  20400
cctgctgcag cgtctctggg tggccgctg gctggcaggc cgggcagggg gcctgcagca  20460
ggactgtgct ctgcgagtgg atgctagcgc cagcgcccga gacgcagccc tggtctacca  20520
taagctgcac cagctgcaca ccatgggtag gactgagcgt ggggcgggct ccgaggtgct  20580
ccctgctgcc tgtgctccac ccacagcctc atgcctgctt gccttccagg gaagcacaca  20640
ggcgggcacc tcactgccac caacctggcg ctgagtgccc tgaacctggc agagtgtgca  20700
ggggatgccg tgtctgtggc gacgctggcc gagatctatg tggcggctgc attgagagtg  20760
aagaccagtc tcccacgggc cttgcatttt ctgacagtga gtgggttggg gggctggggg  20820
cttatccctg cagctctctc cagaggctcc ctgggtaaga gctacacggg atgtggcagt  20880
ggttaccagg gggactccag gccaagctgg gactcggccc ggggtctggc cccaggctgt  20940
gtccactgtg acagcccagt accctcccct acagcgcttc ttcctgagca gtgcccgcca  21000
ggcctgcctg gcacagagtg gctcagtgcc tcctgccatg cagtggctct gccaccccgt  21060
gggccaccgt ttcttcgtgg atggggactg gtccgtgctc agtaccccat gggagagcct  21120
gtacagcttg gccgggaacc caggtgctct cttacccctt ccctgtcccc tctcctgtcc  21180
ctcatcctca ttcctgtcct gtcccttgtc gcctgaatct ctggctgtct ctggccaccc  21240
cagtccttct ccctgccatg ggttgttgct gtgggggttg caggaaggga aaggcctggg  21300
tgcctctcgt tcccattggg gctttcagaa gcacatgcag ggattgatgg gcagatggct  21360
aattggagaa gtgaccccag gcagtgccgc tgtggagtaa ggaagcggag ccaacaatgg  21420
catcttctca agtcggtttt cctttggaag cagtgtaggg caggcctcag tgttgtctcc  21480
tggccaaggc tggtgctggt gatagttatg tccacccgct ttcccctgtc cttggcaggg  21540
gctgcaccca ggggcatgcc ggcacttccc agtggcccta ggtgtggccc cagcccaccc  21600
aggaaaaagc ccttagcttg gagaggaggg tggggccctg ctccccaccc cactcacctc  21660
ctcctctcca cagtggaccc cctggcccag gtgactcagc tattccggga acatctctta  21720
gagcgagcac tgaactgtgt gacccagccc aaccccagcc ctgggtcagc tgatggggac  21780
aagtaagtgt cgttgtgccc tcctccaggc aaggcccctc cggcgggatt ctgagaatag  21840
ctctggcctc aaccctgtgg agagagccca gagctgggct accgtgcgtg ccatgcacgc  21900
ttcattcctc tctgagtttc ctctccccac cagcctgtgg gaggagacag tggcactttg  21960
cagagccagg ggccaggctg tactctggag ggcaggtggg gagcaccctc ctaggacccc  22020
tgccatctgt tccgacagcc agctctctcc ttccacaggg aattctcgga tgccctcggg  22080
tacctgcagc tgctgaacag ctgttctgat gctgcggggg ctcctgccta cagcttctcc  22140
atcagttcca gcatggccac caccaccggt gagtccccgg cccctgtcct ggctcccttc  22200
tcagctcccc cgtgcagcgt gactgagggt tcaggggacc ctccctcttc tgcaggcgta  22260
gacccggtgg ccaagtggtg ggcctctctg acagctgtgg tgatccactg gctgcggcgg  22320
gatgaggagg cggctgagcg gctgtgcccg ctggtggagc acctgccccg ggtgctgcag  22380
gagtctgagt gagtgcacgg caggttcctc ctgcctggtc ccgggctcag ccttcctcat  22440
cccctgggca ctgtgcctca ctcagccttt gttctgtgca ggaggagtca ccaccttttt  22500
tcctcaggga actcgagcca gggaagtggg gggcactcag ccagggcttg tggactggtc  22560
tgactggcac tcttctgccc tggtcccaac aggagaccc tgcccagggc agctctgcac  22620
tccttcaagg ctgcccgggc cctgctgggc tgtgccaagg cagagtctgg tccagccagc  22680
ctgaccatct gtgagaaggc cagtgggtac ctgcaggaca gcctggctac cacaccagcc  22740
agcagctcca ttgacaaggt gaggggtggg gtcaggggcc tggcagggct gggggattca  22800
gctttccatt ccctggttcc tctccccagc ccccaggggc tgcagaagac catggggtta  22860
gcccaagcag cacaggatag ggggtccagc agaccctgct tttggctaa ggcttctgtc  22920
cagaggagag gggttgcccc tatctggcct cagtttcccc atccctggga ggagggggt  22980
ggatggtgtg gtaggatccc tttggaggcc ctgcatcagg agggctggac agctgctccc  23040
gggccggtgg cgggtgtggg ggccgagaga ggcgggcggc cccgcggtgc attgctgttg  23100
cattgcacgt gtgtgaggcg ggtgcagtgc ctcggcagtg cagcccggag ccggcccctg  23160
gcaccacggg cccccatcct gcccctccca gagctggagc cctggtgacc cctgccctgc  23220
ctgccacccc caggccgtgc agctgttcct gtgtgacctg cttcttgtgg tgcgcaccag  23280
cctgtggcgg cagcagcagc ccccggcccc ggccccagca gcccagggca ccagcagcag  23340
gccccaggct tccgcccttg agctgcgtgg cttccaacgg gacctgagca gcctgaggcg  23400
gctggcacag agcttccggc ccgccatgcg gagggtgagt gcccgatggc cctgtcctca  23460
agacggggag tcaggcagtg gtggagatgg agagccctga gcctccactc tcctggcccc  23520
caggtgttcc tacatgaggc cacggcccgg ctgatggcgg gggccagccc cacacggaca  23580
caccagctcc tcgaccgcag tctgaggcgg cgggcaggcc ccggtggcaa aggaggtgag  23640
ggggcagctg ctgaccaggg atgtgctgtc tgctcagcag ggaagggcgc acatgggatg  23700
tgataccaag ggaggctgtg tgtgtgtcag acgggacaga caggcctggc gcagtggctc  23760
acacctagca ctttgggagg ctcagttggg aggacagctt gagcccagga gttggaggcc  23820
gcagtgagcc tgagtgacag ggagagtccc tgtctcaaaa aaaaaaaaag accaagcatc  23880
ttcttgatgg ttacctgatg acaattcctt tcacaaggaa tcagtggggt gactgtcatt  23940
```

-continued

```
tgtgggatac atgactgcac gtgcgtgact cagtctgtgg actttgtgtg tgggctgaga  24000
ctagggtggg gagaggggaa cccgccaggc ccccgccagg tacctgtgtg ccaggtacag  24060
gcggctggtg ccgtggcttg tgtgtgggca gggctcccgc gggggcgtgg ccagcttgag  24120
acccatccct gacacatcct cgtgtgcgca ggcgcggtgg cggagctgga gccgcggccc  24180
acgcggcggg agcacgcgga ggccttgctg ctggcctcct gctacctgcc ccccggcttc  24240
ctgtcggcgc ccgggcagcg cgtgggcatg ctggctgagg cggcgcgcac actcgagaag  24300
cttggcgatc gccggctgct gcacgactgt cagcagatgc tcatgcgcct gggcggtggg  24360
accactgtca cttccagcta gaccccgtgt ccccggcctc agcacccctg tctctagcca  24420
ctttggtccc gtgcagcttc tgtcctgcgt cgaagctttg aaggccgaag gcagtgcaag  24480
agactctggc ctccacagtt cgacctgcgg ctgctgtgtg ccttcgcggt ggaaggcccg  24540
aggggcgcga tcttgaccct aagaccggcg gccatgatgg tgctgacctc tggtggccga  24600
tcggggcact gcaggggccg agccattttg gggggccccc ctccttgctc tgcaggcacc  24660
ttagtggctt ttttcctcct gtgtacaggg aagagagggg tacatttccc tgtgctgacg  24720
gaagccaact tggctttccc ggactgcaag cagggctctg ccccagaggc ctctctctcc  24780
gtcgtgggag agagacgtgt acatagtgta ggtcagcgtg cttagcctcc tgacctgagg  24840
ctcctgtgct actttgcctt ttgcaaactt tattttcata gattgagaag ttttgtacag  24900
agaattaaaa atgaaattat ttataatctg                                  24930

SEQ ID NO: 3           moltype = RNA  length = 4178
FEATURE                Location/Qualifiers
source                 1..4178
                       mol_type = mRNA
                       organism = Homo sapiens
SEQUENCE: 3
gcggccgggg gaacccagtt tccgaggaac ttttcgccgg cgccgggccg cctctgaggc  60
cagggcagga cacgaacgcg cggagcggcg gcggcgactg agagccgggg ccgcggcggc  120
gctccctagg aagggccgta cgaggcggcg ggcccggcgg gcctcccgga ggaggcggct  180
gcgccatgga cgagccaccc ttcagcgagg cggctttgga gcaggcgctg ggcgagccgt  240
gcgatctgga cgcggcgctg ctgaccgaca tcgaagacat gcttcagctt atcaacaacc  300
aagacagtga cttccctggc ctatttgacc caccctatgc tgggagtggg gcagggggca  360
cagaccctgc cagccccgat accagctccc caggcagctt gtctccacct cctgccacat  420
tgagctcctc tcttgaagcc ttcctgagcg ggccgcaggc agcgccctca cccctgtccc  480
ctccccagcc tgcacccact ccattgaaga tgtacccgtc catgcccgct ttctcccctg  540
ggcctggtat caaggaagag tcagtgccac tgagcatcct gcagaccccc accccacagc  600
ccctgccagg ggccctcctg ccacagagct tcccagcccc agccccaccg cagttcagct  660
ccacccctgt gttaggctac cccagccctc cgggaggctt ctctacagga agccctcccg  720
ggaacaccca gcagccgctg cctggcctgc cactggcttc cccgccaggg gtcccgcccg  780
tctccttgca cacccaggtc cagagtgtgg tcccccagca gctactgaca gtcacagctg  840
cccccacggc agcccctgta acgaccactg tgacctcgca gatccagcag gtcccggtcc  900
tgctgcagcc ccacttcatc aaggcagact cgctgcttct gacagccatg aagacagacg  960
gagccactgt gaaggcggca ggtctcagtc ccctggtctc tggcaccact gtgcagacag  1020
ggcctttgcc gaccctggtg agtggcggaa ccatcttggc aacagtccca ctggtcgtag  1080
atgcggagaa gctgcctatc aaccggctcg cagctggcag caaggccccg gcctctgccc  1140
agagccgtgg agagaagcgc acagcccaca acgccattga gaagcgctac cgctcctcca  1200
tcaatgacaa aatcattgag ctcaaggatc tggtggtggg cactgaggca aagctgaata  1260
aatctgctgt cttgcgcaag gccatcgact acattcgctt tctgcaacac agcaaccaga  1320
aactcaagca ggagaaccta agtctgcgca ctgctgtcca caaaagcaaa tctctgaagg  1380
atctggtgtc ggcctgtggc agtggaggga acacagacgt gctcatggag ggcgtgaaga  1440
ctgaggtgga ggacacactg accccacccc cctcggatgc tggctcacct ttccagagca  1500
gccccttgtc ccttggcagc aggggcagtg gcagcggtgg cagtggcagt gactcggagc  1560
ctgacagccc agtctttgag gacagcaagg caaagccaga gcagcggccg tctctgcaca  1620
gccggggcat gctggaccgc tcccgcctgg ccctgtgcac gctcgtcttc ctctgcctgt  1680
cctgcaaccc cttggcctcc ttgctggggg cccgggggct tcccagcccc tcagatacca  1740
ccagcgtcta ccatagccct gggcgcaacg tgctgggcac cgagagcaga gatggccctg  1800
gctgggccca gtggctgctg cccccagtgg tctggctgct caatgggctg ttggtgctcg  1860
tctccttggt gcttctcttt gtctacggtg agccagtcac acggccccac tcaggccccg  1920
ccgtgtactt ctggaggcat cgcaagcagg ctgacctgga cctggcccgg ggagactttg  1980
cccaggctgc ccagcagctg tggctggccc tgcgggcact gggccggccc ctgcccacct  2040
cccacctgga cctggcttgt agcctcctct ggaacctcat ccgtcacctg ctgcagcgtc  2100
tctgggtggg ccgctggctg gcaggccggg caggggggcct gcagcaggac tgtgctctgc  2160
gagtggatgc tagcgccagc gcccgagacg cagccctggt ctaccataag ctgcaccagc  2220
tgcacaccat ggggaagcac acaggcgggc acctcactgc caccaacctg gcgctgagtg  2280
ccctgaacct ggcagagtgt gcaggggatg ccgtgtctgt ggcgacgctg gccgagatct  2340
atgtggcggc tgcattgaga gtgaagacca gtctcccacg ggccttgcat tttctgacac  2400
gcttcttcct gagcagtgcc cgccaggcct gcctggcaca gagtggctca gtgcctcctg  2460
ccatgcagtg gctctgccac cccgtgggcc accgtttctt cgtggatggg gactggtccg  2520
tgctcagtac ccccatggga agcctgtaca gcttggccgg gaacccagtg gacccccctgg  2580
cccaggtgac tcagctattc cgggaacatc tcttagagcg agcactgaac tgtgtgaccc  2640
agcccaaccc cagccctggg tcagctgatg gggacaagga attctcggat gccctcgggt  2700
acctgcagct gctgaacagc tgttctgatg ctgcgggggc tcctgcctac agcttctcca  2760
tcagttccag catggccacc accaccggcg tagacccggt ggccaagtgg tgggcctctc  2820
tgacagctgt ggtgatccac tggctgcggc gggatgagga ggcggctgag cggctgtgcc  2880
cgctggtgga gcacctgccc cgggtgctgc aggagtctga gagacccctg cccagggcag  2940
ctctgcactc cttcaaggct gcccgggccc tgctgggctg tgccaaggca gagtctggtc  3000
cagccagcct gaccatctgt gagaaggcca gtgggtacct gcaggacagc ctggctacca  3060
caccagccag cagctccatt gacaaggccg tgcagctgtt cctgtgtgac ctgcttcttg  3120
tggtgcgcac cagcctgtgg cggcagcagc agcccccggc cccggcccca gcagcccagg  3180
gcaccagcag caggccccag gcttccgccc ttgagctgcg tggcttccaa cgggacctga  3240
gcagcctgag gcggctggca cagagcttcc ggcccgccat gcggagggtg ttcctacatg  3300
```

```
aggccacggc ccggctgatg gcgggggcca gccccacacg gacacaccag ctcctcgacc  3360
gcagtctgag gcggcgggca ggccccggtg gcaaaggagg cgcggtggcg gagctggagc  3420
cgcggcccac gcggcgggag cacgcggagg ccttgctgct ggcctcctgc tacctgcccc  3480
ccggcttcct gtcggcgccc gggcagcgcg tgggcatgct ggctgaggcg gcgcgcacac  3540
tcgagaagct tggcgatcgc cggctgctgc acgactgtca gcagatgctc atgcgcctgg  3600
gcggtgggac cactgtcact tccagctaga ccccgtgtcc ccggcctcag cacccctgtc  3660
tctagccact ttggtcccgt gcagcttctg tcctgcgtcg aagctttgaa ggccgaaggc  3720
agtgcaagag actctggcct ccacagttcg acctgcggct gctgtgtgcc ttcgcggtgg  3780
aaggcccgag gggcgcgatc ttgaccctaa gaccggcggc catgatggtg ctgacctctg  3840
gtggccgatc ggggcactgc aggggccgag ccattttggg gggcccccct ccttgctctg  3900
caggcacctt agtggctttt ttcctcctgt gtacagggaa gagaggggta catttccctg  3960
tgctgacgga agccaacttg gctttcccgg actgcaagca gggctctgcc ccagaggcct  4020
ctctctccgt cgtgggagag agacgtgtac atagtgtagg tcagcgtgct tagcctcctg  4080
acctgaggct cctgtgctac tttgcctttt gcaaacttta ttttcataga ttgagaagtt  4140
ttgtacagag aattaaaaat gaaattattt ataatctg                          4178

SEQ ID NO: 4            moltype = RNA  length = 4253
FEATURE                 Location/Qualifiers
source                  1..4253
                        mol_type = mRNA
                        organism = Homo sapiens
SEQUENCE: 4
cagtttccga ggaacttttc gccggcgccg ggccgcctct gaggccaggg caggacacga  60
acgcgcggag cggcggcggc gactgagagc cggggccgcg gcggcgctcc ctaggaaggg  120
ccgtacgagg cggcgggccc ggcgggcctc ccggaggagg cggctgcgcc atggacgagc  180
cacccttcag cgaggcggct ttggagcagg cgctgggcga gccgtgcgat ctggacgcgg  240
cgctgctgac cgacatcgaa ggtgaagtcg gcgcggggag gggtagggcc aacggcctgg  300
acgccccaag ggcgggcgca gatcgcggag ccatggattg cactttcgaa gacatgcttc  360
agcttatcaa caaccaagac agtgacttcc ctggcctatt tgacccaccc tatgctggga  420
gtggggcagg gggcacagac cctgccagcc ccgataccag ctccccaggc agcttgtctc  480
cacctcctgc cacattgagc tcctctcttg aagccttcct gagcgggccg caggcagcgc  540
cctcacccct gtcccctccc cagcctgcac ccactccatt gaagatgtac ccgtccatgc  600
ccgctttctc ccctgggcct ggtatcaagg aagagtcagt gccactgagc atcctgcaga  660
cccccacccc acagcccctg ccaggggccc tcctgccaca gagcttccca gccccagccc  720
caccgcagtt cagctccacc cctgtgttag gctaccccag ccctccggga ggcttctcta  780
caggaagccc tcccgggaac acccagcagc cgctgcctgg cctgccactg gcttccccgc  840
caggggtccc gcccgtctcc ttgcacaccc aggtccagag tgtggtcccc cagcagctac  900
tgacagtcac agctgccccc acggcagccc ctgtaacgac cactgtgacc tcgcagatcc  960
agcaggtccc ggtcctgctg cagccccact tcatcaaggc agactcgctg cttctgacag  1020
ccatgaagac agacggagcc actgtgaagg cggcaggtct cagtcccctg gtctctggca  1080
ccactgtgca gacagggcct ttgccgaccc tggtgagtgg cggaaccatc ttggcaacag  1140
tcccactggt cgtagatgcg gagaagctgc ctatcaaccg gctcgcagct ggcagcaagg  1200
ccccggcctc tgcccagagc cgtggagaga agcgcacagc ccacaacgcc attgagaagc  1260
gctaccgctc ctccatcaat gacaaaatca ttgagctcaa ggatctggtg gtgggcactg  1320
aggcaaagct gaataaatct gctgtcttgc gcaaggccat cgactacatt cgctttctgc  1380
aacacagcaa ccagaaactc aagcaggaga acctaagtct gcgcactgct gtccacaaaa  1440
gcaaatctct gaaggatctg gtgtcggcct gtggcagtgg agggaacaca gacgtgctca  1500
tggagggcgt gaagactgag gtggaggaca cactgacccc accccccctcg gatgctggct  1560
cacctttcca gagcagcccc ttgtcccttg gcagcagggg cagtggcagc ggtggcagtg  1620
gcagtgactc ggagcctgac agcccagtct ttgaggacag caaggcaaag ccagagcagc  1680
ggccgtctct gcacagccgg ggcatgctgg accgctcccg cctggccctg tgcacgctcg  1740
tcttcctctg cctgtcctgc aaccccttgg cctccttgct gggggcccgg gggcttccca  1800
gcccctcaga taccaccagc gtctaccata gccctgggcg caacgtgctg ggcaccgaga  1860
gcagagatgg ccctggctgg gcccagtggc tgctgccccc agtggtctgg ctgctcaatg  1920
ggctgttggt gctcgtctcc ttggtgcttc tctttgtcta cggtgagcca gtcacacggc  1980
cccactcagg ccccgccgtg tacttctgga ggcatcgcaa gcaggctgac ctggacctgg  2040
cccgggggaga ctttgcccag gctgcccagc agctgtggct ggccctgcgg gcactgggcc  2100
ggcccctgcc cacctcccac ctggacctgg cttgtagcct cctctggaac ctcatccgtc  2160
acctgctgca gcgtctctgg gtgggccgct ggctggcagg ccgggcaggg ggcctgcagc  2220
aggactgtgc tctgcgagtg gatgctagcg ccagcgcccg agacgcagcc ctggtctacc  2280
ataagctgca ccagctgcac accatgggga agcacacagg cgggcacctc actgccacca  2340
acctggcgct gagtgccctg aacctggcag agtgtgcagg ggatgccgtg tctgtggcga  2400
cgctggccga gatctatgtg gcggctgcat tgagagtgaa gaccagtctc ccacgggcct  2460
tgcattttct gacacgcttc ttcctgagca gtgcccgcca ggcctgcctg gcacagagtg  2520
gctcagtgcc tcctgccatg cagtggctct gccaccccgt gggccaccgt ttcttcgtgg  2580
atggggactg gtccgtgctc agtaccccat gggagagcct gtacagcttg gccgggaacc  2640
cagtggaccc cctggcccag gtgactcagc tattccggga acatctctta gagcgagcac  2700
tgaactgtgt gacccagccc aaccccagcc ctgggtcagc tgatggggac aaggaattct  2760
cggatgccct cgggtacctg cagctgctga acagctgttc tgatgctgcg ggggctcctg  2820
cctacagctt ctccatcagt tccagcatgg ccaccaccac cggcgtagac ccggtggcca  2880
agtggtgggc ctctctgaca gctgtggtga tccactggct gcggcgggat gaggaggcgg  2940
ctgagcggct gtgcccgctg gtggagcacc tgccccgggt gctgcaggag tctgagagac  3000
ccctgcccag ggcagctctg cactccttca aggctgcccg ggccctgctg ggctgtgcca  3060
aggcagagtc tggtccagcc agcctgacca tctgtgagaa ggccagtggg tacctgcagg  3120
acagcctggc taccacacca gccagcagct ccattgacaa ggccgtgcag ctgttcctgt  3180
gtgacctgct tcttgtggtg cgcaccagcc tgtggcggca gcagcagccc ccggccccgg  3240
ccccagcagc ccagggcacc agcagcaggc cccaggcttc cgcccttgag ctgcgtggct  3300
tccaacggga cctgagcagc ctgaggcggc tggcacagag cttccggccc gccatgcgga  3360
gggtgttcct acatgaggcc acggcccggc tgatggcggg ggccagcccc acacggacac  3420
```

```
accagctcct cgaccgcagt ctgaggcggc gggcaggccc cggtggcaaa ggaggcgcgg  3480
tggcggagct ggagccgcgg cccacgcggc gggagcacgc ggaggccttg ctgctggcct  3540
cctgctacct gccccccggc ttcctgtcgg cgcccgggca gcgcgtgggc atgctggctg  3600
aggcggcgcg cacactcgag aagcttggcg atcgccggct gctgcacgac tgtcagcaga  3660
tgctcatgcg cctgggcggt gggaccactg tcacttccag ctagaccccg tgtccccggc  3720
ctcagcaccc ctgtctctag ccactttggt cccgtgcagc ttctgtcctg cgtcgaagct  3780
ttgaaggccg aaggcagtgc aagagactct ggcctccaca gttcgacctg cggctgctgt  3840
gtgccttcgc ggtggaaggc ccgaggggcg cgatcttgac cctaagaccg gcggccatga  3900
tggtgctgac ctctggtggc cgatcggggc actgcagggg ccgagccatt ttggggggcc  3960
cccctccttg ctctgcaggc accttagtgg ctttttttcct cctgtgtaca gggaagagag  4020
gggtacattt ccctgtgctg acggaagcca acttggcttt cccggactgc aagcagggct  4080
ctgccccaga ggcctctctc tccgtcgtgg gagagagacg tgtacatagt gtaggtcagc  4140
gtgcttagcc tcctgacctg aggctcctgt gctactttgc cttttgcaaa ctttattttc  4200
atagattgag aagttttgta cagagaatta aaaatgaaat tatttataat ctg         4253

SEQ ID NO: 5            moltype = RNA  length = 4056
FEATURE                 Location/Qualifiers
source                  1..4056
                        mol_type = mRNA
                        organism = Homo sapiens
SEQUENCE: 5
gcggggcggg cgcgccgcag cgctcaacgg cttcaaaaat ccgccgcgcc ttgacaggtg  60
aagtcggcgc ggggaggggt agggccaacg gcctggacgc cccaagggcg ggcgcagatc  120
gcggagccat ggattgcact ttcgaagaca tgcttcagct tatcaacaac caagacagtg  180
acttccctgg cctatttgac ccaccctatg ctgggagtgg ggcagggggc acagaccctg  240
ccagccccga taccagctcc ccaggcagct tgtctccacc tcctgccaca ttgagctcct  300
ctcttgaagc cttcctgagc gggccgcagg cagcgccctc acccctgtcc cctccccagc  360
ctgcacccac tccattgaag atgtacccgt ccatgcccgc tttctcccct gggcctggta  420
tcaaggaaga gtcagtgcca ctgagcatcc tgcagacccc caccccacag cccctgccag  480
gggccctcct gccacagagc ttcccagccc cagccccacc gcagttcagc tccacccctg  540
tgttaggcta ccccagccct ccgggaggct tctctacagg aagccctccc gggaacaccc  600
agcagccgct gcctggcctg ccactggctt ccccgccagg ggtcccgccc gtctccttgc  660
acacccaggt ccagagtgtg gtcccccagc agctactgac agtcacagct gcccccacgg  720
cagcccctgt aacgaccact gtgacctcgc agatccagca ggtcccggtc ctgctgcagc  780
cccacttcat caaggcagac tcgctgcttc tgacagccat gaagacagac ggagccactg  840
tgaaggcggc aggtctcagt cccctggtct ctggcaccac tgtgcagaca gggcctttgc  900
cgaccctggt gagtggcgga accatcttgg caacagtccc actggtcgta gatgcggaga  960
agctgcctat caaccggctc gcagctggca gcaaggcccc ggcctctgcc cagagccgtg  1020
gagagaagcg cacagcccac aacgccattg agaagcgcta ccgctcctcc atcaatgaca  1080
aaatcattga gctcaaggat ctggtggtgg gcactgaggc aaagctgaat aaatctgctg  1140
tcttgcgcaa ggccatcgac tacattcgct ttctgcaaca cagcaaccag aaactcaagc  1200
aggagaacct aagtctgcgc actgctgtcc acaaaagcaa atctctgaag gatctggtgt  1260
cggcctgtgg cagtggaggg aacacagacg tgctcatgga gggcgtgaag actgaggtgg  1320
aggacacact gaccccaccc ccctcggatg ctggctcacc tttccagagc agccccttgt  1380
cccttggcag caggggcagt ggcagcggtg gcagtggcag tgactcggag cctgacagcc  1440
cagtctttga ggacagcaag gcaaagccag agcagcggcc gtctctgcac agccggggca  1500
tgctggaccg ctcccgcctg gccctgtgca cgctcgtctt cctctgcctg tcctgcaacc  1560
ccttggcctc cttgctgggg gcccgggggc ttcccagccc ctcagatacc accagcgtct  1620
accatagccc tgggcgcaac gtgctgggca ccgagagcag agatggccct ggctgggccc  1680
agtggctgct gcccccagtg gtctggctgc tcaatgggct gttggtgctc gtctccttgg  1740
tgcttctctt tgtctacggt gagccagtca cacggcccca ctcaggcccc gccgtgtact  1800
tctggaggca tcgcaagcag gctgacctgg acctggcccg gggagacttt gcccaggctg  1860
cccagcagct gtggctggcc ctgcgggcac tgggccggcc cctgcccacc tcccacctgg  1920
acctggcttg tagcctcctc tggaacctca tccgtcacct gctgcagcgt ctctgggtgg  1980
gccgctggct ggcaggccgg gcagggggcc tgcagcagga ctgtgctctg cgagtggatg  2040
ctagcgccag cgcccgagac gcagccctgg tctaccataa gctgcaccag ctgcacacca  2100
tggggaagca cacaggcggg cacctcactg ccaccaacct ggcgctgagt gccctgaacc  2160
tggcagagtg tgcaggggat gccgtgtctg tggcgacgct ggccgagatc tatgtggcgg  2220
ctgcattgag agtgaagacc agtctcccac gggccttgca ttttctgaca cgcttcttcc  2280
tgagcagtgc ccgccaggcc tgcctggcac agagtggctc agtgcctcct gccatgcagt  2340
ggctctgcca ccccgtgggc caccgtttct tcgtggatgg ggactggtcc gtgctcagta  2400
ccccatggga gagcctgtac agcttggccg ggaacccagt ggacccccctg gcccaggtga  2460
ctcagctatt ccgggaacat ctcttagagc gagcactgaa ctgtgtgacc cagcccaacc  2520
ccagccctgg gtcagctgat ggggacaagg aattctcgga tgccctcggg tacctgcagc  2580
tgctgaacag ctgttctgat gctgcggggg ctcctgccta cagcttctcc atcagttcca  2640
gcatggccac caccaccggc gtagacccgg tggccaagtg gtgggcctct ctgacagctg  2700
tggtgatcca ctggctgcgg cgggatgagg aggcggctga gcggctgtgc ccgctggtgg  2760
agcacctgcc ccgggtgctg caggagtctg agagacccct gcccagggca gctctgcact  2820
ccttcaaggc tgcccgggcc ctgctgggct gtgccaaggc agagtctggt ccagccagcc  2880
tgaccatctg tgagaaggcc agtgggtacc tgcaggacag cctggctacc acaccagcca  2940
gcagctccat tgacaaggcc gtgcagctgt tcctgtgtga cctgcttctt gtggtgcgca  3000
ccagcctgtg gcggcagcag cagcccccgg ccccggcccc agcagcccag ggcaccagca  3060
gcaggcccca ggcttccgcc cttgagctgc gtggcttcca acgggacctg agcagcctga  3120
ggcggctggc acagagcttc cggcccgcca tgcggagggt gttcctacat gaggccacgg  3180
cccggctgat ggcgggggcc agccccacac ggacacacca gctcctcgac cgcagtctga  3240
ggcggcgggc aggccccggt ggcaaaggag gcgcggtggc ggagctggag ccgcggccca  3300
cgcggcggga gcacgcggag gccttgctgc tggcctcctg ctacctgccc cccggcttcc  3360
tgtcggcgcc cgggcagcgc gtgggcatgc tggctgaggc ggcgcgcaca ctcgagaagc  3420
ttggcgatcg ccggctgctg cacgactgtc agcagatgct catgcgcctg ggcggtggga  3480
```

-continued

```
ccactgtcac ttccagctag accccgtgtc cccggcctca gcacccctgt ctctagccac  3540
tttggtcccg tgcagcttct gtcctgcgtc gaagctttga aggccgaagg cagtgcaaga  3600
gactctggcc tccacagttc gacctgcggc tgctgtgtgc cttcgcggtg gaaggcccga  3660
ggggcgcgat cttgacccta agaccggcgg ccatgatggt gctgacctct ggtggccgat  3720
cggggcactg caggggccga gccattttgg ggggcccccc tccttgctct gcaggcacct  3780
tagtggcttt tttcctcctg tgtacaggga agagaggggt acatttccct gtgctgacgg  3840
aagccaactt ggctttcccg gactgcaagc agggctctgc cccagaggcc tctctctccg  3900
tcgtgggaga gagacgtgta catagtgtag gtcagcgtgc ttagcctcct gacctgaggc  3960
tcctgtgcta ctttgccttt tgcaaacttt attttcatag attgagaagt tttgtacaga  4020
gaattaaaaa tgaaattatt tataatctgg aaaaaa                            4056

SEQ ID NO: 6            moltype = RNA  length = 4178
FEATURE                 Location/Qualifiers
source                  1..4178
                        mol_type = mRNA
                        organism = Homo sapiens
SEQUENCE: 6
gcggccgggg gaacccagtt tccgaggaac ttttcgccgg cgccgggccg cctctgaggc  60
cagggcagga cacgaacgcg cggagcggcg gcggcgactg agagccgggg ccgcggcggc  120
gctccctagg aagggccgta cgaggcggcg ggcccggcgg gcctcccgga ggaggcggct  180
gcgccatgga cgagccaccc ttcagcgagg cggctttgga gcaggcgctg ggcgagccgt  240
gcgatctgga cgcggcgctg ctgaccgaca tcgaagacat gcttcagctt atcaacaacc  300
aagacagtga cttccctggc ctatttgacc caccctatgc tgggagtggg gcagggggca  360
cagaccctgc cagccccgat accagctccc caggcagctt gtctccacct cctgccacat  420
tgagctcctc tcttgaagcc ttcctgagcg ggccgcaggc agcgccctca cccctgtccc  480
ctccccagcc tgcacccact ccattgaaga tgtacccgtc catgcccgct ttctcccctg  540
ggcctggtat caaggaagag tcagtgccac tgagcatcct gcagaccccc accccacagc  600
ccctgccagg ggccctcctg ccacagagct tcccagcccc agccccaccg cagttcagct  660
ccacccctgt gttaggctac cccagccctc cgggaggctt ctctacagga agccctcccg  720
ggaacaccca gcagccgctg cctggcctgc cactggcttc cccgccaggg gtcccgcccg  780
tctccttgca cacccaggtc cagagtgtgg tcccccagca gctactgaca gtcacagctg  840
cccccacggc agcccctgta acgaccactg tgacctcgca gatccagcag gtcccggtcc  900
tgctgcagcc ccacttcatc aaggcagact cgctgcttct gacagccatg aagacagacg  960
gagccactgt gaaggcggca ggtctcagtc ccctggtctc tggcaccact gtgcagacag  1020
ggcctttgcc gaccctggtg agtggcggaa ccatcttggc aacagtccca ctggtcgtag  1080
atgcggagaa gctgcctatc aaccggctcg cagctggcag caaggccccg gcctctgccc  1140
agagccgtgg agagaagcgc acagcccaca acgccattga gaagtgctac cgctcctcca  1200
tcaatgacaa aatcattgag ctcaaggatc tggtggtggg cactgaggca aagctgaata  1260
aatctgctgt cttgcgcaag gccatcgact acattcgctt tctgcaacac agcaaccaga  1320
aactcaagca ggagaaccta agtctgcgca ctgctgtcca caaaagcaaa tctctgaagg  1380
atctggtgtc ggcctgtggc agtggaggga acacagacgt gctcatggag ggcgtgaaga  1440
ctgaggtgga ggacacactg accccacccc cctcggatgc tggctcacct ttccagagca  1500
gccccttgtc ccttggcagc aggggcagtg gcagcggtgg cagtggcagt gactcggagc  1560
ctgacagccc agtctttgag gacagcaagg caaagccaga gcagcggccg tctctgcaca  1620
gccggggcat gctggaccgc tcccgcctgg ccctgtgcac gctcgtcttc ctctgcctgt  1680
cctgcaaccc cttggcctcc ttgctggggg cccgggggct tcccagcccc tcagatacca  1740
ccagcgtcta ccatagccct gggcgcaacg tgctgggcac cgagagcaga gatggccctg  1800
gctgggccca gtggctgctg cccccagtgg tctggctgct caatgggctg ttggtgctcg  1860
tctccttggt gcttctcttt gtctacggtg agccagtcac acggccccac tcaggccccg  1920
ccgtgtactt ctggaggcat cgcaagcagg ctgacctgga cctggcccgg ggagactttg  1980
cccaggctgc ccagcagctg tggctggccc tgcgggcact gggccggccc ctgcccacct  2040
cccacctgga cctggcttgt agcctcctct ggaacctcat ccgtcacctg ctgcagcgtc  2100
tctgggtggg ccgctggctg gcaggccggg caggggggcct gcagcaggac tgtgctctgc  2160
gagtggatgc tagcgccagc gcccgagacg cagccctggt ctaccataag ctgcaccagc  2220
tgcacaccat ggggaagcac acaggcgggc acctcactgc caccaacctg gcgctgagtg  2280
ccctgaacct ggcagagtgt gcaggggatg ccgtgtctgt ggcgacgctg gccgagatct  2340
atgtggcggc tgcattgaga gtgaagacca gtctcccacg ggccttgcat tttctgacac  2400
gcttcttcct gagcagtgcc cgccaggcct gcctggcaca gagtggctca gtgcctcctg  2460
ccatgcagtg gctctgccac cccgtgggcc accgtttctt cgtggatggg gactggtccg  2520
tgctcagtac cccatgggag agcctgtaca gcttggccgg gaacccagtg gacccccctgg  2580
cccaggtgac tcagctattc cgggaacatc tcttagagcg agcactgaac tgtgtgaccc  2640
agcccaaccc cagccctggg tcagctgatg gggacaagga attctcggat gccctcgggt  2700
acctgcagct gctgaacagc tgttctgatg ctgcgggggc tcctgcctac agcttctcca  2760
tcagttccag catggccacc accaccggcg tagacccggt ggccaagtgg tgggcctctc  2820
tgacagctgt ggtgatccac tggctgcggc gggatgagga ggcggctgag cggctgtgcc  2880
cgctggtgga gcacctgccc cgggtgctgc aggagtctga gagacccctg cccagggcag  2940
ctctgcactc cttcaaggct gcccgggccc tgctgggctg tgccaaggca gagtctggtc  3000
cagccagcct gaccatctgt gagaaggcca gtgggtacct gcaggacagc ctggctacca  3060
caccagccag cagctccatt gacaaggccg tgcagctgtt cctgtgtgac ctgcttcttg  3120
tggtgcgcac cagcctgtgg cggcagcagc agcccccggc cccggcccca gcagcccagg  3180
gcaccagcag caggccccag gcttccgccc ttgagctgcg tggcttccaa cgggacctga  3240
gcagcctgag gcggctggca cagagcttcc ggcccgccat gcggagggtg ttcctacatg  3300
aggccacggc ccggctgatg gcgggggcca gccccacacg gacacaccag ctcctcgacc  3360
gcagtctgag gcggcgggca ggccccggtg gcaaaggagg cgcggtggcg gagctggagc  3420
cgcggcccac gcggcgggag cacgcggagg ccttgctgct ggcctcctgc tacctgcccc  3480
ccggcttcct gtcggcgccc gggcagcgcg tgggcatgct ggctgaggcg gcgcgcacac  3540
tcgagaagct tggcgatcgc cggctgctgc acgactgtca gcagatgctc atgcgcctgg  3600
gcggtgggac cactgtcact tccagctaga ccccgtgtcc ccggcctcag cacccctgtc  3660
tctagccact ttggtcccgt gcagcttctg tcctgcgtcg aagctttgaa ggccgaaggc  3720
```

```
agtgcaagag actctggcct ccacagttcg acctgcggct gctgtgtgcc ttcgcggtgg  3780
aaggcccgag gggcgcgatc ttgaccctaa gaccggcggc catgatggtg ctgacctctg  3840
gtggccgatc ggggcactgc aggggccgag ccattttggg gggccccct ccttgctctg  3900
caggcacctt agtggctttt ttcctcctgt gtacagggaa gagaggggta catttccctg  3960
tgctgacgga agccaacttg gctttcccgg actgcaagca gggctctgcc ccagaggcct  4020
ctctctccgt cgtgggagag agacgtgtac atagtgtagg tcagcgtgct tagcctcctg  4080
acctgaggct cctgtgctac tttgcctttt gcaaacttta ttttcataga ttgagaagtt  4140
ttgtacagag aattaaaaat gaaattattt ataatctg                          4178

SEQ ID NO: 7           moltype = RNA  length = 4253
FEATURE                Location/Qualifiers
source                 1..4253
                       mol_type = mRNA
                       organism = Homo sapiens
SEQUENCE: 7
cagtttccga ggaacttttc gccggcgccg ggccgcctct gaggccaggg caggacacga  60
acgcgcggag cggcggcggc gactgagagc cggggccgcg gcggcgctcc ctaggaaggg  120
ccgtacgagg cggcgggccc ggcgggcctc ccggaggagg cggctgcgcc atggacgagc  180
caccccttcag cgaggcggct ttggagcagg cgctgggcga gccgtgcgat ctggacgcgg  240
cgctgctgac cgacatcgaa ggtgaagtcg gcgcggggag gggtagggcc aacggcctgg  300
acgccccaag ggcgggcgca gatcgcggag ccatggattg cactttcgaa gacatgcttc  360
agcttatcaa caaccaagac agtgacttcc ctggcctatt tgacccaccc tatgctggga  420
gtggggcagg gggcacagac cctgccagcc ccgataccag ctccccaggc agcttgtctc  480
cacctcctgc cacattgagc tcctctcttg aagccttcct gagcgggccg caggcagcgc  540
cctcacccct gtcccctccc cagcctgcac ccactccatt gaagatgtac ccgtccatgc  600
ccgctttctc ccctgggcct ggtatcaagg aagagtcagt gccactgagc atcctgcaga  660
cccccacccc acagcccctg ccaggggccc tcctgccaca gagcttccca gccccagccc  720
caccgcagtt cagctccacc cctgtgttag gctaccccag ccctccggga ggcttctcta  780
caggaagccc tcccgggaac acccagcagc cgctgcctgg cctgccactg gcttccccgc  840
caggggtccc gcccgtctcc ttgcacaccc aggtccagag tgtggtcccc cagcagctac  900
tgacagtcac agctgccccc acggcagccc ctgtaacgac cactgtgacc tcgcagatcc  960
agcaggtccc ggtcctgctg cagcccccact tcatcaaggc agactcgctg cttctgacag  1020
ccatgaagac agacggagcc actgtgaagg cggcaggtct cagtcccctg gtctctggca  1080
ccactgtgca gacagggcct ttgccgaccc tggtgagtgg cggaaccatc ttggcaacag  1140
tcccactggt cgtagatgcg gagaagctgc ctatcaaccg gctcgcagct ggcagcaagg  1200
ccccggcctc tgcccagagc cgtggagaga agcgcacagc ccacaacgcc attgagaagt  1260
gctaccgctc ctccatcaat gacaaaatca ttgagctcaa ggatctggtg gtgggcactg  1320
aggcaaagct gaataaatct gctgtcttgc gcaaggccat cgactacatt cgctttctgc  1380
aacacagcaa ccagaaactc aagcaggaga acctaagtct gcgcactgct gtccacaaaa  1440
gcaaatctct gaaggatctg gtgtcggcct gtggcagtgg agggaacaca gacgtgctca  1500
tggagggcgt gaagactgag gtggaggaca cactgaccccc accccccctcg gatgctggct  1560
cacctttcca gagcagcccc ttgtcccttg gcagcagggg cagtggcagc ggtggcagtg  1620
gcagtgactc ggagcctgac agcccagtct ttgaggacag caaggcaaag ccagagcagc  1680
ggccgtctct gcacagccgg ggcatgctgg accgctcccg cctggccctg tgcacgctcg  1740
tcttcctctg cctgtcctgc aacccccttgg cctccttgct gggggcccgg gggcttccca  1800
gccccctcaga taccaccagc gtctaccata gccctgggcg caacgtgctg ggcaccgaga  1860
gcagagatgg ccctggctgg gcccagtggc tgctgccccc agtggtctgg ctgctcaatg  1920
ggctgttggt gctcgtctcc ttggtgcttc tctttgtcta cggtgagcca gtcacacggc  1980
cccactcagg ccccgccgtg tacttctgga ggcatcgcaa gcaggctgac ctggacctgg  2040
cccggggaga ctttgcccag gctgcccagc agctgtggct ggccctgcgg gcactgggcc  2100
ggccccctgcc cacctcccac ctggacctgg cttgtagcct cctctggaac ctcatccgtc  2160
acctgctgca gcgtctctgg gtgggccgct ggctggcagg ccgggcaggg ggcctgcagc  2220
aggactgtgc tctgcgagtg gatgctagcg ccagcgcccg agacgcagcc ctggtctacc  2280
ataagctgca ccagctgcac accatgggga agcacacagg cgggcacctc actgccacca  2340
acctggcgct gagtgccctg aacctggcag agtgtgcagg ggatgccgtg tctgtggcga  2400
cgctggccga gatctatgtg gcggctgcat tgagagtgaa gaccagtctc ccacgggcct  2460
tgcattttct gacacgcttc ttcctgagca gtgcccgcca ggcctgcctg gcacagagtg  2520
gctcagtgcc tcctgccatg cagtggctct gccaccccgt gggccaccgt ttcttcgtgg  2580
atggggactg gtccgtgctc agtaccccat gggagagcct gtacagcttg gccgggaacc  2640
cagtggaccc cctggcccag gtgactcagc tattccggga acatctctta gagcgagcac  2700
tgaactgtgt gacccagccc aaccccagcc ctgggtcagc tgatggggac aaggaattct  2760
cggatgccct cgggtacctg cagctgctga acagctgttc tgatgctgcg ggggctcctg  2820
cctacagctt ctccatcagt tccagcatgg ccaccaccac cggcgtagac ccggtggcca  2880
agtggtgggc ctctctgaca gctgtggtga tccactggct gcggcgggat gaggaggcgg  2940
ctgagcggct gtgcccgctg gtggagcacc tgccccgggt gctgcaggag tctgagagac  3000
ccctgcccag ggcagctctg cactccttca aggctgcccg ggccctgctg ggctgtgcca  3060
aggcagagtc tggtccagcc agcctgacca tctgtgagaa ggccagtggg tacctgcagg  3120
acagcctggc taccacacca gccagcagct ccattgacaa ggccgtgcag ctgttcctgt  3180
gtgacctgct tcttgtggtg cgcaccagcc tgtggcggca gcagcagccc ccggccccgg  3240
ccccagcagc ccagggcacc agcagcaggc cccaggcttc cgcccttgag ctgcgtggct  3300
tccaacggga cctgagcagc ctgaggcggc tggcacagag cttccggccc gccatgcgga  3360
gggtgttcct acatgaggcc acggcccggc tgatggcggg ggccagcccc acacggacac  3420
accagctcct cgaccgcagt ctgaggcggc gggcaggccc cggtggcaaa ggaggcgcgg  3480
tggcggagct ggagccgcgg cccacgcggc gggagcacgc ggaggccttg ctgctggcct  3540
cctgctacct gcccccggc ttcctgtcgg cgcccgggca gcgcgtgggc atgctggctg  3600
aggcggcgcg cacactcgag aagcttggcg atcgccggct gctgcacgac tgtcagcaga  3660
tgctcatgcg cctgggcggt gggaccactg tcacttccag ctagaccccg tgtccccggc  3720
ctcagcaccc ctgtctctag ccactttggt cccgtgcagc ttctgtcctg cgtcgaagct  3780
ttgaaggccg aaggcagtgc aagagactct ggcctccaca gttcgacctg cggctgctgt  3840
```

```
gtgccttcgc ggtggaaggc ccgaggggcg cgatcttgac cctaagaccg gcggccatga  3900
tggtgctgac ctctggtggc cgatcggggc actgcagggg ccgagccatt ttggggggcc  3960
cccctccttg ctctgcaggc accttagtgg cttttttcct cctgtgtaca gggaagagag  4020
gggtacattt ccctgtgctg acggaagcca acttggcttt cccggactgc aagcagggct  4080
ctgccccaga ggcctctctc tccgtcgtgg gagagagacg tgtacatagt gtaggtcagc  4140
gtgcttagcc tcctgacctg aggctcctgt gctactttgc cttttgcaaa ctttattttc  4200
atagattgag aagttttgta cagagaatta aaaatgaaat tatttataat ctg         4253

SEQ ID NO: 8            moltype = RNA  length = 4056
FEATURE                 Location/Qualifiers
source                  1..4056
                        mol_type = mRNA
                        organism = Homo sapiens
SEQUENCE: 8
gcggggcggg cgcgccgcag cgctcaacgg cttcaaaaat ccgccgcgcc ttgacaggtg  60
aagtcggcgc ggggaggggt agggccaacg gcctggacgc cccaagggcg ggcgcagatc  120
gcggagccat ggattgcact ttcgaagaca tgcttcagct tatcaacaac caagacagtg  180
acttccctgg cctatttgac ccaccctatg ctgggagtgg ggcagggggc acagaccctg  240
ccagccccga taccagctcc ccaggcagct tgtctccacc tcctgccaca ttgagctcct  300
ctcttgaagc cttcctgagc gggccgcagg cagcgccctc acccctgtcc cctccccagc  360
ctgcacccac tccattgaag atgtacccgt ccatgcccgc tttctcccct gggcctggta  420
tcaaggaaga gtcagtgcca ctgagcatcc tgcagacccc caccccacag cccctgccag  480
gggccctcct gccacagagc ttcccagccc cagccccacc gcagttcagc tccacccctg  540
tgttaggcta ccccagccct ccgggaggct tctctacagg aagccctccc gggaacaccc  600
agcagccgct gcctggcctg ccactggctt ccccgccagg ggtcccgccc gtctccttgc  660
acacccaggt ccagagtgtg gtcccccagc agctactgac agtcacagct gcccccacgg  720
cagcccctgt aacgaccact gtgacctcgc agatccagca ggtcccggtc ctgctgcagc  780
cccacttcat caaggcagac tcgctgcttc tgacagccat gaagacagac ggagccactg  840
tgaaggcggc aggtctcagt cccctggtct ctggcaccac tgtgcagaca gggcctttgc  900
cgaccctggt gagtggcgga accatcttgg caacagtccc actggtcgta gatgcggaga  960
agctgcctat caaccggctc gcagctggca gcaaggcccc ggcctctgcc cagagccgtg  1020
gagagaagcg cacagcccac aacgccattg agaagtgcta ccgctcctcc atcaatgaca  1080
aaatcattga gctcaaggat ctggtggtgg gcactgaggc aaagctgaat aaatctgctg  1140
tcttgcgcaa ggccatcgac tacattcgct ttctgcaaca cagcaaccag aaactcaagc  1200
aggagaacct aagtctgcgc actgctgtcc acaaaagcaa atctctgaag gatctggtgt  1260
cggcctgtgg cagtggaggg aacacagacg tgctcatgga gggcgtgaag actgaggtgg  1320
aggacacact gaccccaccc ccctcggatg ctggctcacc tttccagagc agccccttgt  1380
cccttggcag caggggcagt ggcagcggtg gcagtggcag tgactcggag cctgacagcc  1440
cagtctttga ggacagcaag gcaaagccag agcagcggcc gtctctgcac agccggggca  1500
tgctggaccg ctcccgcctg gccctgtgca cgctcgtctt cctctgcctg tcctgcaacc  1560
ccttggcctc cttgctgggg gcccgggggc ttcccagccc ctcagatacc accagcgtct  1620
accatagccc tgggcgcaac gtgctgggca ccgagagcag agatggccct ggctgggccc  1680
agtggctgct gcccccagtg gtctggctgc tcaatgggct gttggtgctc gtctccttgg  1740
tgcttctctt tgtctacggt gagccagtca cacggcccca ctcaggcccc gccgtgtact  1800
tctggaggca tcgcaagcag gctgacctgg acctggcccg gggagacttt gcccaggctg  1860
cccagcagct gtggctggcc ctgcgggcac tgggccggcc cctgcccacc tcccacctgg  1920
acctggcttg tagcctcctc tggaacctca tccgtcacct gctgcagcgt ctctgggtgg  1980
gccgctggct ggcaggccgg gcagggggcc tgcagcagga ctgtgctctg cgagtggatg  2040
ctagcgccag cgcccgagac gcagccctgg tctaccataa gctgcaccag ctgcacacca  2100
tggggaagca cacaggcggg cacctcactg ccaccaacct ggcgctgagt gccctgaacc  2160
tggcagagtg tgcaggggat gccgtgtctg tggcgacgct ggccgagatc tatgtggcgg  2220
ctgcattgag agtgaagacc agtctcccac gggccttgca ttttctgaca cgcttcttcc  2280
tgagcagtgc ccgccaggcc tgcctggcac agagtggctc agtgcctcct gccatgcagt  2340
ggctctgcca ccccgtgggc caccgtttct tcgtggatgg ggactggtcc gtgctcagta  2400
ccccatggga gagcctgtac agcttggccg ggaacccagt ggacccccctg gcccaggtga  2460
ctcagctatt ccgggaacat ctcttagagc gagcactgaa ctgtgtgacc cagcccaacc  2520
ccagccctgg gtcagctgat ggggacaagg aattctcgga tgccctcggg tacctgcagc  2580
tgctgaacag ctgttctgat gctgcggggg ctcctgccta cagcttctcc atcagttcca  2640
gcatggccac caccaccggc gtagacccgg tggccaagtg gtgggcctct ctgacagctg  2700
tggtgatcca ctggctgcgg cgggatgagg aggcggctga gcggctgtgc ccgctggtgg  2760
agcacctgcc ccgggtgctg caggagtctg agagacccct gcccagggca gctctgcact  2820
ccttcaaggc tgcccgggcc ctgctgggct gtgccaaggc agagtctggt ccagccagcc  2880
tgaccatctg tgagaaggcc agtgggtacc tgcaggacag cctggctacc acaccagcca  2940
gcagctccat tgacaaggcc gtgcagctgt tcctgtgtga cctgcttctt gtggtgcgca  3000
ccagcctgtg gcggcagcag cagcccccgg ccccggcccc agcagcccag ggcaccagca  3060
gcaggcccca ggcttccgcc cttgagctgc gtggcttcca acgggacctg agcagcctga  3120
ggcggctggc acagagcttc cggcccgcca tgcggagggt gttcctacat gaggccacgg  3180
cccggctgat ggcgggggcc agccccacac ggacacacca gctcctcgac cgcagtctga  3240
ggcggcgggc aggccccggt ggcaaaggag gcgcggtggc ggagctggag ccgcggccca  3300
cgcggcggga gcacgcggag gccttgctgc tggcctcctg ctacctgccc cccggcttcc  3360
tgtcggcgcc cgggcagcgc gtgggcatgc tggctgaggc ggcgcgcaca ctcgagaagc  3420
ttggcgatcg ccggctgctg cacgactgtc agcagatgct catgcgcctg ggcggtggga  3480
ccactgtcac ttccagctag accccgtgtc cccggcctca gcacccctgt ctctagccac  3540
tttggtcccg tgcagcttct gtcctgcgtc gaagctttga aggccgaagg cagtgcaaga  3600
gactctggcc tccacagttc gacctgcggc tgctgtgtgc cttcgcggtg gaaggcccga  3660
ggggcgcgat cttgacccta agaccggcgg ccatgatggt gctgacctct ggtggccgat  3720
cggggcactg caggggccga gccattttgg ggggcccccc tccttgctct gcaggcacct  3780
tagtggcttt tttcctcctg tgtacaggga agagaggggt acatttccct gtgctgacgg  3840
aagccaactt ggctttcccg gactgcaagc agggctctgc cccagaggcc tctctctccg  3900
```

```
tcgtgggaga gagacgtgta catagtgtag gtcagcgtgc ttagcctcct gacctgaggc  3960
tcctgtgcta ctttgccttt tgcaaacttt attttcatag attgagaagt tttgtacaga  4020
gaattaaaaa tgaaattatt tataatctgg aaaaaa                            4056

SEQ ID NO: 9            moltype = DNA  length = 4178
FEATURE                 Location/Qualifiers
source                  1..4178
                        mol_type = other DNA
                        organism = Homo sapiens
SEQUENCE: 9
gcggccgggg gaacccagtt tccgaggaac ttttcgccgg cgccgggccg cctctgaggc  60
cagggcagga cacgaacgcg cggagcggcg gcggcgactg agagccgggg ccgcggcggc  120
gctccctagg aagggccgta cgaggcggcg ggcccggcgg gcctcccgga ggaggcggct  180
gcgccatgga cgagccaccc ttcagcgagg cggctttgga gcaggcgctg ggcgagccgt  240
gcgatctgga cgcggcgctg ctgaccgaca tcgaagacat gcttcagctt atcaacaacc  300
aagacagtga cttccctggc ctatttgacc caccctatgc tgggagtggg gcagggggca  360
cagaccctgc cagccccgat accagctccc caggcagctt gtctccacct cctgccacat  420
tgagctcctc tcttgaagcc ttcctgagcg ggccgcaggc agcgccctca cccctgtccc  480
ctccccagcc tgcacccact ccattgaaga tgtacccgtc catgcccgct ttctcccctg  540
ggcctggtat caaggaagag tcagtgccac tgagcatcct gcagaccccc accccacagc  600
ccctgccagg ggccctcctg ccacagagct tcccagcccc agccccaccg cagttcagct  660
ccacccctgt gttaggctac cccagccctc cgggaggctt ctctacagga agccctcccg  720
ggaacaccca gcagccgctg cctggcctgc cactggcttc cccgccaggg gtcccgcccg  780
tctccttgca cacccaggtc cagagtgtgg tcccccagca gctactgaca gtcacagctg  840
cccccacggc agcccctgta acgaccactg tgacctcgca gatccagcag gtcccggtcc  900
tgctgcagcc ccacttcatc aaggcagact cgctgcttct gacagccatg aagacagacg  960
gagccactgt gaaggcggca ggtctcagtc ccctggtctc tggcaccact gtgcagacag  1020
ggcctttgcc gaccctggtg agtggcggaa ccatcttggc aacagtccca ctggtcgtag  1080
atgcggagaa gctgcctatc aaccggctcg cagctggcag caaggccccg gcctctgccc  1140
agagccgtgg agagaagcgc acagcccaca acgccattga gaagcgctac cgctcctcca  1200
tcaatgacaa aatcattgag ctcaaggatc tggtggtggg cactgaggca aagctgaata  1260
aatctgctgt cttgcgcaag gccatcgact acattcgctt tctgcaacac agcaaccaga  1320
aactcaagca ggagaaccta agtctgcgca ctgctgtcca caaaagcaaa tctctgaagg  1380
atctggtgtc ggcctgtggc agtggaggga acacagacgt gctcatggag ggcgtgaaga  1440
ctgaggtgga ggacacactg accccacccc cctcggatgc tggctcacct ttccagagca  1500
gccccttgtc ccttggcagc aggggcagtg gcagcggtgg cagtggcagt gactcggagc  1560
ctgacagccc agtctttgag gacagcaagg caaagccaga gcagcggccg tctctgcaca  1620
gccggggcat gctggaccgc tcccgcctgg ccctgtgcac gctcgtcttc ctctgcctgt  1680
cctgcaaccc cttggcctcc ttgctggggg cccgggggct tcccagcccc tcagatacca  1740
ccagcgtcta ccatagccct gggcgcaacg tgctgggcac cgagagcaga gatggccctg  1800
gctgggccca gtggctgctg cccccagtgg tctggctgct caatgggctg ttggtgctcg  1860
tctccttggt gcttctcttt gtctacggtg agccagtcac acggccccac tcaggccccg  1920
ccgtgtactt ctggaggcat cgcaagcagg ctgacctgga cctggcccgg ggagactttg  1980
cccaggctgc ccagcagctg tggctggccc tgcgggcact gggccggccc ctgcccacct  2040
cccacctgga cctggcttgt agcctcctct ggaacctcat ccgtcacctg ctgcagcgtc  2100
tctgggtggg ccgctggctg gcaggccggg caggggggcct gcagcaggac tgtgctctgc  2160
gagtggatgc tagcgccagc gcccgagacg cagccctggt ctaccataag ctgcaccagc  2220
tgcacaccat ggggaagcac acaggcgggc acctcactgc caccaacctg gcgctgagtg  2280
ccctgaacct ggcagagtgt gcaggggatg ccgtgtctgt ggcgacgctg gccgagatct  2340
atgtggcggc tgcattgaga gtgaagacca gtctcccacg ggccttgcat tttctgacac  2400
gcttcttcct gagcagtgcc cgccaggcct gcctggcaca gagtggctca gtgcctcctg  2460
ccatgcagtg gctctgccac cccgtgggcc accgtttctt cgtggatggg gactggtccg  2520
tgctcagtac cccatgggag agcctgtaca gcttggccgg gaacccagtg gacccccctgg  2580
cccaggtgac tcagctattc cgggaacatc tcttagagcg agcactgaac tgtgtgaccc  2640
agcccaaccc cagccctggg tcagctgatg gggacaagga attctcggat gccctcgggt  2700
acctgcagct gctgaacagc tgttctgatg ctgcgggggc tcctgcctac agcttctcca  2760
tcagttccag catggccacc accaccggcg tagacccggt ggccaagtgg tgggcctctc  2820
tgacagctgt ggtgatccac tggctgcggc gggatgagga ggcggctgag cggctgtgcc  2880
cgctggtgga gcacctgccc cgggtgctgc aggagtctga gagacccctg cccagggcag  2940
ctctgcactc cttcaaggct gcccgggccc tgctgggctg tgccaaggca gagtctggtc  3000
cagccagcct gaccatctgt gagaaggcca gtgggtacct gcaggacagc ctggctacca  3060
caccagccag cagctccatt gacaaggccg tgcagctgtt cctgtgtgac ctgcttcttg  3120
tggtgcgcac cagcctgtgg cggcagcagc agcccccggc cccggcccca gcagcccagg  3180
gcaccagcag caggccccag gcttccgccc ttgagctgcg tggcttccaa cgggacctga  3240
gcagcctgag gcggctggca cagagcttcc ggcccgccat gcggagggtg ttcctacatg  3300
aggccacggc ccggctgatg gcgggggcca gccccacacg gacacaccag ctcctcgacc  3360
gcagtctgag gcggcgggca ggccccggtg gcaaaggagg cgcggtggcg gagctggagc  3420
cgcggcccac gcggcgggag cacgcggagg ccttgctgct ggcctcctgc tacctgcccc  3480
ccggcttcct gtcggcgccc gggcagcgcg tgggcatgct ggctgaggcg gcgcgcacac  3540
tcgagaagct tggcgatcgc cggctgctgc acgactgtca gcagatgctc atgcgcctgg  3600
gcggtgggac cactgtcact tccagctaga ccccgtgtcc ccggcctcag cacccctgtc  3660
tctagccact ttggtcccgt gcagcttctg tcctgcgtcg aagctttgaa ggccgaaggc  3720
agtgcaagag actctggcct ccacagttcg acctgcggct gctgtgtgcc ttcgcggtgg  3780
aaggcccgag gggcgcgatc ttgaccctaa gaccggcggc catgatggtg ctgacctctg  3840
gtggccgatc ggggcactgc aggggccgag ccattttggg gggccccccct ccttgctctg  3900
caggcacctt agtggctttt ttcctcctgt gtacagggaa gagaggggta catttccctg  3960
tgctgacgga agccaacttg gctttcccgg actgcaagca gggctctgcc ccagaggcct  4020
ctctctccgt cgtgggagag agacgtgtac atagtgtagg tcagcgtgct tagcctcctg  4080
acctgaggct cctgtgctac tttgcctttt gcaaacttta ttttcataga ttgagaagtt  4140
```

```
ttgtacagag aattaaaaat gaaattattt ataatctg                      4178

SEQ ID NO: 10          moltype = DNA  length = 4253
FEATURE                Location/Qualifiers
source                 1..4253
                       mol_type = other DNA
                       organism = Homo sapiens
SEQUENCE: 10
cagtttccga ggaacttttc gccggcgccg ggccgcctct gaggccaggg caggacacga  60
acgcgcggag cggcggcggc gactgagagc cggggccgcg gcggcgctcc ctaggaaggg  120
ccgtacgagg cggcgggccc ggcgggcctc ccggaggagg cggctgcgcc atggacgagc  180
caccccttcag cgaggcggct ttggagcagg cgctgggcga gccgtgcgat ctggacgcgg  240
cgctgctgac cgacatcgaa ggtgaagtcg gcgcggggag gggtagggcc aacggcctgg  300
acgccccaag ggcgggcgca gatcgcggag ccatggattg cactttcgaa gacatgcttc  360
agcttatcaa caaccaagac agtgacttcc ctggcctatt tgacccaccc tatgctggga  420
gtggggcagg gggcacagac cctgccagcc ccgataccag ctccccaggc agcttgtctc  480
cacctcctgc cacattgagc tcctctcttg aagccttcct gagcgggccg caggcagcgc  540
cctcacccct gtcccctccc cagcctgcac ccactccatt gaagatgtac ccgtccatgc  600
ccgctttctc ccctgggcct ggtatcaagg aagagtcagt gccactgagc atcctgcaga  660
cccccacccc acagcccctg ccaggggccc tcctgccaca gagcttccca gccccagccc  720
caccgcagtt cagctccacc cctgtgttag gctaccccag ccctccggga ggcttctcta  780
caggaagccc tcccgggaac acccagcagc cgctgcctgg cctgccactg gcttccccgc  840
caggggtccc gcccgtctcc ttgcacaccc aggtccagag tgtggtcccc cagcagctac  900
tgacagtcac agctgccccc acggcagccc ctgtaacgac cactgtgacc tcgcagatcc  960
agcaggtccc ggtcctgctg cagccccact tcatcaaggc agactcgctg cttctgacag  1020
ccatgaagac agacggagcc actgtgaagg cggcaggtct cagtcccctg gtctctggca  1080
ccactgtgca gacagggcct ttgccgaccc tggtgagtgg cggaaccatc ttggcaacag  1140
tcccactggt cgtagatgcg gagaagctgc ctatcaaccg gctcgcagct ggcagcaagg  1200
ccccggcctc tgcccagagc cgtggagaga agcgcacagc ccacaacgcc attgagaagc  1260
gctaccgctc ctccatcaat gacaaaatca ttgagctcaa ggatctggtg gtgggcactg  1320
aggcaaagct gaataaatct gctgtcttgc gcaaggccat cgactacatt cgctttctgc  1380
aacacagcaa ccagaaactc aagcaggaga acctaagtct gcgcactgct gtccacaaaa  1440
gcaaatctct gaaggatctg gtgtcggcct gtggcagtgg agggaacaca gacgtgctca  1500
tggagggcgt gaagactgag gtggaggaca cactgacccc accccccctcg gatgctggct  1560
cacctttcca gagcagcccc ttgtcccttg gcagcagggg cagtggcagc ggtggcagtg  1620
gcagtgactc ggagcctgac agcccagtct ttgaggacag caaggcaaag ccagagcagc  1680
ggccgtctct gcacagccgg ggcatgctgg accgctcccg cctggccctg tgcacgctcg  1740
tcttcctctg cctgtcctgc aaccccttgg cctccttgct ggggggcccgg gggcttccca  1800
gcccctcaga taccaccagc gtctaccata gccctgggcg caacgtgctg ggcaccgaga  1860
gcagagatgg ccctggctgg gcccagtggc tgctgccccc agtggtctgg ctgctcaatg  1920
ggctgttggt gctcgtctcc ttggtgcttc tctttgtcta cggtgagcca gtcacacggc  1980
cccactcagg ccccgccgtg tacttctgga ggcatcgcaa gcaggctgac ctggacctgg  2040
cccggggaga ctttgcccag gctgcccagc agctgtggct ggccctgcgg gcactgggcc  2100
ggcccctgcc cacctcccac ctggacctgg cttgtagcct cctctggaac ctcatccgtc  2160
acctgctgca gcgtctctgg gtgggccgct ggctggcagg ccgggcaggg ggcctgcagc  2220
aggactgtgc tctgcgagtg gatgctagcg ccagcgcccg agacgcagcc ctggtctacc  2280
ataagctgca ccagctgcac accatgggga agcacacagg cgggcacctc actgccacca  2340
acctggcgct gagtgccctg aacctggcag agtgtgcagg ggatgccgtg tctgtggcga  2400
cgctggccga gatctatgtg gcggctgcat tgagagtgaa gaccagtctc ccacgggcct  2460
tgcattttct gacacgcttc ttcctgagca gtgcccgcca ggcctgcctg gcacagagtg  2520
gctcagtgcc tcctgccatg cagtggctct gccaccccgt gggccaccgt ttcttcgtgg  2580
atggggactg gtccgtgctc agtaccccat gggagagcct gtacagcttg gccgggaacc  2640
cagtggaccc cctggcccag gtgactcagc tattccggga acatctctta gagcgagcac  2700
tgaactgtgt gacccagccc aaccccagcc ctgggtcagc tgatggggac aaggaattct  2760
cggatgccct cgggtacctg cagctgctga acagctgttc tgatgctgcg ggggctcctg  2820
cctacagctt ctccatcagt tccagcatgg ccaccaccac cggcgtagac ccggtggcca  2880
agtggtgggc ctctctgaca gctgtggtga tccactggct gcggcgggat gaggaggcgg  2940
ctgagcggct gtgcccgctg gtggagcacc tgccccgggt gctgcaggag tctgagagac  3000
ccctgcccag ggcagctctg cactccttca aggctgcccg ggccctgctg ggctgtgcca  3060
aggcagagtc tggtccagcc agcctgacca tctgtgagaa ggccagtggg tacctgcagg  3120
acagcctggc taccacacca gccagcagct ccattgacaa ggccgtgcag ctgttcctgt  3180
gtgacctgct tcttgtggtg cgcaccagcc tgtggcggca gcagcagccc ccggcccccgg  3240
ccccagcagc ccagggcacc agcagcaggc cccaggcttc cgcccttgag ctgcgtggct  3300
tccaacggga cctgagcagc ctgaggcggc tggcacagag cttccggccc gccatgcgga  3360
gggtgttcct acatgaggcc acggcccggc tgatggcggg ggccagcccc acacggacac  3420
accagctcct cgaccgcagt ctgaggcggc gggcaggccc cggtggcaaa ggaggcgcgg  3480
tggcggagct ggagccgcgg cccacgcggc gggagcacgc ggaggccttg ctgctggcct  3540
cctgctacct gccccccggc ttcctgtcgg cgcccgggca gcgcgtgggc atgctggctg  3600
aggcggcgcg cacactcgag aagcttggcg atcgccggct gctgcacgac tgtcagcaga  3660
tgctcatgcg cctgggcggt gggaccactg tcacttccag ctagaccccg tgtccccggc  3720
ctcagcaccc ctgtctctag ccactttggt cccgtgcagc ttctgtcctg cgtcgaagct  3780
ttgaaggccg aaggcagtgc aagagactct ggcctccaca gttcgacctg cggctgctgt  3840
gtgccttcgc ggtggaaggc ccgaggggcg cgatcttgac cctaagaccg gcggccatga  3900
tggtgctgac ctctggtggc cgatcggggc actgcagggg ccgagccatt ttggggggcc  3960
cccctccttg ctctgcaggc accttagtgg cttttttcct cctgtgtaca gggaagagag  4020
gggtacattt ccctgtgctg acggaagcca acttggcttt cccggactgc aagcagggct  4080
ctgccccaga ggcctctctc tccgtcgtgg gagagagacg tgtacatagt gtaggtcagc  4140
gtgcttagcc tcctgacctg aggctcctgt gctactttgc cttttgcaaa ctttattttc  4200
atagattgag aagttttgta cagagaatta aaaatgaaat tatttataat ctg        4253
```

```
SEQ ID NO: 11          moltype = DNA  length = 4056
FEATURE                Location/Qualifiers
source                 1..4056
                       mol_type = other DNA
                       organism = Homo sapiens
SEQUENCE: 11
gcggggcggg cgcgccgcag cgctcaacgg cttcaaaaat ccgccgcgcc ttgacaggtg  60
aagtcggcgc ggggaggggt agggccaacg gcctggacgc cccaagggcg ggcgcagatc  120
gcggagccat ggattgcact ttcgaagaca tgcttcagct tatcaacaac caagacagtg  180
acttccctgg cctatttgac ccaccctatg ctgggagtgg ggcagggggc acagaccctg  240
ccagccccga taccagctcc ccaggcagct tgtctccacc tcctgccaca ttgagctcct  300
ctcttgaagc cttcctgagc gggccgcagg cagcgccctc acccctgtcc cctccccagc  360
ctgcacccac tccattgaag atgtacccgt ccatgcccgc tttctcccct gggcctggta  420
tcaaggaaga gtcagtgcca ctgagcatcc tgcagacccc caccccacag cccctgccag  480
gggccctcct gccacagagc ttcccagccc cagccccacc gcagttcagc tccacccctg  540
tgttaggcta ccccagccct ccgggaggct tctctacagg aagccctccc gggaacaccc  600
agcagccgct gcctggcctg ccactggctt ccccgccagg ggtcccgccc gtctccttgc  660
acacccaggt ccagagtgtg gtcccccagc agctactgac agtcacagct gcccccacgg  720
cagcccctgt aacgaccact gtgacctcgc agatccagca ggtcccggtc ctgctgcagc  780
cccacttcat caaggcagac tcgctgcttc tgacagccat gaagacagac ggagccactg  840
tgaaggcggc aggtctcagt cccctggtct ctggcaccac tgtgcagaca gggcctttgc  900
cgaccctggt gagtggcgga accatcttgg caacagtccc actggtcgta gatgcggaga  960
agctgcctat caaccggctc gcagctggca gcaaggcccc ggcctctgcc cagagccgtg  1020
gagagaagcg cacagcccac aacgccattg agaagcgcta ccgctcctcc atcaatgaca  1080
aaatcattga gctcaaggat ctggtggtgg gcactgaggc aaagctgaat aaatctgctg  1140
tcttgcgcaa ggccatcgac tacattcgct ttctgcaaca cagcaaccag aaactcaagc  1200
aggagaacct aagtctgcgc actgctgtcc acaaaagcaa atctctgaag gatctggtgt  1260
cggcctgtgg cagtggaggg aacacagacg tgctcatgga gggcgtgaag actgaggtgg  1320
aggacacact gaccccaccc ccctcggatg ctggctcacc tttccagagc agccccttgt  1380
cccttggcag caggggcagt ggcagcggtg gcagtggcag tgactcggag cctgacagcc  1440
cagtctttga ggacagcaag gcaaagccag agcagcggcc gtctctgcac agccggggca  1500
tgctggaccg ctcccgcctg gccctgtgca cgctcgtctt cctctgcctg tcctgcaacc  1560
ccttggcctc cttgctgggg gcccgggggc ttcccagccc ctcagatacc accagcgtct  1620
accatagccc tgggcgcaac gtgctgggca ccgagagcag agatggccct ggctgggccc  1680
agtggctgct gcccccagtg gtctggctgc tcaatgggct gttggtgctc gtctccttgg  1740
tgcttctctt tgtctacggt gagccagtca cacggcccca ctcaggcccc gccgtgtact  1800
tctggaggca tcgcaagcag gctgacctgg acctggcccg gggagacttt gcccaggctg  1860
cccagcagct gtggctggcc ctgcgggcac tgggccggcc cctgcccacc tcccacctgg  1920
acctggcttg tagcctcctc tggaacctca tccgtcacct gctgcagcgt ctctgggtgg  1980
gccgctggct ggcaggccgg gcagggggcc tgcagcagga ctgtgctctg cgagtggatg  2040
ctagcgccag cgcccgagac gcagccctgg tctaccataa gctgcaccag ctgcacacca  2100
tggggaagca cacaggcggg cacctcactg ccaccaacct ggcgctgagt gccctgaacc  2160
tggcagagtg tgcaggggat gccgtgtctg tggcgacgct ggccgagatc tatgtggcgg  2220
ctgcattgag agtgaagacc agtctcccac gggccttgca ttttctgaca cgcttcttcc  2280
tgagcagtgc ccgccaggcc tgcctggcac agagtggctc agtgcctcct gccatgcagt  2340
ggctctgcca ccccgtgggc caccgtttct tcgtggatgg ggactggtcc gtgctcagta  2400
ccccatggga gagcctgtac agcttggccg ggaacccagt ggacccccctg gcccaggtga  2460
ctcagctatt ccgggaacat ctcttagagc gagcactgaa ctgtgtgacc cagcccaacc  2520
ccagccctgg gtcagctgat ggggacaagg aattctcgga tgccctcggg tacctgcagc  2580
tgctgaacag ctgttctgat gctgcggggg ctcctgccta cagcttctcc atcagttcca  2640
gcatggccac caccaccggc gtagacccgg tggccaagtg gtgggcctct ctgacagctg  2700
tggtgatcca ctggctgcgg cgggatgagg aggcggctga gcggctgtgc ccgctggtgg  2760
agcacctgcc ccgggtgctg caggagtctg agagacccct gcccagggca gctctgcact  2820
ccttcaaggc tgcccgggcc ctgctgggct gtgccaaggc agagtctggt ccagccagcc  2880
tgaccatctg tgagaaggcc agtgggtacc tgcaggacag cctggctacc acaccagcca  2940
gcagctccat tgacaaggcc gtgcagctgt tcctgtgtga cctgcttctt gtggtgcgca  3000
ccagcctgtg gcggcagcag cagcccccgg ccccggcccc agcagcccag ggcaccagca  3060
gcaggcccca ggcttccgcc cttgagctgc gtggcttcca acgggacctg agcagcctga  3120
ggcggctggc acagagcttc cggcccgcca tgcggagggt gttcctacat gaggccacgg  3180
cccggctgat ggcgggggcc agccccacac ggacacacca gctcctcgac cgcagtctga  3240
ggcggcgggc aggccccggt ggcaaaggag gcgcggtggc ggagctggag ccgcggccca  3300
cgcggcggga gcacgcggag gccttgctgc tggcctcctg ctacctgccc cccggcttcc  3360
tgtcggcgcc cgggcagcgc gtgggcatgc tggctgaggc ggcgcgcaca ctcgagaagc  3420
ttggcgatcg ccggctgctg cacgactgtc agcagatgct catgcgcctg ggcggtggga  3480
ccactgtcac ttccagctag accccgtgtc cccggcctca gcacccctgt ctctagccac  3540
tttggtcccg tgcagcttct gtcctgcgtc gaagctttga aggccgaagg cagtgcaaga  3600
gactctggcc tccacagttc gacctgcggc tgctgtgtgc cttcgcggtg gaaggcccga  3660
ggggcgcgat cttgacccta agaccggcgg ccatgatggt gctgacctct ggtggccgat  3720
cggggcactg caggggccga gccattttgg ggggcccccc tccttgctct gcaggcacct  3780
tagtggcttt tttcctcctg tgtacaggga agagaggggt acatttccct gtgctgacgg  3840
aagccaactt ggctttcccg gactgcaagc agggctctgc cccagaggcc tctctctccg  3900
tcgtgggaga gagacgtgta catagtgtag gtcagcgtgc ttagcctcct gacctgaggc  3960
tcctgtgcta ctttgccttt tgcaaacttt attttcatag attgagaagt tttgtacaga  4020
gaattaaaaa tgaaattatt tataatctgg aaaaaa                            4056

SEQ ID NO: 12          moltype = DNA  length = 4178
FEATURE                Location/Qualifiers
source                 1..4178
```

```
                        mol_type = other DNA
                        organism = Homo sapiens
SEQUENCE: 12
gcggccgggg gaacccagtt tccgaggaac ttttcgccgg cgccgggccg cctctgaggc  60
cagggcagga cacgaacgcg cggagcggcg gcggcgactg agagccgggg ccgcggcggc  120
gctccctagg aagggccgta cgaggcggcg ggcccggcgg gcctcccgga ggaggcggct  180
gcgccatgga cgagccaccc ttcagcgagg cggctttgga gcaggcgctg ggcgagccgt  240
gcgatctgga cgcggcgctg ctgaccgaca tcgaagacat gcttcagctt atcaacaacc  300
aagacagtga cttccctggc ctatttgacc caccctatgc tgggagtggg gcagggggca  360
cagaccctgc cagccccgat accagctccc caggcagctt gtctccacct cctgccacat  420
tgagctcctc tcttgaagcc ttcctgagcg ggccgcaggc agcgccctca cccctgtccc  480
ctccccagcc tgcacccact ccattgaaga tgtacccgtc catgcccgct ttctcccctg  540
ggcctggtat caaggaagag tcagtgccac tgagcatcct gcagaccccc accccacagc  600
ccctgccagg ggccctcctg ccacagagct tcccagcccc agccccaccg cagttcagct  660
ccacccctgt gttaggctac cccagccctc cgggaggctt ctctacagga agccctcccg  720
ggaacaccca gcagccgctg cctggcctgc cactggcttc cccgccaggg gtcccgcccg  780
tctccttgca cacccaggtc cagagtgtgg tcccccagca gctactgaca gtcacagctg  840
cccccacggc agcccctgta acgaccactg tgacctcgca gatccagcag gtcccggtcc  900
tgctgcagcc ccacttcatc aaggcagact cgctgcttct gacagccatg aagacagacg  960
gagccactgt gaaggcggca ggtctcagtc ccctggtctc tggcaccact gtgcagacag  1020
ggcctttgcc gaccctggtg agtggcggaa ccatcttggc aacagtccca ctggtcgtag  1080
atgcggagaa gctgcctatc aaccggctcg cagctggcag caaggccccg gcctctgccc  1140
agagccgtgg agagaagcgc acagcccaca acgccattga gaagtgctac cgctcctcca  1200
tcaatgacaa aatcattgag ctcaaggatc tggtggtggg cactgaggca aagctgaata  1260
aatctgctgt cttgcgcaag gccatcgact acattcgctt tctgcaacac agcaaccaga  1320
aactcaagca ggagaaccta agtctgcgca ctgctgtcca caaaagcaaa tctctgaagg  1380
atctggtgtc ggcctgtggc agtggaggga acacagacgt gctcatggag ggcgtgaaga  1440
ctgaggtgga ggacacactg accccacccc cctcggatgc tggctcacct ttccagagca  1500
gccccttgtc ccttggcagc aggggcagtg gcagcggtgg cagtggcagt gactcggagc  1560
ctgacagccc agtctttgag gacagcaagg caaagccaga gcagcggccg tctctgcaca  1620
gccggggcat gctggaccgc tcccgcctgg ccctgtgcac gctcgtcttc ctctgcctgt  1680
cctgcaaccc cttggcctcc ttgctggggg cccgggggct tcccagcccc tcagatacca  1740
ccagcgtcta ccatagccct gggcgcaacg tgctgggcac cgagagcaga gatggccctg  1800
gctgggccca gtggctgctg cccccagtgg tctggctgct caatgggctg ttggtgctcg  1860
tctccttggt gcttctcttt gtctacggtg agccagtcac acggccccac tcaggccccg  1920
ccgtgtactt ctggaggcat cgcaagcagg ctgacctgga cctggcccgg ggagactttg  1980
cccaggctgc ccagcagctg tggctggccc tgcgggcact gggccggccc ctgcccacct  2040
cccacctgga cctggcttgt agcctcctct ggaacctcat ccgtcacctg ctgcagcgtc  2100
tctgggtggg ccgctggctg gcaggccggg caggggggcct gcagcaggac tgtgctctgc  2160
gagtggatgc tagcgccagc gcccgagacg cagccctggt ctaccataag ctgcaccagc  2220
tgcacaccat ggggaagcac acaggcgggc acctcactgc caccaacctg gcgctgagtg  2280
ccctgaacct ggcagagtgt gcaggggatg ccgtgtctgt ggcgacgctg gccgagatct  2340
atgtggcggc tgcattgaga gtgaagacca gtctcccacg ggccttgcat tttctgacac  2400
gcttcttcct gagcagtgcc cgccaggcct gcctggcaca gagtggctca gtgcctcctg  2460
ccatgcagtg gctctgccac cccgtgggcc accgtttctt cgtggatggg gactggtccg  2520
tgctcagtac cccatgggag agcctgtaca gcttggccgg gaacccagtg gacccccctgg  2580
cccaggtgac tcagctattc cgggaacatc tcttagagcg agcactgaac tgtgtgaccc  2640
agcccaaccc cagccctggg tcagctgatg gggacaagga attctcggat gccctcgggt  2700
acctgcagct gctgaacagc tgttctgatg ctgcgggggc tcctgcctac agcttctcca  2760
tcagttccag catggccacc accaccggcg tagacccggt ggccaagtgg tgggcctctc  2820
tgacagctgt ggtgatccac tggctgcggc gggatgagga ggcggctgag cggctgtgcc  2880
cgctggtgga gcacctgccc cgggtgctgc aggagtctga gagacccctg cccagggcag  2940
ctctgcactc cttcaaggct gcccgggccc tgctgggctg tgccaaggca gagtctggtc  3000
cagccagcct gaccatctgt gagaaggcca gtgggtacct gcaggacagc ctggctacca  3060
caccagccag cagctccatt gacaaggccg tgcagctgtt cctgtgtgac ctgcttcttg  3120
tggtgcgcac cagcctgtgg cggcagcagc agcccccggc cccggcccca gcagcccagg  3180
gcaccagcag caggccccag gcttccgccc ttgagctgcg tggcttccaa cgggacctga  3240
gcagcctgag gcggctggca cagagcttcc ggcccgccat gcggagggtg ttcctacatg  3300
aggccacggc ccggctgatg gcgggggcca gccccacacg gacacaccag ctcctcgacc  3360
gcagtctgag gcggcgggca ggccccggtg gcaaaggagg cgcggtggcg gagctggagc  3420
cgcggcccac gcggcgggag cacgcggagg ccttgctgct ggcctcctgc tacctgcccc  3480
ccggcttcct gtcggcgccc gggcagcgcg tgggcatgct ggctgaggcg gcgcgcacac  3540
tcgagaagct tggcgatcgc cggctgctgc acgactgtca gcagatgctc atgcgcctgg  3600
gcggtgggac cactgtcact tccagctaga ccccgtgtcc ccggcctcag cacccctgtc  3660
tctagccact ttggtcccgt gcagcttctg tcctgcgtcg aagctttgaa ggccgaaggc  3720
agtgcaagag actctggcct ccacagttcg acctgcggct gctgtgtgcc ttcgcggtgg  3780
aaggcccgag gggcgcgatc ttgaccctaa gaccggcggc catgatggtg ctgacctctg  3840
gtggccgatc ggggcactgc aggggccgag ccattttggg gggcccccct ccttgctctg  3900
caggcacctt agtggctttt ttcctcctgt gtacagggaa gagaggggta catttccctg  3960
tgctgacgga agccaacttg gctttcccgg actgcaagca gggctctgcc ccagaggcct  4020
ctctctccgt cgtgggagag agacgtgtac atagtgtagg tcagcgtgct tagcctcctg  4080
acctgaggct cctgtgctac tttgcctttt gcaaacttta ttttcataga ttgagaagtt  4140
ttgtacagag aattaaaaat gaaattattt ataatctg                         4178

SEQ ID NO: 13           moltype = DNA  length = 4253
FEATURE                 Location/Qualifiers
source                  1..4253
                        mol_type = other DNA
                        organism = Homo sapiens
```

SEQUENCE: 13
cagtttccga ggaacttttc gccggcgccg ggccgcctct gaggccaggg caggacacga 60
acgcgcggag cggcggcggc gactgagagc cggggccgcg gcggcgctcc ctaggaaggg 120
ccgtacgagg cggcgggccc ggcgggcctc ccggaggagg cggctgcgcc atggacgagc 180
caccccttcag cgaggcggct ttggagcagg cgctgggcga gccgtgcgat ctggacgcgg 240
cgctgctgac cgacatcgaa ggtgaagtcg gcgcggggag gggtagggcc aacggcctgg 300
acgccccaag ggcgggcgca gatcgcggag ccatggattg cactttcgaa gacatgcttc 360
agcttatcaa caaccaagac agtgacttcc ctggcctatt tgacccaccc tatgctggga 420
gtggggcagg gggcacagac cctgccagcc ccgataccag ctccccaggc agcttgtctc 480
cacctcctgc cacattgagc tcctctcttg aagccttcct gagcgggccg caggcagcgc 540
cctcacccct gtcccctccc cagcctgcac ccactccatt gaagatgtac ccgtccatgc 600
ccgctttctc ccctgggcct ggtatcaagg aagagtcagt gccactgagc atcctgcaga 660
cccccacccc acagcccctg ccaggggccc tcctgccaca gagcttccca gccccagccc 720
caccgcagtt cagctccacc cctgtgttag gctaccccag ccctccggga ggcttctcta 780
caggaagccc tcccgggaac acccagcagc cgctgcctgg cctgccactg gcttccccgc 840
caggggtccc gcccgtctcc ttgcacaccc aggtccagag tgtggtcccc cagcagctac 900
tgacagtcac agctgccccc acggcagccc ctgtaacgac cactgtgacc tcgcagatcc 960
agcaggtccc ggtcctgctg cagccccact tcatcaaggc agactcgctg cttctgacag 1020
ccatgaagac agacggagcc actgtgaagg cggcaggtct cagtcccctg gtctctggca 1080
ccactgtgca gacagggcct ttgccgaccc tggtgagtgg cggaaccatc ttggcaacag 1140
tcccactggt cgtagatgcg gagaagctgc ctatcaaccg gctcgcagct ggcagcaagg 1200
ccccggcctc tgcccagagc cgtggagaga agcgcacagc ccacaacgcc attgagaagt 1260
gctaccgctc ctccatcaat gacaaaatca ttgagctcaa ggatctggtg gtgggcactg 1320
aggcaaagct gaataaatct gctgtcttgc gcaaggccat cgactacatt cgctttctgc 1380
aacacagcaa ccagaaactc aagcaggaga acctaagtct gcgcactgct gtccacaaaa 1440
gcaaatctct gaaggatctg gtgtcggcct gtggcagtgg agggaacaca gacgtgctca 1500
tggagggcgt gaagactgag gtggaggaca cactgacccc accccccctcg gatgctggct 1560
cacctttcca gagcagcccc ttgtcccttg gcagcagggg cagtggcagc ggtggcagtg 1620
gcagtgactc ggagcctgac agcccagtct ttgaggacag caaggcaaag ccagagcagc 1680
ggccgtctct gcacagccgg ggcatgctgg accgctcccg cctggccctg tgcacgctcg 1740
tcttcctctg cctgtcctgc aacccccttgg cctccttgct gggggcccgg gggcttccca 1800
gcccctcaga taccaccagc gtctaccata gccctgggcg caacgtgctg ggcaccgaga 1860
gcagagatgg ccctggctgg gcccagtggc tgctgccccc agtggtctgg ctgctcaatg 1920
ggctgttggt gctcgtctcc ttggtgcttc tctttgtcta cggtgagcca gtcacacggc 1980
cccactcagg ccccgccgtg tacttctgga ggcatcgcaa gcaggctgac ctggacctgg 2040
cccggggaga ctttgcccag gctgcccagc agctgtggct ggccctgcgg gcactgggcc 2100
ggcccctgcc cacctcccac ctggacctgg cttgtagcct cctctggaac ctcatccgtc 2160
acctgctgca gcgtctctgg gtgggccgct ggctggcagg ccgggcaggg ggcctgcagc 2220
aggactgtgc tctgcgagtg gatgctagcg ccagcgcccg agacgcagcc ctggtctacc 2280
ataagctgca ccagctgcac accatgggga agcacacagg cgggcacctc actgccacca 2340
acctggcgct gagtgccctg aacctggcag agtgtgcagg ggatgccgtg tctgtggcga 2400
cgctggccga gatctatgtg gcggctgcat tgagagtgaa gaccagtctc ccacgggcct 2460
tgcattttct gacacgcttc ttcctgagca gtgcccgcca ggcctgcctg gcacagagtg 2520
gctcagtgcc tcctgccatg cagtggctct gccaccccgt gggccaccgt ttcttcgtgg 2580
atggggactg gtccgtgctc agtaccccat gggagagcct gtacagcttg gccgggaacc 2640
cagtggaccc cctggcccag gtgactcagc tattccggga acatctctta gagcgagcac 2700
tgaactgtgt gacccagccc aaccccagcc ctgggtcagc tgatggggac aaggaattct 2760
cggatgccct cgggtacctg cagctgctga acagctgttc tgatgctgcg ggggctcctg 2820
cctacagctt ctccatcagt tccagcatgg ccaccaccac cggcgtagac ccggtggcca 2880
agtggtgggc ctctctgaca gctgtggtga tccactggct gcggcgggat gaggaggcgg 2940
ctgagcggct gtgcccgctg gtggagcacc tgccccgggt gctgcaggag tctgagagac 3000
ccctgcccag ggcagctctg cactccttca aggctgcccg ggccctgctg ggctgtgcca 3060
aggcagagtc tggtccagcc agcctgacca tctgtgagaa ggccagtggg tacctgcagg 3120
acagcctggc taccacacca gccagcagct ccattgacaa ggccgtgcag ctgttcctgt 3180
gtgacctgct tcttgtggtg cgcaccagcc tgtggcggca gcagcagccc ccggccccgg 3240
ccccagcagc ccagggcacc agcagcaggc cccaggcttc cgcccttgag ctgcgtggct 3300
tccaacggga cctgagcagc ctgaggcggc tggcacagag cttccggccc gccatgcgga 3360
gggtgttcct acatgaggcc acggcccggc tgatggcggg ggccagcccc acacggacac 3420
accagctcct cgaccgcagt ctgaggcggc gggcaggccc cggtggcaaa ggaggcgcgg 3480
tggcggagct ggagccgcgg cccacgcggc gggagcacgc ggaggccttg ctgctggcct 3540
cctgctacct gccccccggc ttcctgtcgg cgcccgggca gcgcgtgggc atgctggctg 3600
aggcggcgcg cacactcgag aagcttggcg atcgccggct gctgcacgac tgtcagcaga 3660
tgctcatgcg cctgggcggt gggaccactg tcacttccag ctagacccg tgtccccggc 3720
ctcagcaccc ctgtctctag ccactttggt cccgtgcagc ttctgtcctg cgtcgaagct 3780
ttgaaggccg aaggcagtgc aagagactct ggcctccaca gttcgacctg cggctgctgt 3840
gtgccttcgc ggtggaaggc ccgaggggcg cgatcttgac cctaagaccg gcggccatga 3900
tggtgctgac ctctggtggc cgatcggggc actgcagggg ccgagccatt ttggggggcc 3960
cccctccttg ctctgcaggc accttagtgg cttttttcct cctgtgtaca gggaagagag 4020
gggtacattt ccctgtgctg acggaagcca acttggcttt cccggactgc aagcagggct 4080
ctgccccaga ggcctctctc tccgtcgtgg gagagagacg tgtacatagt gtaggtcagc 4140
gtgcttagcc tcctgacctg aggctcctgt gctactttgc cttttgcaaa ctttattttc 4200
atagattgag aagttttgta cagagaatta aaaatgaaat tatttataat ctg 4253

SEQ ID NO: 14 moltype = DNA length = 4056
FEATURE Location/Qualifiers
source 1..4056
mol_type = other DNA
organism = Homo sapiens
SEQUENCE: 14

```
gcggggcggg cgcgccgcag cgctcaacgg cttcaaaaat ccgccgcgcc ttgacaggtg  60
aagtcggcgc ggggaggggt agggccaacg gcctggacgc cccaagggcg ggcgcagatc  120
gcggagccat ggattgcact ttcgaagaca tgcttcagct tatcaacaac caagacagtg  180
acttccctgg cctatttgac ccaccctatg ctgggagtgg ggcagggggc acagaccctg  240
ccagccccga taccagctcc ccaggcagct tgtctccacc tcctgccaca ttgagctcct  300
ctcttgaagc cttcctgagc gggccgcagg cagcgccctc acccctgtcc cctccccagc  360
ctgcacccac tccattgaag atgtacccgt ccatgcccgc tttctcccct gggcctggta  420
tcaaggaaga gtcagtgcca ctgagcatcc tgcagacccc caccccacag cccctgccag  480
gggccctcct gccacagagc ttcccagccc cagccccacc gcagttcagc tccacccctg  540
tgttaggcta ccccagccct ccgggaggct tctctacagg aagccctccc gggaacaccc  600
agcagccgct gcctggcctg ccactggctt ccccgccagg ggtcccgccc gtctccttgc  660
acacccaggt ccagagtgtg gtcccccagc agctactgac agtcacagct gcccccacgg  720
cagcccctgt aacgaccact gtgacctcgc agatccagca ggtcccggtc ctgctgcagc  780
cccacttcat caaggcagac tcgctgcttc tgacagccat gaagacagac ggagccactg  840
tgaaggcggc aggtctcagt cccctggtct ctggcaccac tgtgcagaca gggcctttgc  900
cgaccctggt gagtggcgga accatcttgg caacagtccc actggtcgta gatgcggaga  960
agctgcctat caaccggctc gcagctggca gcaaggcccc ggcctctgcc cagagccgtg  1020
gagagaagcg cacagcccac aacgccattg agaagtgcta ccgctcctcc atcaatgaca  1080
aaatcattga gctcaaggat ctggtggtgg gcactgaggc aaagctgaat aaatctgctg  1140
tcttgcgcaa ggccatcgac tacattcgct ttctgcaaca cagcaaccag aaactcaagc  1200
aggagaacct aagtctgcgc actgctgtcc acaaaagcaa atctctgaag gatctggtgt  1260
cggcctgtgg cagtggaggg aacacagacg tgctcatgga gggcgtgaag actgaggtgg  1320
aggacacact gaccccaccc ccctcggatg ctggctcacc tttccagagc agccccttgt  1380
cccttggcag caggggcagt ggcagcggtg gcagtggcag tgactcggag cctgacagcc  1440
cagtctttga ggacagcaag gcaaagccag agcagcggcc gtctctgcac agccggggca  1500
tgctggaccg ctcccgcctg gccctgtgca cgctcgtctt cctctgcctg tcctgcaacc  1560
ccttggcctc cttgctgggg gcccgggggc ttcccagccc ctcagatacc accagcgtct  1620
accatagccc tgggcgcaac gtgctgggca ccgagagcag agatggccct ggctgggccc  1680
agtggctgct gcccccagtg gtctggctgc tcaatgggct gttggtgctc gtctccttgg  1740
tgcttctctt tgtctacggt gagccagtca cacggcccca ctcaggcccc gccgtgtact  1800
tctggaggca tcgcaagcag gctgacctgg acctggcccg gggagacttt gcccaggctg  1860
cccagcagct gtggctggcc ctgcgggcac tgggccggcc cctgcccacc tcccacctgg  1920
acctggcttg tagcctcctc tggaacctca tccgtcacct gctgcagcgt ctctgggtgg  1980
gccgctggct ggcaggccgg gcagggggcc tgcagcagga ctgtgctctg cgagtggatg  2040
ctagcgccag cgcccgagac gcagccctgg tctaccataa gctgcaccag ctgcacacca  2100
tggggaagca cacaggcggg cacctcactg ccaccaacct ggcgctgagt gccctgaacc  2160
tggcagagtg tgcaggggat gccgtgtctg tggcgacgct ggccgagatc tatgtggcgg  2220
ctgcattgag agtgaagacc agtctcccac gggccttgca ttttctgaca cgcttcttcc  2280
tgagcagtgc ccgccaggcc tgcctggcac agagtggctc agtgcctcct gccatgcagt  2340
ggctctgcca ccccgtgggc caccgtttct tcgtggatgg ggactggtcc gtgctcagta  2400
ccccatggga gagcctgtac agcttggccg ggaacccagt ggacccccctg gcccaggtga  2460
ctcagctatt ccgggaacat ctcttagagc gagcactgaa ctgtgtgacc cagcccaacc  2520
ccagccctgg gtcagctgat ggggacaagg aattctcgga tgccctcggg tacctgcagc  2580
tgctgaacag ctgttctgat gctgcggggg ctcctgccta cagcttctcc atcagttcca  2640
gcatggccac caccaccggc gtagacccgg tggccaagtg gtgggcctct ctgacagctg  2700
tggtgatcca ctggctgcgg cgggatgagg aggcggctga gcggctgtgc ccgctggtgg  2760
agcacctgcc ccgggtgctg caggagtctg agagacccct gcccagggca gctctgcact  2820
ccttcaaggc tgcccgggcc ctgctgggct gtgccaaggc agagtctggt ccagccagcc  2880
tgaccatctg tgagaaggcc agtgggtacc tgcaggacag cctggctacc acaccagcca  2940
gcagctccat tgacaaggcc gtgcagctgt tcctgtgtga cctgcttctt gtggtgcgca  3000
ccagcctgtg gcggcagcag cagcccccgg ccccggcccc agcagcccag ggcaccagca  3060
gcaggcccca ggcttccgcc cttgagctgc gtggcttcca acgggacctg agcagcctga  3120
ggcggctggc acagagcttc cggcccgcca tgcggagggt gttcctacat gaggccacgg  3180
cccggctgat ggcgggggcc agccccacac ggacacacca gctcctcgac cgcagtctga  3240
ggcggcgggc aggccccggt ggcaaaggag gcgcggtggc ggagctggag ccgcggccca  3300
cgcggcggga gcacgcggag gccttgctgc tggcctcctg ctacctgccc cccggcttcc  3360
tgtcggcgcc cgggcagcgc gtgggcatgc tggctgaggc ggcgcgcaca ctcgagaagc  3420
ttggcgatcg ccggctgctg cacgactgtc agcagatgct catgcgcctg ggcggtggga  3480
ccactgtcac ttccagctag accccgtgtc cccggcctca gcacccctgt ctctagccac  3540
tttggtcccg tgcagcttct gtcctgcgtc gaagctttga aggccgaagg cagtgcaaga  3600
gactctggcc tccacagttc gacctgcggc tgctgtgtgc cttcgcggtg gaaggcccga  3660
ggggcgcgat cttgacccta agaccggcgg ccatgatggt gctgacctct ggtggccgat  3720
cggggcactg caggggccga gccattttgg ggggcccccc tccttgctct gcaggcacct  3780
tagtggcttt tttcctcctg tgtacaggga agagaggggt acatttccct gtgctgacgg  3840
aagccaactt ggctttcccg gactgcaagc agggctctgc cccagaggcc tctctctccg  3900
tcgtgggaga gagacgtgta catagtgtag gtcagcgtgc ttagcctcct gacctgaggc  3960
tcctgtgcta ctttgccttt tgcaaacttt attttcatag attgagaagt tttgtacaga  4020
gaattaaaaa tgaaattatt tataatctgg aaaaaa                             4056

SEQ ID NO: 15          moltype = AA  length = 1147
FEATURE                Location/Qualifiers
source                 1..1147
                       mol_type = protein
                       organism = Homo sapiens
SEQUENCE: 15
MDEPPFSEAA LEQALGEPCD LDAALLTDIE DMLQLINNQD SDFPGLFDPP YAGSGAGGTD  60
PASPDTSSPG SLSPPPATLS SSLEAFLSGP QAAPSPLSPP QPAPTPLKMY PSMPAFSPGP  120
GIKEESVPLS ILQTPTPQPL PGALLPQSFP APAPPQFSST PVLGYPSPPG GFSTGSPPGN  180
TQQPLPGLPL ASPPGVPPVS LHTQVQSVVP QQLLTVTAAP TAAPVTTTVT SQIQQVPVLL  240
```

-continued

```
QPHFIKADSL LLTAMKTDGA TVKAAGLSPL VSGTTVQTGP LPTLVSGGTI LATVPLVVDA  300
EKLPINRLAA GSKAPASAQS RGEKRTAHNA IEKRYRSSIN DKIIELKDLV VGTEAKLNKS  360
AVLRKAIDYI RFLQHSNQKL KQENLSLRTA VHKSKSLKDL VSACGSGGNT DVLMEGVKTE  420
VEDTLTPPPS DAGSPFQSSP LSLGSRGSGS GGSGSDSEPD SPVFEDSKAK PEQRPSLHSR  480
GMLDRSRLAL CTLVFLCLSC NPLASLLGAR GLPSPSDTTS VYHSPGRNVL GTESRDGPGW  540
AQWLLPPVVW LLNGLLVLVS LVLLFVYGEP VTRPHSGPAV YFWRHRKQAD LDLARGDFAQ  600
AAQQLWLALR ALGRPLPTSH LDLACSLLWN LIRHLLQRLW VGRWLAGRAG GLQQDCALRV  660
DASASARDAA LVYHKLHQLH TMGKHTGGHL TATNLALSAL NLAECAGDAV SVATLAEIYV  720
AAALRVKTSL PRALHFLTRF FLSSARQACL AQSGSVPPAM QWLCHPVGHR FFVDGDWSVL  780
STPWESLYSL AGNPVDPLAQ VTQLFREHLL ERALNCVTQP NPSPGSADGD KEFSDALGYL  840
QLLNSCSDAA GAPAYSFSIS SSMATTTGVD PVAKWWASLT AVVIHWLRRD EEAAERLCPL  900
VEHLPRVLQE SERPLPRAAL HSFKAARALL GCAKAESGPA SLTICEKASG YLQDSLATTP  960
ASSSIDKAVQ LFLCDLLLVV RTSLWRQQQP PAPAPAAQGT SSRPQASALE LRGFQRDLSS  1020
LRRLAQSFRP AMRRVFLHEA TARLMAGASP TRTHQLLDRS LRRRAGPGGK GGAVAELEPR  1080
PTRREHAEAL LLASCYLPPG FLSAPGQRVG MLAEAARTLE KLGDRRLLHD CQQMLMRLGG  1140
GTTVTSS                                                            1147

SEQ ID NO: 16          moltype = AA  length = 1177
FEATURE                Location/Qualifiers
source                 1..1177
                       mol_type = protein
                       organism = Homo sapiens
SEQUENCE: 16
MDEPPFSEAA LEQALGEPCD LDAALLTDIE GEVGAGRGRA NGLDAPRAGA DRGAMDCTFE  60
DMLQLINNQD SDFPGLFDPP YAGSGAGGTD PASPDTSSPG SLSPPPATLS SSLEAFLSGP  120
QAAPSPLSPP QPAPTPLKMY PSMPAFSPGP GIKEESVPLS ILQTPTPQPL PGALLPQSFP  180
APAPPQFSST PVLGYPSPPG GFSTGSPPGN TQQPLPGLPL ASPPGVPPVS LHTQVQSVVP  240
QQLLTVTAAP TAAPVTTTVT SQIQQVPVLL QPHFIKADSL LLTAMKTDGA TVKAAGLSPL  300
VSGTTVQTGP LPTLVSGGTI LATVPLVVDA EKLPINRLAA GSKAPASAQS RGEKRTAHNA  360
IEKRYRSSIN DKIIELKDLV VGTEAKLNKS AVLRKAIDYI RFLQHSNQKL KQENLSLRTA  420
VHKSKSLKDL VSACGSGGNT DVLMEGVKTE VEDTLTPPPS DAGSPFQSSP LSLGSRGSGS  480
GGSGSDSEPD SPVFEDSKAK PEQRPSLHSR GMLDRSRLAL CTLVFLCLSC NPLASLLGAR  540
GLPSPSDTTS VYHSPGRNVL GTESRDGPGW AQWLLPPVVW LLNGLLVLVS LVLLFVYGEP  600
VTRPHSGPAV YFWRHRKQAD LDLARGDFAQ AAQQLWLALR ALGRPLPTSH LDLACSLLWN  660
LIRHLLQRLW VGRWLAGRAG GLQQDCALRV DASASARDAA LVYHKLHQLH TMGKHTGGHL  720
TATNLALSAL NLAECAGDAV SVATLAEIYV AAALRVKTSL PRALHFLTRF FLSSARQACL  780
AQSGSVPPAM QWLCHPVGHR FFVDGDWSVL STPWESLYSL AGNPVDPLAQ VTQLFREHLL  840
ERALNCVTQP NPSPGSADGD KEFSDALGYL QLLNSCSDAA GAPAYSFSIS SSMATTTGVD  900
PVAKWWASLT AVVIHWLRRD EEAAERLCPL VEHLPRVLQE SERPLPRAAL HSFKAARALL  960
GCAKAESGPA SLTICEKASG YLQDSLATTP ASSSIDKAVQ LFLCDLLLVV RTSLWRQQQP  1020
PAPAPAAQGT SSRPQASALE LRGFQRDLSS LRRLAQSFRP AMRRVFLHEA TARLMAGASP  1080
TRTHQLLDRS LRRRAGPGGK GGAVAELEPR PTRREHAEAL LLASCYLPPG FLSAPGQRVG  1140
MLAEAARTLE KLGDRRLLHD CQQMLMRLGG GTTVTSS                           1177

SEQ ID NO: 17          moltype = AA  length = 1123
FEATURE                Location/Qualifiers
source                 1..1123
                       mol_type = protein
                       organism = Homo sapiens
SEQUENCE: 17
MDCTFEDMLQ LINNQDSDFP GLFDPPYAGS GAGGTDPASP DTSSPGSLSP PPATLSSSLE  60
AFLSGPQAAP SPLSPPQPAP TPLKMYPSMP AFSPGPGIKE ESVPLSILQT PTPQPLPGAL  120
LPQSFPAPAP PQFSSTPVLG YPSPPGGFST GSPPGNTQQP LPGLPLASPP GVPPVSLHTQ  180
VQSVVPQQLL TVTAAPTAAP VTTTVTSQIQ QVPVLLQPHF IKADSLLLTA MKTDGATVKA  240
AGLSPLVSGT TVQTGPLPTL VSGGTILATV PLVVDAEKLP INRLAAGSKA PASAQSRGEK  300
RTAHNAIEKR YRSSINDKII ELKDLVVGTE AKLNKSAVLR KAIDYIRFLQ HSNQKLKQEN  360
LSLRTAVHKS KSLKDLVSAC GSGGNTDVLM EGVKTEVEDT LTPPPSDAGS PFQSSPLSLG  420
SRGSGSGGSG SDSEPDSPVF EDSKAKPEQR PSLHSRGMLD RSRLALCTLV FLCLSCNPLA  480
SLLGARGLPS PSDTTSVYHS PGRNVLGTES RDGPGWAQWL LPPVVWLLNG LLVLVSLVLL  540
FVYGEPVTRP HSGPAVYFWR HRKQADLDLA RGDFAQAAQQ LWLALRALGR PLPTSHLDLA  600
CSLLWNLIRH LLQRLWVGRW LAGRAGGLQQ DCALRVDASA SARDAALVYH KLHQLHTMGK  660
HTGGHLTATN LALSALNLAE CAGDAVSVAT LAEIYVAAAL RVKTSLPRAL HFLTRFFLSS  720
ARQACLAQSG SVPPAMQWLC HPVGHRFFVD GDWSVLSTPW ESLYSLAGNP VDPLAQVTQL  780
FREHLLERAL NCVTQPNPSP GSADGDKEFS DALGYLQLLN SCSDAAGAPA YSFSISSSMA  840
TTTGVDPVAK WWASLTAVVI HWLRRDEEAA ERLCPLVEHL PRVLQESERP LPRAALHSFK  900
AARALLGCAK AESGPASLTI CEKASGYLQD SLATTPASSS IDKAVQLFLC DLLLVVRTSL  960
WRQQQPPAPA PAAQGTSSRP QASALELRGF QRDLSSLRRL AQSFRPAMRR VFLHEATARL  1020
MAGASPTRTH QLLDRSLRRR AGPGGKGGAV AELEPRPTRR EHAEALLLAS CYLPPGFLSA  1080
PGQRVGMLAE AARTLEKLGD RRLLHDCQQM LMRLGGGTTV TSS                    1123

SEQ ID NO: 18          moltype = AA  length = 1147
FEATURE                Location/Qualifiers
source                 1..1147
                       mol_type = protein
                       organism = Homo sapiens
SEQUENCE: 18
MDEPPFSEAA LEQALGEPCD LDAALLTDIE DMLQLINNQD SDFPGLFDPP YAGSGAGGTD  60
PASPDTSSPG SLSPPPATLS SSLEAFLSGP QAAPSPLSPP QPAPTPLKMY PSMPAFSPGP  120
GIKEESVPLS ILQTPTPQPL PGALLPQSFP APAPPQFSST PVLGYPSPPG GFSTGSPPGN  180
```

```
TQQPLPGLPL ASPPGVPPVS LHTQVQSVVP QQLLTVTAAP TAAPVTTTVT SQIQQVPVLL  240
QPHFIKADSL LLTAMKTDGA TVKAAGLSPL VSGTTVQTGP LPTLVSGGTI LATVPLVVDA  300
EKLPINRLAA GSKAPASAQS RGEKRTAHNA IEKCYRSSIN DKIIELKDLV VGTEAKLNKS  360
AVLRKAIDYI RFLQHSNQKL KQENLSLRTA VHKSKSLKDL VSACGSGGNT DVLMEGVKTE  420
VEDTLTPPPS DAGSPFQSSP LSLGSRGSGS GGSGSDSEPD SPVFEDSKAK PEQRPSLHSR  480
GMLDRSRLAL CTLVFLCLSC NPLASLLGAR GLPSPSDTTS VYHSPGRNVL GTESRDGPGW  540
AQWLLPPVVW LLNGLLVLVS LVLLFVYGEP VTRPHSGPAV YFWRHRKQAD LDLARGDFAQ  600
AAQQLWLALR ALGRPLPTSH LDLACSLLWN LIRHLLQRLW VGRWLAGRAG GLQQDCALRV  660
DASASARDAA LVYHKLHQLH TMGKHTGGHL TATNLALSAL NLAECAGDAV SVATLAEIYV  720
AAALRVKTSL PRALHFLTRF FLSSARQACL AQSGSVPPAM QWLCHPVGHR FFVDGDWSVL  780
STPWESLYSL AGNPVDPLAQ VTQLFREHLL ERALNCVTQP NPSPGSADGD KEFSDALGYL  840
QLLNSCSDAA GAPAYSFSIS SSMATTTGVD PVAKWWASLT AVVIHWLRRD EEAAERLCPL  900
VEHLPRVLQE SERPLPRAAL HSFKAARALL GCAKAESGPA SLTICEKASG YLQDSLATTP  960
ASSSIDKAVQ LFLCDLLLVV RTSLWRQQQP PAPAPAAQGT SSRPQASALE LRGFQRDLSS  1020
LRRLAQSFRP AMRRVFLHEA TARLMAGASP TRTHQLLDRS LRRRAGPGGK GGAVAELEPR  1080
PTRREHAEAL LLASCYLPPG FLSAPGQRVG MLAEAARTLE KLGDRRLLHD CQQMLMRLGG  1140
GTTVTSS                                                            1147

SEQ ID NO: 19          moltype = AA  length = 1177
FEATURE                Location/Qualifiers
source                 1..1177
                       mol_type = protein
                       organism = Homo sapiens
SEQUENCE: 19
MDEPPFSEAA LEQALGEPCD LDAALLTDIE GEVGAGRGRA NGLDAPRAGA DRGAMDCTFE  60
DMLQLINNQD SDFPGLFDPP YAGSGAGGTD PASPDTSSPG SLSPPPATLS SSLEAFLSGP  120
QAAPSPLSPP QPAPTPLKMY PSMPAFSPGP GIKEESVPLS ILQTPTPQPL PGALLPQSFP  180
APAPPQFSST PVLGYPSPPG GFSTGSPPGN TQQPLPGLPL ASPPGVPPVS LHTQVQSVVP  240
QQLLTVTAAP TAAPVTTTVT SQIQQVPVLL QPHFIKADSL LLTAMKTDGA TVKAAGLSPL  300
VSGTTVQTGP LPTLVSGGTI LATVPLVVDA EKLPINRLAA GSKAPASAQS RGEKRTAHNA  360
IEKCYRSSIN DKIIELKDLV VGTEAKLNKS AVLRKAIDYI RFLQHSNQKL KQENLSLRTA  420
VHKSKSLKDL VSACGSGGNT DVLMEGVKTE VEDTLTPPPS DAGSPFQSSP LSLGSRGSGS  480
GGSGSDSEPD SPVFEDSKAK PEQRPSLHSR GMLDRSRLAL CTLVFLCLSC NPLASLLGAR  540
GLPSPSDTTS VYHSPGRNVL GTESRDGPGW AQWLLPPVVW LLNGLLVLVS LVLLFVYGEP  600
VTRPHSGPAV YFWRHRKQAD LDLARGDFAQ AAQQLWLALR ALGRPLPTSH LDLACSLLWN  660
LIRHLLQRLW VGRWLAGRAG GLQQDCALRV DASASARDAA LVYHKLHQLH TMGKHTGGHL  720
TATNLALSAL NLAECAGDAV SVATLAEIYV AAALRVKTSL PRALHFLTRF FLSSARQACL  780
AQSGSVPPAM QWLCHPVGHR FFVDGDWSVL STPWESLYSL AGNPVDPLAQ VTQLFREHLL  840
ERALNCVTQP NPSPGSADGD KEFSDALGYL QLLNSCSDAA GAPAYSFSIS SSMATTTGVD  900
PVAKWWASLT AVVIHWLRRD EEAAERLCPL VEHLPRVLQE SERPLPRAAL HSFKAARALL  960
GCAKAESGPA SLTICEKASG YLQDSLATTP ASSSIDKAVQ LFLCDLLLVV RTSLWRQQQP  1020
PAPAPAAQGT SSRPQASALE LRGFQRDLSS LRRLAQSFRP AMRRVFLHEA TARLMAGASP  1080
TRTHQLLDRS LRRRAGPGGK GGAVAELEPR PTRREHAEAL LLASCYLPPG FLSAPGQRVG  1140
MLAEAARTLE KLGDRRLLHD CQQMLMRLGG GTTVTSS                          1177

SEQ ID NO: 20          moltype = AA  length = 1123
FEATURE                Location/Qualifiers
source                 1..1123
                       mol_type = protein
                       organism = Homo sapiens
SEQUENCE: 20
MDCTFEDMLQ LINNQDSDFP GLFDPPYAGS GAGGTDPASP DTSSPGSLSP PPATLSSSLE  60
AFLSGPQAAP SPLSPPQPAP TPLKMYPSMP AFSPGPGIKE ESVPLSILQT PTPQPLPGAL  120
LPQSFPAPAP PQFSSTPVLG YPSPPGGFST GSPPGNTQQP LPGLPLASPP GVPPVSLHTQ  180
VQSVVPQQLL TVTAAPTAAP VTTTVTSQIQ QVPVLLQPHF IKADSLLLTA MKTDGATVKA  240
AGLSPLVSGT TVQTGPLPTL VSGGTILATV PLVVDAEKLP INRLAAGSKA PASAQSRGEK  300
RTAHNAIEKC YRSSINDKII ELKDLVVGTE AKLNKSAVLR KAIDYIRFLQ HSNQKLKQEN  360
LSLRTAVHKS KSLKDLVSAC GSGGNTDVLM EGVKTEVEDT LTPPPSDAGS PFQSSPLSLG  420
SRGSGSGGSG SDSEPDSPVF EDSKAKPEQR PSLHSRGMLD RSRLALCTLV FLCLSCNPLA  480
SLLGARGLPS PSDTTSVYHS PGRNVLGTES RDGPGWAQWL LPPVVWLLNG LLVLVSLVLL  540
FVYGEPVTRP HSGPAVYFWR HRKQADLDLA RGDFAQAAQQ LWLALRALGR PLPTSHLDLA  600
CSLLWNLIRH LLQRLWVGRW LAGRAGGLQQ DCALRVDASA SARDAALVYH KLHQLHTMGK  660
HTGGHLTATN LALSALNLAE CAGDAVSVAT LAEIYVAAAL RVKTSLPRAL HFLTRFFLSS  720
ARQACLAQSG SVPPAMQWLC HPVGHRFFVD GDWSVLSTPW ESLYSLAGNP VDPLAQVTQL  780
FREHLLERAL NCVTQPNPSP GSADGDKEFS DALGYLQLLN SCSDAAGAPA YSFSISSSMA  840
TTTGVDPVAK WWASLTAVVI HWLRRDEEAA ERLCPLVEHL PRVLQESERP LPRAALHSFK  900
AARALLGCAK AESGPASLTI CEKASGYLQD SLATTPASSS IDKAVQLFLC DLLLVVRTSL  960
WRQQQPPAPA PAAQGTSSRP QASALELRGF QRDLSSLRRL AQSFRPAMRR VFLHEATARL  1020
MAGASPTRTH QLLDRSLRRR AGPGGKGGAV AELEPRPTRR EHAEALLLAS CYLPPGFLSA  1080
PGQRVGMLAE AARTLEKLGD RRLLHDCQQM LMRLGGGTTV TSS                   1123

SEQ ID NO: 21          moltype = DNA  length = 23
FEATURE                Location/Qualifiers
misc_feature           1..23
                       note = Guide RNA Recognition Sequence Near SREBF1 Variation
source                 1..23
                       mol_type = other DNA
                       organism = synthetic construct
SEQUENCE: 21
```

```
tctccgcatc tacgaccagt ggg                                          23

SEQ ID NO: 22          moltype = DNA  length = 23
FEATURE                Location/Qualifiers
misc_feature           1..23
                       note = Guide RNA Recognition Sequence Near SREBF1 Variation
source                 1..23
                       mol_type = other DNA
                       organism = synthetic construct
SEQUENCE: 22
ccagctgcga gccggttgat agg                                          23

SEQ ID NO: 23          moltype = DNA  length = 23
FEATURE                Location/Qualifiers
misc_feature           1..23
                       note = Guide RNA Recognition Sequence Near SREBF1 Variation
source                 1..23
                       mol_type = other DNA
                       organism = synthetic construct
SEQUENCE: 23
ttctccgcat ctacgaccag tgg                                          23

SEQ ID NO: 24          moltype = DNA  length = 23
FEATURE                Location/Qualifiers
misc_feature           1..23
                       note = Guide RNA Recognition Sequence Near SREBF1 Variation
source                 1..23
                       mol_type = other DNA
                       organism = synthetic construct
SEQUENCE: 24
agtcccactg gtcgtagatg cgg                                          23

SEQ ID NO: 25          moltype = DNA  length = 23
FEATURE                Location/Qualifiers
misc_feature           1..23
                       note = Guide RNA Recognition Sequence Near SREBF1 Variation
source                 1..23
                       mol_type = other DNA
                       organism = synthetic construct
SEQUENCE: 25
cctatcaacc ggctcgcagc tgg                                          23

SEQ ID NO: 26          moltype = DNA  length = 23
FEATURE                Location/Qualifiers
misc_feature           1..23
                       note = Guide RNA Recognition Sequence Near SREBF1 Variation
source                 1..23
                       mol_type = other DNA
                       organism = synthetic construct
SEQUENCE: 26
cggagaagct gcctatcaac cgg                                          23

SEQ ID NO: 27          moltype = DNA  length = 23
FEATURE                Location/Qualifiers
misc_feature           1..23
                       note = Guide RNA Recognition Sequence Near SREBF1 Variation
source                 1..23
                       mol_type = other DNA
                       organism = synthetic construct
SEQUENCE: 27
tgcgcttctc tccacggctc tgg                                          23

SEQ ID NO: 28          moltype = DNA  length = 23
FEATURE                Location/Qualifiers
misc_feature           1..23
                       note = Guide RNA Recognition Sequence Near SREBF1 Variation
source                 1..23
                       mol_type = other DNA
                       organism = synthetic construct
SEQUENCE: 28
gcgcttctct ccacggctct ggg                                          23

SEQ ID NO: 29          moltype = DNA  length = 23
FEATURE                Location/Qualifiers
misc_feature           1..23
                       note = Guide RNA Recognition Sequence Near SREBF1 Variation
source                 1..23
                       mol_type = other DNA
                       organism = synthetic construct
```

```
SEQUENCE: 29
aatcattgag ctcaaggatc tgg                                          23

SEQ ID NO: 30          moltype = DNA  length = 23
FEATURE                Location/Qualifiers
misc_feature           1..23
                       note = Guide RNA Recognition Sequence Near SREBF1 Variation
source                 1..23
                       mol_type = other DNA
                       organism = synthetic construct
SEQUENCE: 30
ccttgctgcc agctgcgagc cgg                                          23

SEQ ID NO: 31          moltype = DNA  length = 23
FEATURE                Location/Qualifiers
misc_feature           1..23
                       note = Guide RNA Recognition Sequence Near SREBF1 Variation
source                 1..23
                       mol_type = other DNA
                       organism = synthetic construct
SEQUENCE: 31
agaccggggt gtccctagga agg                                          23

SEQ ID NO: 32          moltype = DNA  length = 23
FEATURE                Location/Qualifiers
misc_feature           1..23
                       note = Guide RNA Recognition Sequence Near SREBF1 Variation
source                 1..23
                       mol_type = other DNA
                       organism = synthetic construct
SEQUENCE: 32
gttccttcct agggacaccc cgg                                          23

SEQ ID NO: 33          moltype = DNA  length = 23
FEATURE                Location/Qualifiers
misc_feature           1..23
                       note = Guide RNA Recognition Sequence Near SREBF1 Variation
source                 1..23
                       mol_type = other DNA
                       organism = synthetic construct
SEQUENCE: 33
gcacagaccg gggtgtccct agg                                          23

SEQ ID NO: 34          moltype = DNA  length = 23
FEATURE                Location/Qualifiers
misc_feature           1..23
                       note = Guide RNA Recognition Sequence Near SREBF1 Variation
source                 1..23
                       mol_type = other DNA
                       organism = synthetic construct
SEQUENCE: 34
gagctcaagg atctggtggt ggg                                          23

SEQ ID NO: 35          moltype = DNA  length = 23
FEATURE                Location/Qualifiers
misc_feature           1..23
                       note = Guide RNA Recognition Sequence Near SREBF1 Variation
source                 1..23
                       mol_type = other DNA
                       organism = synthetic construct
SEQUENCE: 35
tccctaggaa ggaacagatc agg                                          23

SEQ ID NO: 36          moltype = DNA  length = 23
FEATURE                Location/Qualifiers
misc_feature           1..23
                       note = Guide RNA Recognition Sequence Near SREBF1 Variation
source                 1..23
                       mol_type = other DNA
                       organism = synthetic construct
SEQUENCE: 36
tgagctcaag gatctggtgg tgg                                          23

SEQ ID NO: 37          moltype = DNA  length = 23
FEATURE                Location/Qualifiers
misc_feature           1..23
                       note = Guide RNA Recognition Sequence Near SREBF1 Variation
source                 1..23
                       mol_type = other DNA
```

-continued

```
                     organism = synthetic construct
SEQUENCE: 37
accccggtct gtgcccctgc agg                                       23

SEQ ID NO: 38        moltype = DNA  length = 23
FEATURE              Location/Qualifiers
misc_feature         1..23
                     note = Guide RNA Recognition Sequence Near SREBF1 Variation
source               1..23
                     mol_type = other DNA
                     organism = synthetic construct
SEQUENCE: 38
gcctgcaggg gcacagaccg ggg                                       23

SEQ ID NO: 39        moltype = DNA  length = 23
FEATURE              Location/Qualifiers
misc_feature         1..23
                     note = Guide RNA Recognition Sequence Near SREBF1 Variation
source               1..23
                     mol_type = other DNA
                     organism = synthetic construct
SEQUENCE: 39
cattgagctc aaggatctgg tgg                                       23

SEQ ID NO: 40        moltype = DNA  length = 23
FEATURE              Location/Qualifiers
misc_feature         1..23
                     note = Guide RNA Recognition Sequence Near SREBF1 Variation
source               1..23
                     mol_type = other DNA
                     organism = synthetic construct
SEQUENCE: 40
ccggctcgca gctggcagca agg                                       23

SEQ ID NO: 41        moltype = DNA  length = 23
FEATURE              Location/Qualifiers
misc_feature         1..23
                     note = Guide RNA Recognition Sequence Near SREBF1 Variation
source               1..23
                     mol_type = other DNA
                     organism = synthetic construct
SEQUENCE: 41
ggagcggtag cacttctcaa tgg                                       23
```

TREATMENT OF INCREASED LIPID LEVELS WITH STEROL REGULATORY ELEMENT BINDING TRANSCRIPTION FACTOR 1 (SREBF1) INHIBITORS

REFERENCE TO SEQUENCE LISTING

This application includes a Sequence Listing submitted electronically as a text file named 18923802001SEQ, created on Mar. 7, 2020, with a size of 191 kilobytes. The Sequence Listing is incorporated herein by reference.

FIELD

The present disclosure relates generally to the treatment of subjects having increased lipid levels with Sterol Regulatory Element Binding Transcription Factor 1 (SREBF1) inhibitors, methods of identifying subjects having an increased risk of developing increased lipid levels, methods of detecting SREBF1 variant nucleic acid molecules and variant polypeptides, and SREBF1 variant nucleic acid molecules and SREBF1 variant polypeptides.

BACKGROUND

Lipid metabolism disorders are a well-known complication of obesity. Lipid metabolism disorders are often characterised by hyperinsulinaemia, elevated apolipoprotein B levels, high triglycerides concentration, high low-density lipoproteins (LDL) cholesterol concentration, and low high-density lipoproteins (HDL) cholesterol concentration.

Sterol Regulatory Element Binding Proteins (SREBPs) are transcriptional factors that control lipogenesis and lipid uptake. There are two SREBP genes in mammals, SREBP-1 and SREBP-2. The SREBP-1 gene transcribes two isoforms SREBP-la and SREBP-1c encoded from different promoters, which regulate genes that control fatty acid synthesis. SREBP-2 regulates genes involved in cholesterol synthesis. The roles of SREBP-1 and SREBP-2, however, significantly overlap in the regulation of lipid metabolism. In normal tissues, SREBPs levels and activity are tightly controlled by endogenous sterol levels via negative feedback regulation. SREBPs are located in the endoplasmic reticulum (ER) membrane in association with SREBPs cleavage-activating protein (SCAP) in which they are retained by Insulin-induced gene (Insig) when cellular sterol levels are sufficient. Once sterol levels decrease, SCAP protein dissociates with Insig protein and escorts SREBPs to the Golgi, in which they are sequentially cleaved by site-1 and site-2 proteases (S1P and S2P) thereby releasing the N-terminus, which then enters into the nucleus to transcribe lipogenesis genes and low-density lipoprotein receptor (LDLR).

SUMMARY

The present disclosure also provides methods of treating a subject having increased total cholesterol, the method comprising administering an SREBF1 inhibitor to the subject.

The present disclosure also provides methods of treating a subject having increased low density lipoprotein (LDL), the method comprising administering an SREBF1 inhibitor to the subject.

The present disclosure also provides methods of treating a subject with a therapeutic agent that treats or inhibits an increased lipid level, wherein the subject is suffering from an increased lipid level, the method comprising the steps of determining whether the subject has an SREBF1 variant nucleic acid molecule encoding a human SREBF1 polypeptide by: obtaining or having obtained a biological sample from the subject; and performing or having performed a genotyping assay on the biological sample to determine if the subject has a genotype comprising the SREBF1 variant nucleic acid molecule; and when the subject is SREBF1 reference, then administering or continuing to administer to the subject the therapeutic agent that treats or inhibits the increased lipid level in a standard dosage amount, and administering to the subject an SREBF1 inhibitor; and when the subject is heterozygous for the SREBF1 variant, then administering or continuing to administer to the subject the therapeutic agent that treats or inhibits the increased lipid level in an amount that is the same as or lower than a standard dosage amount, and administering to the subject an SREBF1 inhibitor; wherein the presence of a genotype having the SREBF1 variant nucleic acid molecule encoding the human SREBF1 polypeptide indicates the subject has a reduced risk of developing the increased lipid level; wherein the increased lipid level is increased serum lipid level, increased total cholesterol, or increased LDL; and wherein the SREBF1 variant nucleic acid molecule is: i) a genomic nucleic acid molecule having a nucleotide sequence comprising a thymine at a position corresponding to position 17,922 according to SEQ ID NO:2, or the complement thereof, ii) an mRNA molecule having a nucleotide sequence comprising a uracil at a position corresponding to position 1,185 according to SEQ ID NO:6, or the complement thereof, iii) an mRNA molecule having a nucleotide sequence comprising a uracil at a position corresponding to position 1,260 according to SEQ ID NO:7, or the complement thereof, iv) an mRNA molecule having a nucleotide sequence comprising a uracil at a position corresponding to position 1,056 according to SEQ ID NO:8, or the complement thereof, v) a cDNA molecule produced from an mRNA molecule in the sample, wherein the cDNA molecule has a nucleotide sequence comprising a thymine at a position corresponding to position 1,185 according to SEQ ID NO:12, or the complement thereof, vi) a cDNA molecule produced from an mRNA molecule in the sample, wherein the cDNA molecule has a nucleotide sequence comprising a thymine at a position corresponding to position 1,260 according to SEQ ID NO:13, or the complement thereof, and/or vii) a cDNA molecule produced from an mRNA molecule in the sample, wherein the cDNA molecule has a nucleotide sequence comprising a thymine at a position corresponding to position 1,056 according to SEQ ID NO:14, or the complement thereof.

The present disclosure also provides methods of identifying a human subject having an increased risk for developing an increased lipid level, wherein the method comprises determining or having determined the presence or absence of an SREBF1 variant nucleic acid molecule encoding a human SREBF1 polypeptide in a biological sample obtained from the subject; wherein: when the human subject is SREBF1 reference, then the human subject has an increased risk for developing the increased lipid level; and when the human subject is heterozygous for the SREBF1 variant nucleic acid molecule or homozygous for the variant nucleic acid molecule, then the human subject has a decreased risk for developing the increased lipid level; wherein the SREBF1 variant nucleic acid molecule is: i) a genomic nucleic acid molecule having a nucleotide sequence comprising a thymine at a position corresponding to position 17,922 according to SEQ ID NO:2, or the complement thereof, ii) an mRNA molecule having a nucleotide sequence comprising a uracil at a position corresponding to position 1,185 according to SEQ ID NO:6, or the complement thereof, iii) an mRNA molecule having a nucleotide sequence comprising a uracil at a position corresponding to position 1,260 according to SEQ ID NO:7, or the complement thereof, iv) an mRNA molecule having a nucleotide sequence comprising a uracil at a position corresponding to position 1,056 according to SEQ ID NO:8, or the complement thereof, v) a cDNA molecule produced from an mRNA molecule in the sample, wherein the cDNA molecule has a nucleotide sequence comprising a thymine at a position corresponding to position 1,185 according to SEQ ID NO:12, or the complement thereof, vi) a cDNA molecule produced from an mRNA molecule in the sample, wherein the cDNA molecule has a nucleotide sequence comprising a thymine at a position corresponding to position 1,260 according to SEQ ID NO:13, or the complement thereof, and/or vii) a cDNA molecule produced from an mRNA molecule in the sample, wherein the cDNA molecule has a nucleotide sequence comprising a thymine at a position corresponding to position 1,056 according to SEQ ID NO:14, or the complement thereof.

The present disclosure also provides methods of detecting a human SREBF1 variant nucleic acid molecule in a human subject comprising assaying a sample obtained from the human subject to determine whether a nucleic acid molecule in the sample comprises a nucleotide sequence comprising: i) a thymine at a position corresponding to position 17,922 according to SEQ ID NO:2, or the complement thereof; ii) a uracil at a position corresponding to position 1,185 according to SEQ ID NO:6, or the complement thereof; iii) a uracil at a position corresponding to position 1,260 according to SEQ ID NO:7, or the complement thereof; iv) a uracil at a position corresponding to position 1,056 according to SEQ ID NO:8, or the complement thereof; v) a thymine at a position corresponding to position 1,185 according to SEQ ID NO:12, or the complement thereof; vi) a thymine at a position corresponding to position 1,260 according to SEQ ID NO:13, or the complement thereof; and/or vii) a thymine at a position corresponding to position 1,056 according to SEQ ID NO:14, or the complement thereof.

The present disclosure also provides isolated alteration-specific probes or alteration-specific primers comprising at least about 15 nucleotides, wherein the alteration-specific probe or alteration-specific primer comprises a nucleotide sequence which is complementary to a portion of a nucleotide sequence encoding a human SREBF1 polypeptide, wherein the portion comprises a position corresponding to: i) position 17,922 according to SEQ ID NO:2, or the complement thereof; ii) position 1,185 according to SEQ ID NO:6, or the complement thereof; iii) position 1,260 according to SEQ ID NO:7, or the complement thereof; iv) position 1,056 according to SEQ ID NO:8, or the complement thereof; v) position 1,185 according to SEQ ID NO:12, or the complement thereof; vi) position 1,260 according to SEQ ID NO:13, or the complement thereof; or vii) position 1,056 according to SEQ ID NO:14, or the complement thereof.

The present disclosure also provides isolated nucleic acid molecules comprising a nucleotide sequence encoding a human SREBF1 polypeptide, wherein the polypeptide comprises: i) a cysteine at a position corresponding to position 334 according to SEQ ID NO:18, or the complement thereof; ii) a cysteine at a position corresponding to position 364 according to SEQ ID NO:19, or the complement thereof; or iii) a cysteine at a position corresponding to position 310 according to SEQ ID NO:20, or the complement thereof.

The present disclosure also provides isolated nucleic acid molecules comprising a nucleotide sequence encoding a human SREBF1 polypeptide, wherein the nucleotide sequence comprises a thymine at a position corresponding to position 17,922 according to SEQ ID NO:2, or the complement thereof.

The present disclosure also provides isolated mRNA molecules comprising a nucleotide sequence encoding a human SREBF1 polypeptide, wherein the nucleotide sequence comprises: i) a uracil at a position corresponding to position 1,185 according to SEQ ID NO:6, or the complement thereof; ii) a uracil at a position corresponding to position 1,260 according to SEQ ID NO:7, or the complement thereof; or iii) a uracil at a position corresponding to position 1,056 according to SEQ ID NO:8, or the complement thereof.

The present disclosure also provides cDNA molecules comprising a nucleotide sequence encoding a human SREBF1 polypeptide, wherein the nucleotide sequence comprises: i) a thymine at a position corresponding to position 1,185 according to SEQ ID NO:12, or the complement thereof; ii) a thymine at a position corresponding to position 1,260 according to SEQ ID NO:13, or the complement thereof; or iii) a thymine at a position corresponding to position 1,056 according to SEQ ID NO:14, or the complement thereof.

The present disclosure also provides isolated SREBF1 polypeptides having: i) an amino acid sequence at least about 90% identical to SEQ ID NO:18, wherein the polypeptide comprises a cysteine at a position corresponding to position 334 according to SEQ ID NO:18; ii) an amino acid sequence at least about 90% identical to SEQ ID NO:19, wherein the polypeptide comprises a cysteine at a position corresponding to position 364 according to SEQ ID NO:19; or iii) an amino acid sequence at least about 90% identical to SEQ ID NO:20, wherein the polypeptide comprises a cysteine at a position corresponding to position 310 according to SEQ ID NO:20.

The present disclosure also provides molecular complexes comprising an alteration-specific primer or an alteration-specific probe hybridized to: i) a genomic nucleic acid molecule comprising a nucleotide sequence encoding a human SREBF1 polypeptide, wherein the alteration-specific primer or the alteration-specific probe is hybridized to a thymine at a position corresponding to position 17,922 according to SEQ ID NO:2, or the complement thereof; ii) an mRNA molecule comprising a nucleotide sequence encoding a human SREBF1 polypeptide, wherein the alteration-specific primer or the alteration-specific probe is hybridized to: a uracil at a position corresponding to position 1,185 according to SEQ ID NO:6, or the complement thereof; a uracil at a position corresponding to position 1,260 according to SEQ ID NO:7, or the complement thereof; or a uracil at a position corresponding to position 1,056 according to SEQ ID NO:8, or the complement thereof; or iii) a cDNA molecule comprising a nucleotide sequence encoding a human SREBF1 polypeptide, wherein the alteration-specific primer or the alteration-specific probe is hybridized to: a thymine at a position corresponding to position 1,185 according to SEQ ID NO:12, or the complement thereof; a thymine at a position corresponding to position 1,260 according to SEQ ID NO:13, or the complement thereof; or a thymine at a position corresponding to position 1,056 according to SEQ ID NO:14, or the complement thereof.

BRIEF DESCRIPTION OF THE DRAWINGS

The accompanying figures, which are incorporated in and constitute a part of this specification, illustrate several aspects and together with the description serve to explain the principles of the present disclosure.

DESCRIPTION

Figure 1:
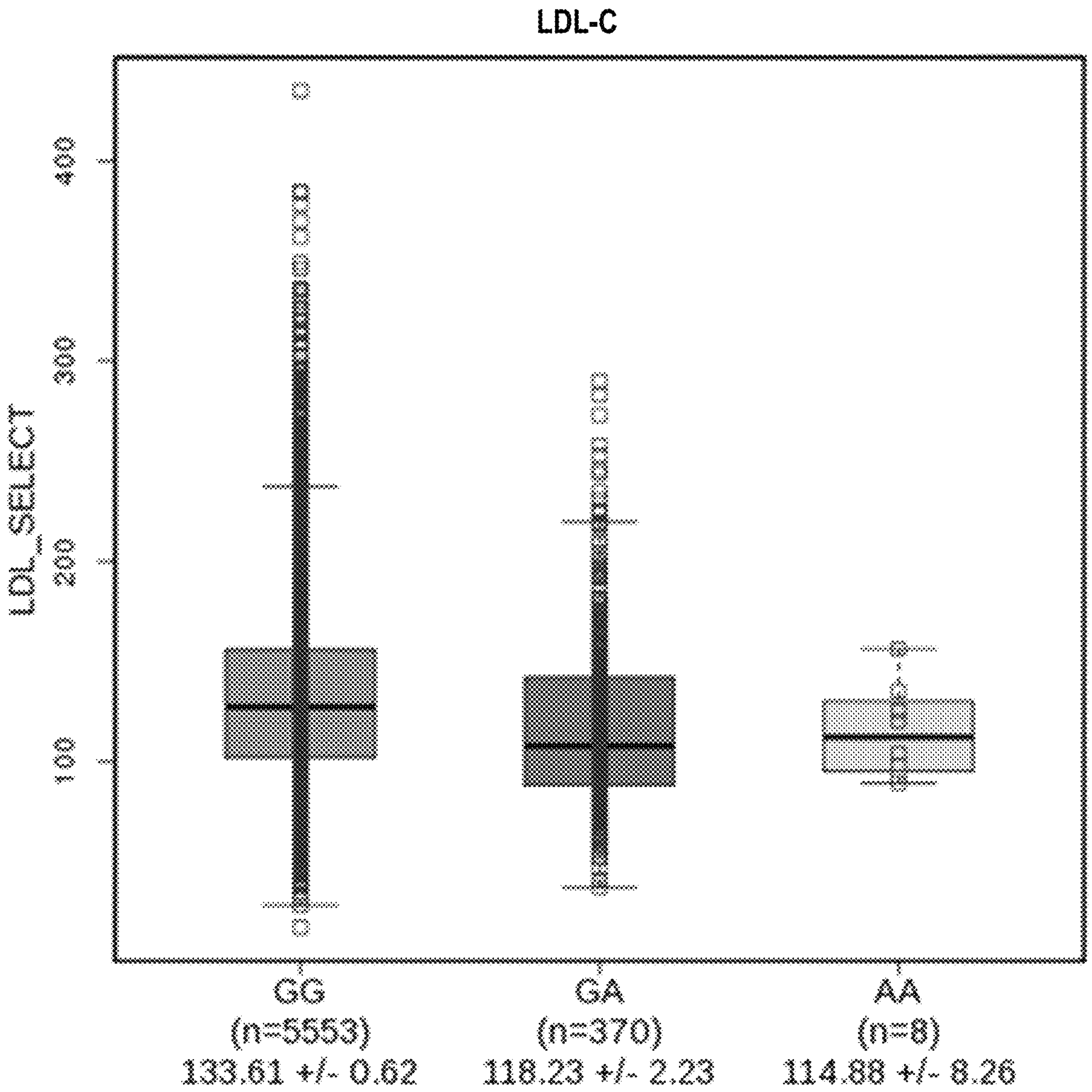
FIG. 1 (Panels A-C) shows an association of an SREBF1 missense variant with decreased low-density lipoprotein-cholesterol (LDL-C) (Panel A), decreased non-HDL cholesterol (Panel B), and decreased total cholesterol (Panel C).
Figure 1:
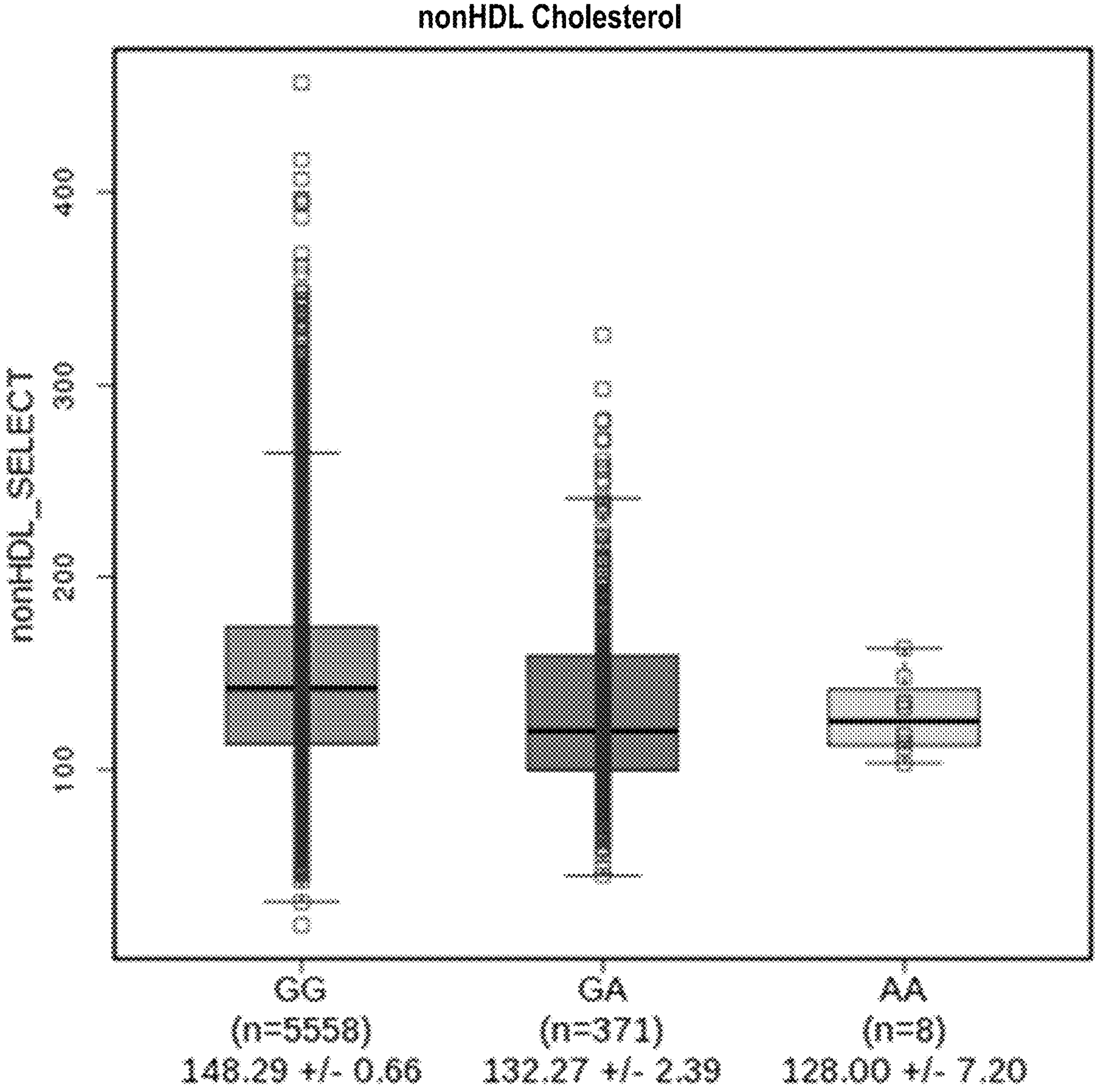
Figure 1:
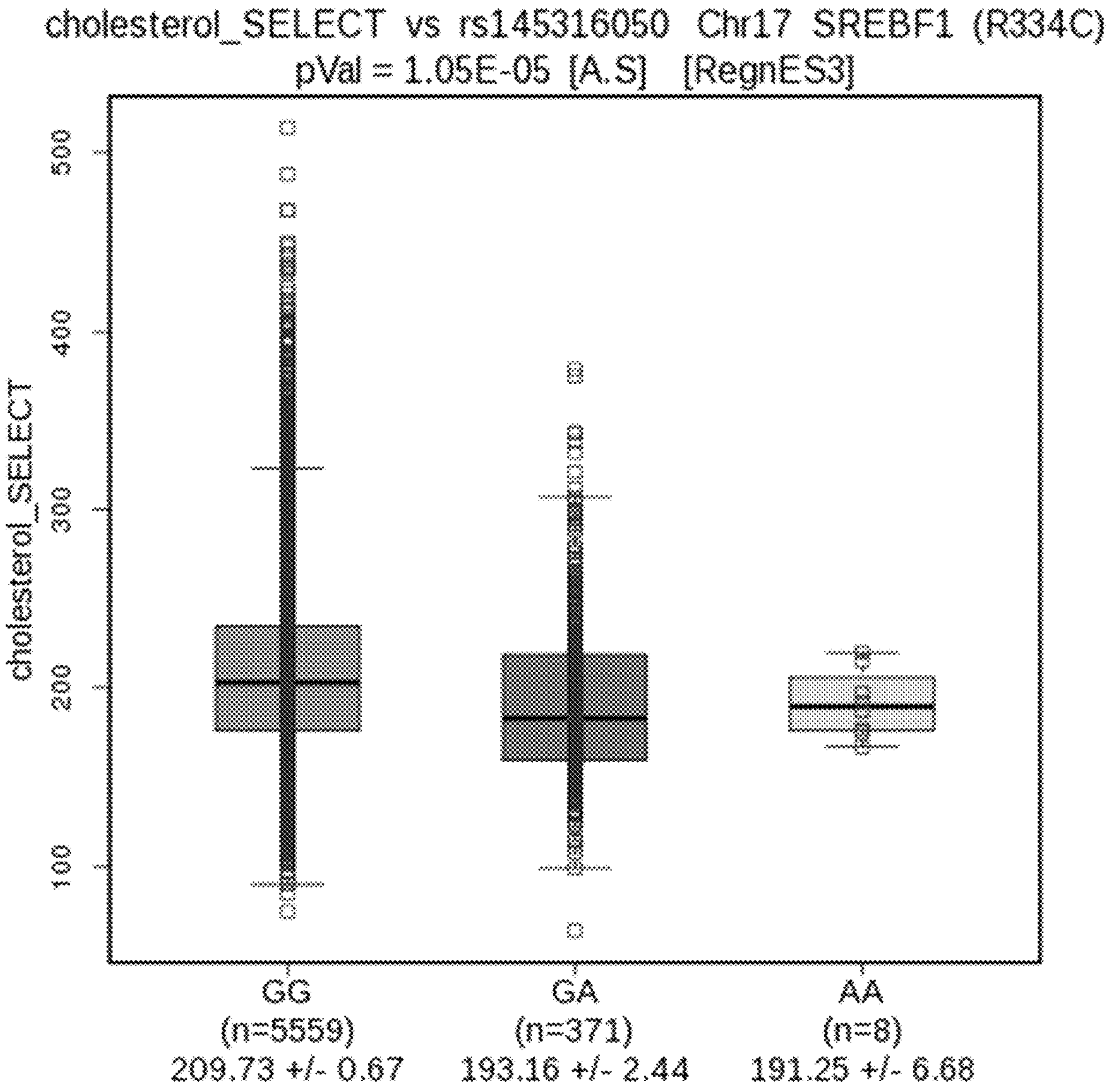

Various terms relating to aspects of the present disclosure are used throughout the specification and claims. Such terms are to be given their ordinary meaning in the art, unless otherwise indicated. Other specifically defined terms are to be construed in a manner consistent with the definitions provided herein.

Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is in no way intended that an order be inferred, in any respect. This holds for any possible non-expressed basis for interpretation, including matters of logic with respect to arrangement of steps or operational flow, plain meaning derived from grammatical organization or punctuation, or the number or type of aspects described in the specification.

As used herein, the singular forms "a," "an" and "the" include plural referents unless the context clearly dictates otherwise.

As used herein, the term "subject" includes any animal, including mammals. Mammals include, but are not limited to, farm animals (such as, for example, horse, cow, pig), companion animals (such as, for example, dog, cat), laboratory animals (such as, for example, mouse, rat, rabbits), and non-human primates. In some embodiments, the subject is a human.

As used herein, a "nucleic acid," a "nucleic acid molecule," a "nucleic acid sequence," a "polynucleotide," or an "oligonucleotide" can comprise a polymeric form of nucleotides of any length, can comprise DNA and/or RNA, and can be single-stranded, double-stranded, or multiple stranded. One strand of a nucleic acid also refers to its complement.

As used herein, the term "comprising" may be replaced with "consisting" or "consisting essentially of" in particular embodiments as desired.

An "isolated" nucleic acid molecule is a polynucleotide that is in a condition other than its native environment, such as apart from blood and animal tissue. In a preferred form, the isolated nucleic acid molecule is substantially free of other polynucleotides, particularly other polypeptides of animal origin. It is preferred to provide the nucleic acid molecule in a highly purified form, i.e., greater than 95% pure, more preferably greater than 99% pure. When used in this context, the term "isolated" does not exclude the presence of the same nucleic acid molecule in alternative physical forms, such as dimers or alternatively phosphorylated or derivatized forms.

It has been observed in accordance with the present disclosure that particular variations in SREBF1 associate with decreased low density lipoprotein (LDL) and decreased total cholesterol. It is believed that no variants of the SREBF1 gene or protein have any known association with decreased low density lipoprotein (LDL) and decreased total cholesterol.

A rare variant in the SREBF1 gene segregating with decreased LDL and decreased total cholesterol has been identified in accordance with the present disclosure. For example, a genetic alteration that changes the cytosine nucleotide of position 17,922 in the human wild type SREBF1 gene (SEQ ID NO:1) to thymine has been observed to indicate that the human having such an alteration may have decreased LDL and decreased total cholesterol. Altogether, the genetic analyses described herein surprisingly indicate that the SREBF1 gene and, in particular, a variant in the SREBF1 gene, associates with decreased LDL and decreased total cholesterol. Therefore, human subjects that are SREBF1 reference that have an increased risk of developing an increased lipid level may be treated such that the increased lipid level is inhibited, the symptoms thereof are reduced, and/or development of symptoms is repressed. Accordingly, the disclosure provides methods of leveraging the identification of such variants in subjects to identify or stratify risk in such subjects of developing increased lipid levels, such that subjects at risk or subjects with active disease may be treated accordingly. Additionally, the present disclosure provides isolated SREBF1 variant genomic nucleic acid molecules, variant mRNA molecule, and variant cDNA molecules. Accordingly, provided herein are SREBF1 variant nucleic acid molecules discovered to be associated with decreased LDL and decreased total cholesterol.

For purposes of the present disclosure, any particular human can be categorized as having one of three SREBF1 genotypes: i) SREBF1 reference; ii) heterozygous for an SREBF1 variant (such as a predicted loss-of-function variant), and iii) homozygous for an SREBF1 variant (such as a predicted loss-of-function variant). A human in the SREBF1 reference category does not have a copy of an SREBF1 variant nucleic acid molecule (such as a predicted loss-of-function variant nucleic acid molecule). A human who is heterozygous for an SREBF1 variant nucleic acid molecule (such as a predicted loss-of-function variant nucleic acid molecule) has a single copy of an SREBF1 variant nucleic acid molecule (such as a predicted loss-of-function variant nucleic acid molecule). A human who is homozygous for an SREBF1 variant nucleic acid molecule (such as a predicted loss-of-function variant nucleic acid molecule) has two copies of an SREBF1 variant nucleic acid molecule (such as a predicted loss-of-function variant nucleic acid molecule). An SREBF1 predicted loss-of-function variant nucleic acid molecule is any SREBF1 nucleic acid molecule (such as, a genomic nucleic acid molecule, an mRNA molecule, or a cDNA molecule) encoding an SREBF1 polypeptide having a partial loss-of-function, a complete loss-of-function, a predicted partial loss-of-function, or a predicted complete loss-of-function. A human who has an SREBF1 polypeptide having a partial loss-of-function (or predicted partial loss-of-function) is hypomorphic for SREBF1. The SREBF1 variant nucleic acid molecule can be any nucleic acid molecule encoding SREBF1 Arg334Cys, Arg364Cys, or Arg310Cys. It is believed that the SREBF1 variant nucleic acid molecules described herein encoding SREBF1 Arg334Cys, Arg364Cys, or Arg310Cys are SREBF1 predicted loss-of-function variant nucleic acid molecules. In some embodiments, the SREBF1 variant nucleic acid molecule encodes SREBF1 Arg334Cys. In some embodiments, the SREBF1 variant nucleic acid molecule encodes SREBF1 Arg364Cys. In some embodiments, the SREBF1 variant nucleic acid molecule encodes SREBF1 Arg310Cys.

For human subjects that are genotyped or determined to be SREBF1 reference, such human subjects have an increased risk of developing an increased lipid level, such as increased serum lipid level, increased total cholesterol, and/or increased LDL. For human subjects that are genotyped or determined to be either SREBF1 reference or heterozygous for an SREBF1 variant nucleic acid molecule (such as a predicted loss-of-function variant), such human subjects can be treated with an SREBF1 inhibitor.

The present disclosure provides methods of treating a subject having increased serum lipid level, the methods comprising administering an SREBF1 inhibitor to the subject.

The present disclosure also provides methods of treating a subject having increased total cholesterol, the methods comprising administering an SREBF1 inhibitor to the subject.

The present disclosure also provides methods of treating a subject having increased LDL, the methods comprising administering an SREBF1 inhibitor to the subject.

In any of the embodiments described herein, the increased lipid level is increased serum lipid level, increased total cholesterol, or increased LDL. In some embodiments, the increased lipid level is increased serum lipid level. In some embodiments, the increased lipid level is increased total cholesterol. In some embodiments, the increased lipid level is increased serum cholesterol. In some embodiments, the increased lipid level is increased LDL.

In some embodiments, the SREBF1 inhibitor comprises an antisense molecule. Examples of antisense molecules include, but are not limited to, antisense nucleic acid molecules, small interfering RNAs (siRNAs), and short hairpin RNAs (shRNAs). Such antisense molecules can be designed to target any region of an SREBF1 mRNA. In some embodiments, the antisense RNA, siRNA, or shRNA hybridizes to a sequence within an SREBF1 genomic nucleic acid molecule or mRNA molecule and decreases expression of the SREBF1 polypeptide in a cell in the subject. In some embodiments, the SREBF1 inhibitor comprises an antisense RNA that hybridizes to an SREBF1 genomic nucleic acid molecule or mRNA molecule and decreases expression of the SREBF1 polypeptide in a cell in the subject. In some embodiments, the SREBF1 inhibitor comprises an siRNA that hybridizes to an SREBF1 genomic nucleic acid molecule or mRNA molecule and decreases expression of the SREBF1 polypeptide in a cell in the subject. In some embodiments, the SREBF1 inhibitor comprises an shRNA that hybridizes to an SREBF1 genomic nucleic acid molecule or mRNA molecule and decreases expression of the SREBF1 polypeptide in a cell in the subject.

In some embodiments, the SREBF1 inhibitor comprises a nuclease agent that induces one or more nicks or double-strand breaks at a recognition sequence(s) or a DNA-binding protein that binds to a recognition sequence within an SREBF1 genomic nucleic acid molecule. The recognition sequence can be located within a coding region of an SREBF1 gene, or within regulatory regions that influence the expression of the gene. A recognition sequence of the DNA-binding protein or nuclease agent can be located in an intron, an exon, a promoter, an enhancer, a regulatory region, or any non-protein coding region. The recognition sequence can include or be proximate to the start codon of an SREBF1 gene. For example, the recognition sequence can be located from about 10, 20, 30, 40, 50, 100, 200, 300, 400, 500, or 1,000 nucleotides of the start codon. As another example, two or more nuclease agents can be used, each targeting a nuclease recognition sequence including or proximate to the start codon. As another example, two nuclease agents can be used, one targeting a nuclease recognition sequence including or proximate to the start codon, and one targeting a nuclease recognition sequence including or proximate to the stop codon, wherein cleavage by the nuclease agents can result in deletion of the coding region between the two nuclease recognition sequences. Any nuclease agent that induces a nick or double-strand break into a desired recognition sequence can be used in the methods and compositions disclosed herein. Any DNA-binding protein that binds to a desired recognition sequence can be used in the methods and compositions disclosed herein.

Suitable nuclease agents and DNA-binding proteins for use herein include, but are not limited to, zinc finger protein or zinc finger nuclease (ZFN) pair, Transcription Activator-Like Effector (TALE) protein or Transcription Activator-Like Effector Nuclease (TALEN), or Clustered Regularly Interspersed Short Palindromic Repeats (CRISPR)/CRISPR-associated (Cas) systems. The length of the recognition sequence can vary, and includes, for example, recognition sequences that are about 30-36 bp for a zinc finger protein or ZFN pair (i.e., about 15-18 bp for each ZFN), about 36 bp for a TALE protein or TALEN, and about 20 bp for a CRISPR/Cas guide RNA.

In some embodiments, CRISPR/Cas systems can be used to modify an SREBF1 genomic nucleic acid molecule within a cell. The methods and compositions disclosed herein can employ CRISPR-Cas systems by utilizing CRISPR complexes (comprising a guide RNA (gRNA) complexed with a Cas protein) for site-directed cleavage of SREBF1 nucleic acid molecules.

Cas proteins generally comprise at least one RNA recognition or binding domain that can interact with gRNAs. Cas proteins can also comprise nuclease domains (such as, for example, DNase or RNase domains), DNA binding domains, helicase domains, protein-protein interaction domains, dimerization domains, and other domains. Suitable Cas proteins include, for example, a wild type Cas9 protein and a wild type Cpf1 protein (such as, for example, FnCpf1). A Cas protein can have full cleavage activity to create a double-strand break in an SREBF1 genomic nucleic acid molecule or it can be a nickase that creates a single-strand break in an SREBF1 genomic nucleic acid molecule. Additional examples of Cas proteins include, but are not limited to, Cas1, Cas1B, Cas2, Cas3, Cas4, Cas5, Cas5e (CasD), Cas6, Cas6e, Cas6f, Cas7, Cas8a1, Cas8a2, Cas8b, Cas8c, Cas9 (Csn1 or Csx12), Cas10, Casl0d, CasF, CasG, CasH, Csy1, Csy2, Csy3, Cse1 (CasA), Cse2 (CasB), Cse3 (CasE), Cse4 (CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, and Cu1966, and homologs or modified versions thereof. Cas proteins can also be operably linked to heterologous polypeptides as fusion proteins. For example, a Cas protein can be fused to a cleavage domain, an epigenetic modification domain, a transcriptional activation domain, or a transcriptional repressor domain. Cas proteins can be provided in any form. For example, a Cas protein can be provided in the form of a protein, such as a Cas protein complexed with a gRNA. Alternately, a Cas protein can be provided in the form of a nucleic acid molecule encoding the Cas protein, such as an RNA or DNA.

In some embodiments, targeted genetic modifications of SREBF1 genomic nucleic acid molecules can be generated by contacting a cell with a Cas protein and one or more gRNAs that hybridize to one or more gRNA recognition sequences that are located within a target genomic locus in the SREBF1 genomic nucleic acid molecule. For example, a gRNA recognition sequence can be within a region of SEQ ID NO:1. As another example, the gRNA recognition sequence can also include or be proximate to a position corresponding to position 17,922 according to SEQ ID NO:1. For example, the gRNA recognition sequence can be located from about 1000, 500, 400, 300, 200, 100, 50, 45, 40, 35, 30, 25, 20, 15, 10, or 5 nucleotides of a position corresponding to position 17,922 according to SEQ ID NO:1. As yet another example, a gRNA recognition sequence can include or be proximate to the start codon of an SREBF1 genomic nucleic acid molecule or the stop codon of an SREBF1 genomic nucleic acid molecule. For example, the gRNA recognition sequence can be located from about 10, 20, 30, 40, 50, 100, 200, 300, 400, 500, or 1,000 nucleotides of the start codon or the stop codon.

The gRNA recognition sequences that are located within a target genomic locus in an SREBF1 genomic nucleic acid molecule are located near a Protospacer Adjacent Motif (PAM) sequence, which is a 2-6 base pair DNA sequence immediately following the DNA sequence targeted by the Cas9 nuclease. The canonical PAM is the sequence 5'-NGG-3' where “N” is any nucleobase followed by two guanine (“G”) nucleobases. gRNAs can transport Cas9 to anywhere in the genome for gene editing, but no editing can occur at any site other than one at which Cas9 recognizes PAM. In addition, 5'-NGA-3' can be a highly efficient non-canonical PAM for human cells. Generally, the PAM is about 2-6 nucleotides downstream of the DNA sequence targeted by the gRNA. The PAM can flank the gRNA recognition sequence. In some embodiments, the gRNA recognition sequence can be flanked on the 3' end by the PAM. In some embodiments, the gRNA recognition sequence can be flanked on the 5' end by the PAM. For example, the cleavage site of Cas proteins can be about 1 to about 10, about 2 to about 5 base pairs, or three base pairs upstream or downstream of the PAM sequence. In some embodiments (such as when Cas9 from *S. pyogenes* or a closely related Cas9 is used), the PAM sequence of the non-complementary strand can be 5'-NGG-3', where N is any DNA nucleotide and is immediately 3' of the gRNA recognition sequence of the non-complementary strand of the target DNA. As such, the PAM sequence of the complementary strand would be 5'-CCN-3', where N is any DNA nucleotide and is immediately 5' of the gRNA recognition sequence of the complementary strand of the target DNA.

A gRNA is an RNA molecule that binds to a Cas protein and targets the Cas protein to a specific location within an SREBF1 genomic nucleic acid molecule. One exemplary gRNA is a gRNA effective to direct a Cas enzyme to bind to or cleave an SREBF1 genomic nucleic acid molecule, wherein the gRNA comprises a DNA-targeting segment that hybridizes to a gRNA recognition sequence within the SREBF1 genomic nucleic acid molecule that includes or is proximate to a position corresponding to position 17,922 according to SEQ ID NO:1. For example, a gRNA can be selected such that it hybridizes to a gRNA recognition sequence that is located from about 5, 10, 15, 20, 25, 30, 35, 40, 45, 50, 100, 200, 300, 400, 500, or 1,000 nucleotides of a position corresponding to position 17,922 according to SEQ ID NO:1. Other exemplary gRNAs comprise a DNA-targeting segment that hybridizes to a gRNA recognition sequence within an SREBF1 genomic nucleic acid molecule that is within a region of SEQ ID NO:1. Other exemplary gRNAs comprise a DNA-targeting segment that hybridizes to a gRNA recognition sequence within an SREBF1 genomic nucleic acid molecule that includes or is proximate to the start codon or the stop codon. For example, a gRNA can be selected such that it hybridizes to a gRNA recognition sequence that is located from about 5, 10, 15, 20, 25, 30, 35, 40, 45, 50, 100, 200, 300, 400, 500, or 1,000 nucleotides of the start codon or located from about 5, 10, 15, 20, 25, 30, 35, 40, 45, 50, 100, 200, 300, 400, 500, or 1,000 nucleotides of the start codon or stop codon. The design and synthesis of gRNAs are described in, for example, Mali et al., Science, 2013, 339, 823-826; Jinek et al., Science, 2012, 337, 816-821; Hwang et al., Nat. Biotechnol., 2013, 31, 227-229; Jiang et al., Nat. Biotechnol., 2013, 31, 233-239; and Cong et al., Science, 2013, 339, 819-823. Suitable gRNAs can comprise from about 17 to about 23 nucleotides, from about 18 to about 22 nucleotides, or from about 19 to about 21 nucleotides. In some embodiments, the gRNAs can comprise 20 nucleotides.

Examples of suitable gRNA recognition sequences located within the human wild type SREBF1 gene are set forth in SEQ ID NOS: 21-41.

Guide RNA Recognition Sequences Near SREBF1 Variation

| Strand | Sequence | SEQ ID NO: |
|---|---|---|
| - | TCTCCGCATCTACGACCAGTGGG | 21 |
| - | CCAGCTGCGAGCCGGTTGATAGG | 22 |
| - | TTCTCCGCATCTACGACCAGTGG | 23 |
| + | AGTCCCACTGGTCGTAGATGCGG | 24 |
| + | CCTATCAACCGGCTCGCAGCTGG | 25 |
| + | CGGAGAAGCTGCCTATCAACCGG | 26 |
| - | TGCGCTTCTCTCCACGGCTCTGG | 27 |
| - | GCGCTTCTCTCCACGGCTCTGGG | 28 |
| + | AATCATTGAGCTCAAGGATCTGG | 29 |
| - | CCTTGCTGCCAGCTGCGAGCCGG | 30 |
| + | AGACCGGGGTGTCCCTAGGAAGG | 31 |
| - | GTTCCTTCCTAGGGACACCCCGG | 32 |
| + | GCACAGACCGGGGTGTCCCTAGG | 33 |
| + | GAGCTCAAGGATCTGGTGGTGGG | 34 |
| + | TCCCTAGGAAGGAACAGATCAGG | 35 |
| + | TGAGCTCAAGGATCTGGTGGTGG | 36 |
| - | ACCCCGGTCTGTGCCCCTGCAGG | 37 |
| + | GCCTGCAGGGGCACAGACCGGGG | 38 |
| + | CATTGAGCTCAAGGATCTGGTGG | 39 |

-continued

| Guide RNA Recognition Sequences Near SREBF1 Variation | | |
|---|---|---|
| Strand | Sequence | SEQ ID NO: |
| + | CCGGCTCGCAGCTGGCAGCAAGG | 40 |
| - | GGAGCGGTAGCACTTCTCAATGG | 41 |

The Gas protein and the gRNA form a complex, and the Gas protein cleaves the target SREBF1 genomic nucleic acid molecule. The Gas protein can cleave the nucleic acid molecule at a site within or outside of the nucleic acid sequence present in the target SREBF1 genomic nucleic acid molecule to which the DNA-targeting segment of a gRNA will bind. For example, formation of a CRISPR complex (comprising a gRNA hybridized to a gRNA recognition sequence and complexed with a Cas protein) can result in cleavage of one or both strands in or near (such as, for example, within 1, 2, 3, 4, 5, 6, 7, 8, 9, 10, 20, 50, or more base pairs from) the nucleic acid sequence present in the SREBF1 genomic nucleic acid molecule to which a DNA-targeting segment of a gRNA will bind.

Such methods can result, for example, in an SREBF1 genomic nucleic acid molecule in which a region of SEQ ID NO:1 is disrupted, the start codon is disrupted, the stop codon is disrupted, or the coding sequence is deleted. Optionally, the cell can be further contacted with one or more additional gRNAs that hybridize to additional gRNA recognition sequences within the target genomic locus in the SREBF1 genomic nucleic acid molecule. By contacting the cell with one or more additional gRNAs (such as, for example, a second gRNA that hybridizes to a second gRNA recognition sequence), cleavage by the Cas protein can create two or more double-strand breaks or two or more single-strand breaks.

In some embodiments, the SREBF1 inhibitor comprises a small molecule. In some embodiments, the SREBF1 inhibitor is Fatostatin A or PF-429242.

In some embodiments, the methods further comprise detecting the presence or absence of an SREBF1 predicted loss-of-function variant nucleic acid molecule encoding a human SREBF1 polypeptide in a biological sample from the subject. In some embodiments, the methods further comprise detecting the presence or absence of an SREBF1 predicted loss-of-function variant polypeptide in a biological sample from the subject. As used throughout the present disclosure an “SREBF1 predicted loss-of-function variant nucleic acid molecule” is any SREBF1 nucleic acid molecule (such as, for example, genomic nucleic acid molecule, mRNA molecule, or cDNA molecule) encoding an SREBF1 polypeptide having a partial loss-of-function, a complete loss-of-function, a predicted partial loss-of-function, or a predicted complete loss-of-function. For example, the SREBF1 predicted loss-of-function variant nucleic acid molecule can be any nucleic acid molecule encoding SREBF1 Arg334Cys, Arg364Cys, or Arg310Cys. In some embodiments, the SREBF1 predicted loss-of-function variant nucleic acid molecule encodes SREBF1 Arg334Cys. In some embodiments, the SREBF1 predicted loss-of-function variant nucleic acid molecule encodes SREBF1 Arg364Cys. In some embodiments, the SREBF1 predicted loss-of-function variant nucleic acid molecule encodes SREBF1 Arg310Cys.

In some embodiments, the SREBF1 predicted loss-of-function variant nucleic acid molecule is: i) a genomic nucleic acid molecule having a nucleotide sequence comprising a thymine at a position corresponding to position 17,922 according to SEQ ID NO:2; ii) an mRNA molecule having a nucleotide sequence comprising a uracil at a position corresponding to position 1,185 according to SEQ ID NO:6; iii) an mRNA molecule having a nucleotide sequence comprising a uracil at a position corresponding to position 1,260 according to SEQ ID NO:7; iv) an mRNA molecule having a nucleotide sequence comprising a uracil at a position corresponding to position 1,056 according to SEQ ID NO:8; v) a cDNA molecule produced from an mRNA molecule, wherein the cDNA molecule has a nucleotide sequence comprising a thymine at a position corresponding to position 1,185 according to SEQ ID NO:12; vi) a cDNA molecule produced from an mRNA molecule, wherein the cDNA molecule has a nucleotide sequence comprising a thymine at a position corresponding to position 1,260 according to SEQ ID NO:13; or vii) a cDNA molecule produced from an mRNA molecule, wherein the cDNA molecule has a nucleotide sequence comprising a thymine at a position corresponding to position 1,056 according to SEQ ID NO:14.

In some embodiments, when the subject is SREBF reference, the subject is also administered a therapeutic agent that treats or inhibits an increased lipid level in a standard dosage amount. In some embodiments, when the subject is heterozygous for an SREBF predicted loss-of-function variant, the subject is also administered a therapeutic agent that treats or inhibits an increased lipid level in a dosage amount that is the same as or lower than the standard dosage amount.

The present disclosure also provides methods of treating a subject with a therapeutic agent that treats or inhibits an increased lipid level, wherein the subject is suffering from an increased lipid level, the method comprising the steps of: determining whether the subject has an SREBF1 predicted loss-of-function variant nucleic acid molecule encoding a human SREBF1 polypeptide by: obtaining or having obtained a biological sample from the subject; and performing or having performed a genotyping assay on the biological sample to determine if the subject has a genotype comprising the SREBF1 predicted loss-of-function variant nucleic acid molecule; and when the subject is SREBF1 reference, then: i) administering or continuing to administer to the subject the therapeutic agent that treats or inhibits the increased lipid level in a standard dosage amount, and administering to the subject an SREBF1 inhibitor; and when the subject is heterozygous for an SREBF1 predicted loss-of-function variant, then: i) administering or continuing to administer to the subject the therapeutic agent that treats or inhibits the increased lipid level in an amount that is the same as or lower than a standard dosage amount, and administering to the subject an SREBF1 inhibitor; wherein the presence of a genotype having the SREBF1 predicted loss-of-function variant nucleic acid molecule encoding the human SREBF1 polypeptide indicates the subject has a reduced risk of developing the increased lipid level. In some embodiments, the subject is SREBF1 reference. In some embodiments, the subject is heterozygous for an SREBF1 predicted loss-of-function variant.

The SREBF1 predicted loss-of-function variant nucleic acid molecule can be any SREBF1 nucleic acid molecule (such as, for example, genomic nucleic acid molecule, mRNA molecule, or cDNA molecule) encoding an SREBF1 polypeptide having a partial loss-of-function, a complete loss-of-function, a predicted partial loss-of-function, or a predicted complete loss-of-function. For example, the SREBF1 predicted loss-of-function variant nucleic acid molecule can be any nucleic acid molecule encoding SREBF1 Arg334Cys, Arg364Cys, or Arg310Cys.

In some embodiments, the SREBF1 predicted loss-of-function variant nucleic acid molecule is: i) a genomic nucleic acid molecule having a nucleotide sequence comprising a thymine at a position corresponding to position 17,922 according to SEQ ID NO:2; ii) an mRNA molecule having a nucleotide sequence comprising a uracil at a position corresponding to position 1,185 according to SEQ ID NO:6; iii) an mRNA molecule having a nucleotide sequence comprising a uracil at a position corresponding to position 1,260 according to SEQ ID NO:7; iv) an mRNA molecule having a nucleotide sequence comprising a uracil at a position corresponding to position 1,056 according to SEQ ID NO:8; v) a cDNA molecule produced from an mRNA molecule, wherein the cDNA molecule has a nucleotide sequence comprising a thymine at a position corresponding to position 1,185 according to SEQ ID NO:12; vi) a cDNA molecule produced from an mRNA molecule, wherein the cDNA molecule has a nucleotide sequence comprising a thymine at a position corresponding to position 1,260 according to SEQ ID NO:13; and/or vii) a cDNA molecule produced from an mRNA molecule, wherein the cDNA molecule has a nucleotide sequence comprising a thymine at a position corresponding to position 1,056 according to SEQ ID NO:14.

Detecting the presence or absence of an SREBF1 predicted loss-of-function variant nucleic acid molecule (such as, for example, a nucleic acid molecule encoding SREBF1 Arg334Cys, Arg364Cys, or Arg310Cys) in a biological sample from a subject and/or determining whether a subject has an SREBF1 predicted loss-of-function variant nucleic acid molecule (such as, for example, a nucleic acid molecule encoding SREBF1 Arg334Cys, Arg364Cys, or Arg310Cys) can be carried out by any of the methods described herein. In some embodiments, these methods can be carried out in vitro. In some embodiments, these methods can be carried out in situ. In some embodiments, these methods can be carried out in vivo.

In some embodiments, the detection step, detecting step, or genotyping assay comprises sequencing at least a portion of the nucleotide sequence of the SREBF1 genomic nucleic acid molecule, the SREBF1 mRNA molecule, or the SREBF1 cDNA molecule in the biological sample, wherein the sequenced portion comprises variation(s) that cause a loss-of-function or are predicted to cause a loss-of-function. For example, in some embodiments, the detection step, detecting step, or genotyping assay comprises sequencing at least a portion of: i) the nucleotide sequence of the genomic nucleic acid molecule encoding the SREBF1 polypeptide, wherein the sequenced portion comprises a position corresponding to position 17,922 according to SEQ ID NO:2, or the complement thereof; ii) the nucleotide sequence of the mRNA molecule encoding the SREBF1 polypeptide, wherein the sequenced portion comprises a position corresponding to position 1,185 according to SEQ ID NO:6, or the complement thereof; iii) the nucleotide sequence of the mRNA molecule encoding the SREBF1 polypeptide, wherein the sequenced portion comprises a position corresponding to position 1,260 according to SEQ ID NO:7, or the complement thereof; iv) the nucleotide sequence of the mRNA molecule encoding the SREBF1 polypeptide, wherein the sequenced portion comprises a position corresponding to position 1,056 according to SEQ ID NO:8, or the complement thereof; v) the nucleotide sequence of the cDNA molecule encoding the SREBF1 polypeptide, wherein the sequenced portion comprises a position corresponding to position 1,185 according to SEQ ID NO:12, or the complement thereof; vi) the nucleotide sequence of the cDNA molecule encoding the SREBF1 polypeptide, wherein the sequenced portion comprises a position corresponding to position 1,260 according to SEQ ID NO:13, or the complement thereof; and/or vii) the nucleotide sequence of the cDNA molecule encoding the SREBF1 polypeptide, wherein the sequenced portion comprises a position corresponding to position 1,056 according to SEQ ID NO:14, or the complement thereof. When the sequenced portion of the SREBF1 genomic nucleic acid molecule in the biological sample comprises: a thymine at a position corresponding to position 17,922 according to SEQ ID NO:2; a uracil at a position corresponding to position 1,185 according to SEQ ID NO:6; a uracil at a position corresponding to position 1,260 according to SEQ ID NO:7; a uracil at a position corresponding to position 1,056 according to SEQ ID NO:8; a thymine at a position corresponding to position 1,185 according to SEQ ID NO:12; a thymine at a position corresponding to position 1,260 according to SEQ ID NO:13; or a thymine at a position corresponding to position 1,056 according to SEQ ID NO:14, then the SREBF1 cDNA molecule in the biological sample is an SREBF1 predicted loss-of-function variant cDNA molecule.

In some embodiments, the detection step, detecting step, or genotyping assay comprises: a) contacting the biological sample with a primer hybridizing to: i) a portion of the nucleotide sequence of the SREBF1 genomic nucleic acid molecule that is proximate to a position corresponding to position 17,922 according to SEQ ID NO:2; ii) a portion of the nucleotide sequence of the SREBF1 mRNA molecule that is proximate to a position corresponding to position 1,185 according to SEQ ID NO:6; iii) a portion of the nucleotide sequence of the SREBF1 mRNA molecule that is proximate to a position corresponding to position 1,260 according to SEQ ID NO:7; iv) a portion of the nucleotide sequence of the SREBF1 mRNA molecule that is proximate to a position corresponding to position 1,056 according to SEQ ID NO:8; v) a portion of the nucleotide sequence of the SREBF1 cDNA molecule that is proximate to a position corresponding to position 1,185 according to SEQ ID NO:12; vi) a portion of the nucleotide sequence of the SREBF1 cDNA molecule that is proximate to a position corresponding to position 1,260 according to SEQ ID NO:13; and/or vii) a portion of the nucleotide sequence of the SREBF1 cDNA molecule that is proximate to a position corresponding to position 1,056 according to SEQ ID NO:14; b) extending the primer at least through: i) the position of the nucleotide sequence of the SREBF1 genomic nucleic acid molecule corresponding to position 17,922 according to SEQ ID NO:2; ii) the position of the nucleotide sequence of the SREBF1 mRNA molecule corresponding to position 1,185 according to SEQ ID NO:6; iii) the position of the nucleotide sequence of the SREBF1 mRNA molecule corresponding to position 1,260 according to SEQ ID NO:7; iv) the position of the nucleotide sequence of the SREBF1 mRNA molecule corresponding to position 1,056 according to SEQ ID NO:8; v) the position of the nucleotide sequence of the SREBF1 cDNA molecule corresponding to position 1,185 according to SEQ ID NO:12; vi) the position of the nucleotide sequence of the SREBF1 cDNA molecule corresponding to position 1,260 according to SEQ ID NO:13; and/or vii) the position of the nucleotide sequence of the SREBF1 cDNA molecule corresponding to position 1,056 according to SEQ ID NO:14; and c) determining whether the extension product of the primer comprises: i) a thymine at a position corresponding to position 17,922 according to SEQ ID NO:2; ii) a uracil at a position corresponding to position 1,185 according to SEQ ID NO:6; iii) a uracil at a position corresponding to position 1,260 according to SEQ ID NO:7; iv) a uracil at a position corresponding to position 1,056 according to SEQ ID NO:8; v) a thymine at a position corresponding to position 1,185 according to SEQ ID NO:12; vi) a thymine at a position corresponding to position 1,260 according to SEQ ID NO:13; and/or vii) a thymine at a position corresponding to position 1,056 according to SEQ ID NO:14. In some embodiments, the determining step comprises sequencing the entire nucleic acid molecule.

In some embodiments, the detection step, detecting step, or genotyping assay comprises: a) amplifying at least a portion of the nucleic acid molecule that encodes the human SREBF1 polypeptide, wherein the portion comprises: i) a thymine at a position corresponding to position 17,922 according to SEQ ID NO:2, or the complement thereof; ii) a uracil at a position corresponding to position 1,185 according to SEQ ID NO:6, or the complement thereof; iii) a uracil at a position corresponding to position 1,260 according to SEQ ID NO:7, or the complement thereof; iv) a uracil at a position corresponding to position 1,056 according to SEQ ID NO:8, or the complement thereof; v) a thymine at a position corresponding to position 1,185 according to SEQ ID NO:12, or the complement thereof; vi) a thymine at a position corresponding to position 1,260 according to SEQ ID NO:13, or the complement thereof; and/or vii) a thymine at a position corresponding to position 1,056 according to SEQ ID NO:14, or the complement thereof; b) labeling the amplified nucleic acid molecule with a detectable label; c) contacting the labeled nucleic acid molecule with a support comprising an alteration-specific probe, wherein the alteration-specific probe comprises a nucleotide sequence which hybridizes under stringent conditions to: i) the nucleotide sequence of the amplified nucleic acid molecule comprising a thymine at a position corresponding to position 17,922 according to SEQ ID NO:2, or the complement thereof; ii) the nucleotide sequence of the amplified nucleic acid molecule comprising a uracil at a position corresponding to position 1,185 according to SEQ ID NO:6, or the complement thereof; iii) the nucleotide sequence of the amplified nucleic acid molecule comprising a uracil at a position corresponding to position 1,260 according to SEQ ID NO:7, or the complement thereof; iv) the nucleotide sequence of the amplified nucleic acid molecule comprising a uracil at a position corresponding to position 1,056 according to SEQ ID NO:8, or the complement thereof; v) the nucleotide sequence of the amplified nucleic acid molecule comprising a thymine at a position corresponding to position 1,185 according to SEQ ID NO:12, or the complement thereof; vi) the nucleotide sequence of the amplified nucleic acid molecule comprising a thymine at a position corresponding to position 1,260 according to SEQ ID NO:13, or the complement thereof; and/or vii) the nucleotide sequence of the amplified nucleic acid molecule comprising a thymine at a position corresponding to position 1,056 according to SEQ ID NO:14, or the complement thereof; and d) detecting the detectable label. In some embodiments, the nucleic acid molecule is mRNA and the determining step further comprises reverse-transcribing the mRNA into a cDNA prior to the amplifying step.

In some embodiments, the detection step, detecting step, or genotyping assay comprises: contacting the nucleic acid molecule in the biological sample with an alteration-specific probe comprising a detectable label, wherein the alteration-specific probe comprises a nucleotide sequence which hybridizes under stringent conditions to: i) the nucleotide sequence of the amplified nucleic acid molecule comprising a thymine at a position corresponding to position 17,922 according to SEQ ID NO:2, or the complement thereof; ii) the nucleotide sequence of the amplified nucleic acid molecule comprising a uracil at a position corresponding to position 1,185 according to SEQ ID NO:6, or the complement thereof; iii) the nucleotide sequence of the amplified nucleic acid molecule comprising a uracil at a position corresponding to position 1,260 according to SEQ ID NO:7, or the complement thereof; iv) the nucleotide sequence of the amplified nucleic acid molecule comprising a uracil at a position corresponding to position 1,056 according to SEQ ID NO:8, or the complement thereof; v) the nucleotide sequence of the amplified nucleic acid molecule comprising a thymine at a position corresponding to position 1,185 according to SEQ ID NO:12, or the complement thereof; vi) the nucleotide sequence of the amplified nucleic acid molecule comprising a thymine at a position corresponding to position 1,260 according to SEQ ID NO:13, or the complement thereof; and/or vii) the nucleotide sequence of the amplified nucleic acid molecule comprising a thymine at a position corresponding to position 1,056 according to SEQ ID NO:14, or the complement thereof; and detecting the detectable label.

In any of these embodiments, the nucleic acid molecule can be present within a cell obtained from the human subject.

In any of the embodiments described herein, the increased lipid level is increased serum lipid level, increased total cholesterol, or increased LDL. In some embodiments, the increased lipid level is increased serum lipid level. In some embodiments, the increased lipid level is increased total cholesterol. In some embodiments, the increased lipid level is increased serum cholesterol. In some embodiments, the increased lipid level is increased LDL.

In some embodiments, increased lipid levels include hyperlipidemia, such as hypercholesterolemia (elevated cholesterol). Increased lipid levels also include hyperlipoproteinemia, which refers to the presence of elevated lipoproteins (usually LDL).

For human subjects that are genotyped or determined to be either SREBF1 reference or heterozygous for an SREBF1 predicted loss-of-function variant, such human subjects can be treated with an SREBF1 inhibitor, as described herein.

Examples of therapeutic agents that treat or inhibit an increased lipid level include, but are not limited to: a spirocyclic azetidinone derivative, a statin, a PPAR agonist, nicotinic acid, niacin, ezetimibe, a PCSK9 inhibitor, an RXR agonist, a hormone, a sulfonylurea-based drug, a biguanide, an α-glucosidase inhibitor, a GLP-1 agonist, and a PPARα/δ dual agonist, or any combination thereof.

Spirocyclic azetidinone derivatives include, but are not limited to those disclosed in, for example, U.S. RE 37,721; U.S. Pat. Nos. 5,631,356; 5,767,115; 5,846,966; 5,698,548; 5,633,246; 5,656,624; 5,624,920; 5,688,787; and 5,756,470; U.S. Publication No. 2002/0137689; and PCT Publication Nos. WO 02/066464, WO 95/08522, and WO96/19450.

Statins include, but are not limited to, atorvastatin, fluvastatin, lovastatin, pitavastatin, pravastatin, rosuvastatin, cerivastatin, and simvastatin.

PPAR agonists include, but are not limited to, a thiazolidinedione or a fibrate. Thiazolidinediones include, but are not limited to, 5-((4-(2-(methyl-2-pyridinylamino) ethoxy) phenyl)methyl)-2,4-thiazolidinedione, troglitazone, pioglitazone, ciglitazone, WAY-120,744, englitazone, AD 5075, darglitazone, and rosiglitazone. Fibrates include, but are not limited to, gemfibrozil, fenofibrate, clofibrate, and ciprofibrate.

RXR agonists include, but are not limited to, LG 100268, LGD 1069, 9-cis retinoic acid, 2-(1-(3,5,5,8,8-pentamethyl-5,6,7,8-tetrahydro-2-naphthyl)-cyclopropyl)-pyridine-5-carboxylic acid, and 4-((3,5,5,8,8-pentamethyl-5,6,7,8-tetrahydro-2-naphthyl)2-carbonyl)-benzoic acid.

Hormones include, but are not limited to, thyroid hormone, estrogen and insulin. Suitable insulins include, but are not limited, to injectable insulin, transdermal insulin, and inhaled insulin, or any combination thereof. As an alternative to insulin, an insulin derivative, secretagogue, sensitizer or mimetic may be used. Insulin secretagogues include, but are not limited to, forskolin, dibutryl cAMP, and isobutylmethylxanthine (IBMX).

Sulfonylurea-based drugs include, but are not limited to, glisoxepid, glyburide, acetohexamide, chlorpropamide, glibornuride, tolbutamide, tolazamide, glipizide, gliclazide, gliquidone, glyhexamide, phenbutamide, and tolcyclamide.

Biguanides include, but are not limited to, metformin, phenformin and buformin.

α-glucosidase inhibitors include, but are not limited to, acarbose and miglitol.

GLP-1 agonists include, but are not limited to, VICTOZA® and SAXENDA® (liraglutide), BYETTA® and BYDUREON© (exenatide), LYXUMIA® (lixisenatide), TANZEUM© (albiglutide), TRULICITY© (dulaglutide), and OZEMPIC® (semaglutide).

For human subjects that are genotyped or determined to be either SREBF1 reference or heterozygous for an SREBF1 predicted loss-of-function variant, such human subjects can also be treated with any one or more of the SREBF1 predicted loss-of-function polypeptides described herein.

In some embodiments, the dose of the therapeutic agents that treat or inhibit the increased lipid level can be reduced by about 10%, by about 20%, by about 30%, by about 40%, by about 50%, by about 60%, by about 70%, by about 80%, or by about 90% for subjects that are heterozygous for an SREBF1 predicted loss-of-function variant nucleic acid molecule (i.e., a lower than the standard dosage amount) compared to subjects that are SREBF1 reference (who may receive a standard dosage amount). In some embodiments, the dose of the therapeutic agents that treat or inhibit the increased lipid level can be reduced by about 10%, by about 20%, by about 30%, by about 40%, or by about 50%. In addition, the dose of therapeutic agents that treat or inhibit the increased lipid level in subjects that are heterozygous for an SREBF1 predicted loss-of-function variant nucleic acid molecule can be administered less frequently compared to subjects that are SREBF1 reference.

Administration of the therapeutic agents that treat or inhibit the increased lipid level and/or SREBF1 inhibitors can be repeated, for example, after one day, two days, three days, five days, one week, two weeks, three weeks, one month, five weeks, six weeks, seven weeks, eight weeks, two months, or three months. The repeated administration can be at the same dose or at a different dose. The administration can be repeated once, twice, three times, four times, five times, six times, seven times, eight times, nine times, ten times, or more. For example, according to certain dosage regimens a subject can receive therapy for a prolonged period of time such as, for example, 6 months, 1 year, or more.

Administration of the therapeutic agents that treat or inhibit the increased lipid level and/or SREBF1 inhibitors can occur by any suitable route including, but not limited to, parenteral, intravenous, oral, subcutaneous, intra-arterial, intracranial, intrathecal, intraperitoneal, topical, intranasal, or intramuscular. Pharmaceutical compositions for administration are desirably sterile and substantially isotonic and manufactured under GMP conditions. Pharmaceutical compositions can be provided in unit dosage form (i.e., the dosage for a single administration). Pharmaceutical compositions can be formulated using one or more physiologically and pharmaceutically acceptable carriers, diluents, excipients or auxiliaries. The formulation depends on the route of administration chosen. The term "pharmaceutically acceptable" means that the carrier, diluent, excipient, or auxiliary is compatible with the other ingredients of the formulation and not substantially deleterious to the recipient thereof.

The terms "treat", "treating", and "treatment" and "prevent", "preventing", and "prevention" as used herein, refer to eliciting the desired biological response, such as a therapeutic and prophylactic effect, respectively. In some embodiments, a therapeutic effect comprises one or more of a decrease/reduction in an increased lipid level, a decrease/reduction in the severity of an increased lipid level (such as, for example, a reduction or inhibition of development or an increased lipid level), a decrease/reduction in symptoms and increased lipid level-related effects, delaying the onset of symptoms and increased lipid level-related effects, reducing the severity of symptoms of the increased lipid level-related effects, reducing the severity of an acute episode, reducing the number of symptoms and increased lipid level-related effects, reducing the latency of symptoms and increased lipid level-related effects, an amelioration of symptoms and increased lipid level-related effects, reducing secondary symptoms, reducing secondary infections, preventing relapse to an increased lipid level, decreasing the number or frequency of relapse episodes, increasing latency between symptomatic episodes, increasing time to sustained progression, expediting remission, inducing remission, augmenting remission, speeding recovery, or increasing efficacy of or decreasing resistance to alternative therapeutics, and/or an increased survival time of the affected host animal, following administration of the agent or composition comprising the agent. A prophylactic effect may comprise a complete or partial avoidance/inhibition or a delay of increased lipid level development/progression (such as, for example, a complete or partial avoidance/inhibition or a delay), and an increased survival time of the affected host animal, following administration of a therapeutic protocol. Treatment of an increased lipid level encompasses the treatment of subjects already diagnosed as having any form of the increased lipid level at any clinical stage or manifestation, the delay of the onset or evolution or aggravation or deterioration of the symptoms or signs of the increased lipid level, and/or preventing and/or reducing the severity of the increased lipid level.

In some embodiments, the methods comprise detecting the presence or absence of an SREBF1 polypeptide in a biological sample from the subject, wherein the SREBF1 polypeptide comprises: i) a cysteine at a position corresponding to position 334 according to SEQ ID NO:18; ii) a cysteine at a position corresponding to position 364 according to SEQ ID NO:19; or iii) a cysteine at a position corresponding to position 310 according to SEQ ID NO:20; wherein: when the human subject does not have the SREBF1 polypeptide, then the human subject has an increased risk for developing an increased lipid level; and when the human subject has the SREBF1 polypeptide, then the human subject has a decreased risk for developing an increased lipid level.

In some embodiments, the detecting step comprises sequencing at least a portion of the polypeptide that comprises: i) a position corresponding to position 334 according to SEQ ID NO:18; ii) a position corresponding to position 364 according to SEQ ID NO:19; or iii) a position corresponding to position 310 according to SEQ ID NO:20. In some embodiments, the detecting step comprises sequencing the entire polypeptide. In some embodiments, the detecting step comprises an immunoassay for detecting the presence of a polypeptide that comprises: i) a position corresponding to position 334 according to SEQ ID NO:18; ii) a position corresponding to position 364 according to SEQ ID NO:19; or iii) a position corresponding to position 310 according to SEQ ID NO:20.

The present disclosure also provides methods of identifying a human subject having an increased risk for developing an increased lipid level, wherein the method comprises any of the methods described herein for detecting the presence or absence of any of the SREBF1 predicted loss-of-function variant nucleic acid molecules (such as a genomic nucleic acid molecule, mRNA molecule, and/or cDNA molecule) described herein. Determining or having determined in a sample obtained from the subject the presence or absence of the particular nucleic acid molecules can be carried out by any of the methods described herein. When the human subject lacks an SREBF1 predicted loss-of-function variant nucleic acid molecule (i.e., the human subject is genotypically categorized as an SREBF1 reference), then the human subject has an increased risk for developing an increased lipid level. When the human subject has an SREBF1 predicted loss-of-function variant nucleic acid molecule (i.e., the human subject is categorized as heterozygous for an SREBF1 predicted loss-of-function variant or homozygous for an SREBF1 predicted loss-of-function variant), then the human subject has a decreased risk for developing an increased lipid level. Having a single copy of an SREBF1 predicted loss-of-function variant nucleic acid molecule is more protective of a human subject from developing an increased lipid level than having no copies of an SREBF1 predicted loss-of-function variant nucleic acid molecule.

Without intending to be limited to any particular theory or mechanism of action, it is believed that a single copy of an SREBF1 predicted loss-of-function variant nucleic acid molecule (i.e., heterozygous for an SREBF1 predicted loss-of-function variant) is protective of a human subject from developing an increased lipid level, and it is also believed that having two copies of an SREBF1 predicted loss-of-function variant nucleic acid molecule (i.e., homozygous for an SREBF1 predicted loss-of-function variant) may be more protective of a human subject from developing an increased lipid level, relative to a human subject with a single copy. Thus, in some embodiments, a single copy of an SREBF1 predicted loss-of-function variant nucleic acid molecule may not be completely protective, but instead, may be partially or incompletely protective of a human subject from developing an increased lipid level. While not desiring to be bound by any particular theory, there may be additional factors or molecules involved in the development of increased lipid level that are still present in a human subject having a single copy of an SREBF1 predicted loss-of-function variant nucleic acid molecule, thus resulting in less than complete protection from the development of increased lipid level.

The present disclosure also provides methods of identifying a human subject having an increased risk for developing an increased lipid level, wherein the method comprises: detecting the presence or absence of an SREBF1 predicted loss-of-function variant polypeptide in a biological sample from the subject, wherein the SREBF1 predicted loss-of-function variant polypeptide comprises: i) a cysteine at a position corresponding to position 334 according to SEQ ID NO:18; ii) a cysteine at a position corresponding to position 364 according to SEQ ID NO:19; or iii) a cysteine at a position corresponding to position 310 according to SEQ ID NO:20; wherein: when the human subject does not have an SREBF1 predicted loss-of-function variant polypeptide, then the human subject has an increased risk for developing an increased lipid level; and when the human subject has an SREBF1 predicted loss-of-function variant polypeptide, then the human subject has a decreased risk for developing an increased lipid level.

In some embodiments, the determining step comprises sequencing at least a portion of the polypeptide that comprises a position corresponding to position 334 according to SEQ ID NO:18. In some embodiments, the determining step comprises sequencing at least a portion of the polypeptide that comprises a position corresponding to position 364 according to SEQ ID NO:19. In some embodiments, the determining step comprises sequencing at least a portion of the polypeptide that comprises a position corresponding to position 310 according to SEQ ID NO:20. In some embodiments, the determining step comprises sequencing the entire polypeptide. In some embodiments, the determining step comprises an immunoassay.

In some embodiments, the human subject is further treated with a therapeutic agent that treats or inhibits the increased lipid level and/or an SREBF1 inhibitor, as described herein. For example, when the human subject is SREBF1 reference, and therefore has an increased risk for developing an increased lipid level, the human subject is administered a SREBF1 inhibitor. In some embodiments, such a subject is also administered a therapeutic agent that treats or inhibits the increased lipid level. In some embodiments, when the subject is heterozygous for an SREBF1 predicted loss-of-function variant, the subject is administered the therapeutic agent that treats or inhibits the increased lipid level in a dosage amount that is the same as or lower than the standard dosage amount, and is also administered a SREBF1 inhibitor. In some embodiments, the subject is SREBF1 reference. In some embodiments, the subject is heterozygous for an SREBF1 predicted loss-of-function variant.

The present disclosure also provides methods of detecting the presence of an SREBF1 predicted loss-of-function variant genomic nucleic acid molecule, an SREBF1 predicted loss-of-function variant mRNA molecule, and/or an SREBF1 predicted loss-of-function variant cDNA molecule in a biological sample from a subject human. It is understood that gene sequences within a population and mRNA molecules encoded by such genes can vary due to polymorphisms such as single-nucleotide polymorphisms. The sequences provided herein for the SREBF1 variant genomic nucleic acid molecule, SREBF1 variant mRNA molecule, and SREBF1 variant cDNA molecule are only exemplary sequences. Other sequences for the SREBF1 variant genomic nucleic acid molecule, variant mRNA molecule, and variant cDNA molecule are also possible.

The biological sample can be derived from any cell, tissue, or biological fluid from the subject. The sample may comprise any clinically relevant tissue, such as a bone marrow sample, a tumor biopsy, a fine needle aspirate, or a sample of bodily fluid, such as blood, gingival crevicular fluid, plasma, serum, lymph, ascitic fluid, cystic fluid, or urine. In some cases, the sample comprises a buccal swab. The sample used in the methods disclosed herein will vary based on the assay format, nature of the detection method, and the tissues, cells, or extracts that are used as the sample. A biological sample can be processed differently depending on the assay being employed. For example, when detecting any SREBF1 variant nucleic acid molecule, preliminary processing designed to isolate or enrich the sample for the genomic DNA can be employed. A variety of known techniques may be used for this purpose. When detecting the level of any SREBF1 variant mRNA, different techniques can be used enrich the biological sample with mRNA. Various methods to detect the presence or level of a mRNA or the presence of a particular variant genomic DNA locus can be used.

In some embodiments, the methods of detecting a human SREBF1 predicted loss-of-function variant nucleic acid molecule in a human subject comprise assaying a biological sample obtained from the human subject to determine whether an SREBF1 genomic nucleic acid molecule, an SREBF1 mRNA molecule, or an SREBF1 cDNA molecule in the biological sample comprises one or more variations that cause a loss-of-function (partial or complete) or are predicted to cause a loss-of-function (partial or complete). For example, in some embodiments, the methods of detecting a human SREBF1 predicted loss-of-function variant nucleic acid molecule in a human subject comprise assaying a biological sample obtained from the subject to determine whether an SREBF1 nucleic acid molecule in the biological sample comprises a nucleotide sequence comprising: i) a thymine at a position corresponding to position 17,922 according to SEQ ID NO:2, or the complement thereof, ii) a uracil at a position corresponding to position 1,185 according to SEQ ID NO:6, or the complement thereof, iii) a uracil at a position corresponding to position 1,260 according to SEQ ID NO:7, or the complement thereof, iv) a uracil at a position corresponding to position 1,056 according to SEQ ID NO:8, or the complement thereof, v) a thymine at a position corresponding to position 1,185 according to SEQ ID NO:12, or the complement thereof, vi) a thymine at a position corresponding to position 1,260 according to SEQ ID NO:13, or the complement thereof, or vii) a thymine at a position corresponding to position 1,056 according to SEQ ID NO:14, or the complement thereof. In some embodiments, the method is an in vitro method.

In some embodiments, the methods of detecting the presence or absence of an SREBF1 predicted loss-of-function variant nucleic acid molecule (such as, for example, a genomic nucleic acid molecule, an mRNA molecule, and/or a cDNA molecule) in a human subject, comprise: performing an assay on a biological sample obtained from the subject, which assay determines whether a nucleic acid molecule in the biological sample comprises a nucleotide sequence that encodes: i) a thymine at a position corresponding to position 17,922 according to SEQ ID NO:2; ii) a uracil at a position corresponding to position 1,185 according to SEQ ID NO:6; iii) a uracil at a position corresponding to position 1,260 according to SEQ ID NO:7; iv) a uracil at a position corresponding to position 1,056 according to SEQ ID NO:8; v) a thymine at a position corresponding to position 1,185 according to SEQ ID NO:12; vi) a thymine at a position corresponding to position 1,260 according to SEQ ID NO:13; or vii) a thymine at a position corresponding to position 1,056 according to SEQ ID NO:14. In some embodiments, the biological sample comprises a cell or cell lysate. Such methods can further comprise, for example, obtaining a biological sample from the subject comprising an SREBF1 genomic nucleic acid molecule or mRNA molecule, and if mRNA, optionally reverse transcribing the mRNA into cDNA, and performing an assay on the biological sample that determines that a position of the SREBF1 genomic nucleic acid molecule, mRNA, or cDNA encodes: i) a thymine at a position corresponding to position 17,922 according to SEQ ID NO:2; ii) a uracil at a position corresponding to position 1,185 according to SEQ ID NO:6; iii) a uracil at a position corresponding to position 1,260 according to SEQ ID NO:7; iv) a uracil at a position corresponding to position 1,056 according to SEQ ID NO:8; v) a thymine at a position corresponding to position 1,185 according to SEQ ID NO:12; vi) a thymine at a position corresponding to position 1,260 according to SEQ ID NO:13; or vii) a thymine at a position corresponding to position 1,056 according to SEQ ID NO:14. Such assays can comprise, for example determining the identity of these positions of the particular SREBF1 nucleic acid molecule. In some embodiments, the method is an in vitro method.

In some embodiments, the assay comprises sequencing at least a portion of the nucleotide sequence of the SREBF1 genomic nucleic acid molecule, the SREBF1 mRNA molecule, or the SREBF1 cDNA molecule in the biological sample, wherein the sequenced portion comprises one or more variations that cause a loss-of-function (partial or complete). For example, in some embodiments, the assay comprises sequencing at least a portion of: i) the nucleotide sequence of the SREBF1 genomic nucleic acid molecule in the biological sample, wherein the sequenced portion comprises a position corresponding to position 17,922 according to SEQ ID NO:2, or the complement thereof; ii) the nucleotide sequence of an SREBF1 mRNA molecule in the biological sample, wherein the sequenced portion comprises a position corresponding to position 1,185 according to SEQ ID NO:6, or the complement thereof; iii) the nucleotide sequence of an SREBF1 mRNA molecule in the biological sample, wherein the sequenced portion comprises a position corresponding to position 1,260 according to SEQ ID NO:7, or the complement thereof; iv) the nucleotide sequence of an SREBF1 mRNA molecule in the biological sample, wherein the sequenced portion comprises a position corresponding to position 1,056 according to SEQ ID NO:8, or the complement thereof; v) the nucleotide sequence of an SREBF1 cDNA molecule in the biological sample, wherein the sequenced portion comprises a position corresponding to position 1,185 according to SEQ ID NO:12, or the complement thereof; vi) the nucleotide sequence of an SREBF1 cDNA molecule in the biological sample, wherein the sequenced portion comprises a position corresponding to position 1,260 according to SEQ ID NO:13, or the complement thereof; and/or vii) the nucleotide sequence of an SREBF1 cDNA molecule in the biological sample, wherein the sequenced portion comprises a position corresponding to position 1,056 according to SEQ ID NO:14, or the complement thereof. When the sequenced portion of the SREBF1 genomic nucleic acid molecule in the biological sample comprises a thymine at a position corresponding to position 17,922 according to SEQ ID NO:2, then the SREBF1 genomic nucleic acid molecule in the biological sample is an SREBF1 predicted loss-of-function variant genomic nucleic acid molecule. When the sequenced portion of an SREBF1 mRNA molecule in the biological sample comprises a uracil at a position corresponding to position 1,185 according to SEQ ID NO:6, then the SREBF1 mRNA molecule in the biological sample is an SREBF1 predicted loss-of-function variant mRNA molecule. When the sequenced portion of an SREBF1 mRNA molecule in the biological sample comprises a uracil at a position corresponding to position 1,260 according to SEQ ID NO:7, then the SREBF1 mRNA molecule in the biological sample is an SREBF1 predicted loss-of-function variant mRNA molecule. When the sequenced portion of an SREBF1 mRNA molecule in the biological sample comprises a uracil at a position corresponding to position 1,056 according to SEQ ID NO:8, then the SREBF1 mRNA molecule in the biological sample is an SREBF1 predicted loss-of-function variant mRNA molecule. When the sequenced portion of an SREBF1 cDNA molecule in the biological sample comprises a thymine at a position corresponding to position 1,185 according to SEQ ID NO:12, then the SREBF1 cDNA molecule in the biological sample is an SREBF1 predicted loss-of-function variant cDNA molecule. When the sequenced portion of an SREBF1 cDNA molecule in the biological sample comprises a thymine at a position corresponding to position 1,260 according to SEQ ID NO:13, then the SREBF1 cDNA molecule in the biological sample is an SREBF1 predicted loss-of-function variant cDNA molecule. When the sequenced portion of an SREBF1 cDNA molecule in the biological sample comprises a thymine at a position corresponding to position 1,056 according to SEQ ID NO:14, then the SREBF1 cDNA molecule in the biological sample is an SREBF1 predicted loss-of-function variant cDNA molecule.

In some embodiments, the assay comprises: a) contacting the sample with a primer hybridizing to: i) a portion of the nucleotide sequence of SREBF1 genomic nucleic acid molecule that is proximate to a position corresponding to position 17,922 according to SEQ ID NO:2; ii) a portion of the nucleotide sequence of SREBF1 mRNA molecule that is proximate to a position corresponding to position 1,185 according to SEQ ID NO:6; iii) a portion of the nucleotide sequence of SREBF1 mRNA molecule that is proximate to a position corresponding to position 1,260 according to SEQ ID NO:7; iv) a portion of the nucleotide sequence of SREBF1 mRNA molecule that is proximate to a position corresponding to position 1,056 according to SEQ ID NO:8; v) a portion of the nucleotide sequence of SREBF1 cDNA molecule that is proximate to a position corresponding to position 1,185 according to SEQ ID NO:12; vi) a portion of the nucleotide sequence of SREBF1 cDNA molecule that is proximate to a position corresponding to position 1,260 according to SEQ ID NO:13; or vii) a portion of the nucleotide sequence of SREBF1 cDNA molecule that is proximate to a position corresponding to position 1,056 according to SEQ ID NO:14; b) extending the primer at least through: i) the position of the nucleotide sequence of SREBF1 genomic nucleic acid molecule corresponding to position 17,922 according to SEQ ID NO:2; ii) the position of the nucleotide sequence of SREBF1 mRNA molecule corresponding to position 1,185 according to SEQ ID NO:6; iii) the position of the nucleotide sequence of SREBF1 mRNA molecule corresponding to position 1,260 according to SEQ ID NO:7; iv) the position of the nucleotide sequence of SREBF1 mRNA molecule corresponding to position 1,056 according to SEQ ID NO:8; v) the position of the nucleotide sequence of SREBF1 cDNA molecule corresponding to position 1,185 according to SEQ ID NO:12; vi) the position of the nucleotide sequence of SREBF1 cDNA molecule corresponding to position 1,260 according to SEQ ID NO:13; or vii) the position of the nucleotide sequence of SREBF1 cDNA molecule corresponding to position 1,056 according to SEQ ID NO:14; and c) determining whether the extension product of the primer comprises: i) a thymine at a position corresponding to position 17,922 according to SEQ ID NO:2; ii) a uracil at a position corresponding to position 1,185 according to SEQ ID NO:6; iii) a uracil at a position corresponding to position 1,260 according to SEQ ID NO:7; iv) a uracil at a position corresponding to position 1,056 according to SEQ ID NO:8; v) a thymine at a position corresponding to position 1,185 according to SEQ ID NO:12; vi) a thymine at a position corresponding to position 1,260 according to SEQ ID NO:13; vii) a thymine at a position corresponding to position 1,056 according to SEQ ID NO:14. In some embodiments, the assay comprises sequencing the entire nucleic acid molecule. In some embodiments, only SREBF1 genomic nucleic acid molecule is analyzed. In some embodiments, only SREBF1 mRNA is analyzed. In some embodiments, only SREBF1 cDNA obtained from SREBF1 mRNA is analyzed.

In some embodiments, the assay comprises: a) amplifying at least a portion of the nucleic acid molecule that encodes the human SREBF1 polypeptide, wherein the portion comprises: i) a thymine at a position corresponding to position 17,922 according to SEQ ID NO:2, or the complement thereof; ii) a uracil at a position corresponding to position 1,185 according to SEQ ID NO:6, or the complement thereof; iii) a uracil at a position corresponding to position 1,260 according to SEQ ID NO:7, or the complement thereof; iv) a uracil at a position corresponding to position 1,056 according to SEQ ID NO:8, or the complement thereof; v) a thymine at a position corresponding to position 1,185 according to SEQ ID NO:12, or the complement thereof; v) a thymine at a position corresponding to position 1,260 according to SEQ ID NO:13, or the complement thereof; v) a thymine at a position corresponding to position 1,056 according to SEQ ID NO:14, or the complement thereof; b) labeling the amplified nucleic acid molecule with a detectable label; c) contacting the labeled nucleic acid molecule with a support comprising an alteration-specific probe, wherein the alteration-specific probe comprises a nucleotide sequence which hybridizes under stringent conditions to: i) the nucleic acid sequence of the amplified nucleic acid molecule comprising a thymine at a position corresponding to position 17,922 according to SEQ ID NO:2, or the complement thereof; ii) the nucleic acid sequence of the amplified nucleic acid molecule comprising a uracil at a position corresponding to position 1,185 according to SEQ ID NO:6, or the complement thereof; iii) the nucleic acid sequence of the amplified nucleic acid molecule comprising a uracil at a position corresponding to position 1,260 according to SEQ ID NO:7, or the complement thereof; iv) the nucleic acid sequence of the amplified nucleic acid molecule comprising a uracil at a position corresponding to position 1,056 according to SEQ ID NO:8, or the complement thereof; v) the nucleic acid sequence of the amplified nucleic acid molecule comprising a thymine at a position corresponding to position 1,185 according to SEQ ID NO:12, or the complement thereof; vi) the nucleic acid sequence of the amplified nucleic acid molecule comprising a thymine at a position corresponding to position 1,260 according to SEQ ID NO:13, or the complement thereof; vii) the nucleic acid sequence of the amplified nucleic acid molecule comprising a thymine at a position corresponding to position 1,056 according to SEQ ID NO:14, or the complement thereof; and d) detecting the detectable label. In some embodiments, the nucleic acid molecule is mRNA and the determining step further comprises reverse-transcribing the mRNA into a cDNA prior to the amplifying step.

In some embodiments, the assay comprises: contacting the nucleic acid molecule in the biological sample with an alteration-specific probe comprising a detectable label, wherein the alteration-specific probe comprises a nucleotide sequence which hybridizes under stringent conditions to: i) the nucleotide sequence of the amplified nucleic acid molecule comprising a thymine at a position corresponding to position 17,922 according to SEQ ID NO:2, or the complement thereof; ii) the nucleotide sequence of the amplified nucleic acid molecule comprising a uracil at a position corresponding to position 1,185 according to SEQ ID NO:6, or the complement thereof; iii) the nucleotide sequence of the amplified nucleic acid molecule comprising a uracil at a position corresponding to position 1,260 according to SEQ ID NO:7, or the complement thereof; iv) the nucleotide sequence of the amplified nucleic acid molecule comprising a uracil at a position corresponding to position 1,056 according to SEQ ID NO:8, or the complement thereof; v) the nucleotide sequence of the amplified nucleic acid molecule comprising a thymine at a position corresponding to position 1,185 according to SEQ ID NO:12, or the complement thereof; vi) the nucleotide sequence of the amplified nucleic acid molecule comprising a thymine at a position corresponding to position 1,260 according to SEQ ID NO:13, or the complement thereof; vii) the nucleotide sequence of the amplified nucleic acid molecule comprising a thymine at a position corresponding to position 1,056 according to SEQ ID NO:14, or the complement thereof; and detecting the detectable label. Alteration-specific polymerase chain reaction techniques can be used to detect mutations such as SNPs in a nucleic acid sequence. Alteration-specific primers can be used because the DNA polymerase will not extend when a mismatch with the template is present.

In some embodiments, the nucleic acid molecule in the sample is mRNA and the mRNA is reverse-transcribed into a cDNA prior to the amplifying step. In some embodiments, the nucleic acid molecule is present within a cell obtained from the human subject.

The SREBF1 predicted loss-of-function variant nucleic acid molecule can be any SREBF1 nucleic acid molecule (such as, for example, genomic nucleic acid molecule, mRNA molecule, or cDNA molecule) encoding an SREBF1 polypeptide having a partial loss-of-function, a complete loss-of-function, a predicted partial loss-of-function, or a predicted complete loss-of-function. For example, the SREBF1 predicted loss-of-function variant nucleic acid molecule can be any nucleic acid molecule encoding SREBF1 Arg334Cys, Arg364Cys, or Arg310Cys.

In some embodiments, the assay comprises contacting the biological sample with a primer or probe, such as an alteration-specific primer or alteration-specific probe, that specifically hybridizes to an SREBF1 variant genomic sequence, variant mRNA sequence, or variant cDNA sequence and not the corresponding SREBF1 reference sequence under stringent conditions, and determining whether hybridization has occurred.

In some embodiments, the assay comprises RNA sequencing (RNA-Seq). In some embodiments, the assays also comprise reverse transcribing mRNA into cDNA, such as by the reverse transcriptase polymerase chain reaction (RT-PCR).

In some embodiments, the methods utilize probes and primers of sufficient nucleotide length to bind to the target nucleotide sequence and specifically detect and/or identify a polynucleotide comprising an SREBF1 variant genomic nucleic acid molecule, variant mRNA molecule, or variant cDNA molecule. The hybridization conditions or reaction conditions can be determined by the operator to achieve this result. This nucleotide length may be any length that is sufficient for use in a detection method of choice, including any assay described or exemplified herein. Such probes and primers can hybridize specifically to a target nucleotide sequence under high stringency hybridization conditions. Probes and primers may have complete nucleotide sequence identity of contiguous nucleotides within the target nucleotide sequence, although probes differing from the target nucleotide sequence and that retain the ability to specifically detect and/or identify a target nucleotide sequence may be designed by conventional methods. Accordingly, probes and primers can share about 80%, about 85%, about 90%, about 91%, about 92%, about 93%, about 94%, about 95%, about 96%, about 97%, about 98%, about 99%, or 100% sequence identity or complementarity to the nucleotide sequence of the target nucleic acid molecule.

In some embodiments, to determine whether the SREBF1 nucleic acid molecule (genomic nucleic acid molecule, mRNA molecule, or cDNA molecule), or complement thereof, within a biological sample comprises a nucleotide sequence encoding a thymine at a position corresponding to position 17,922 according to SEQ ID NO:2, a uracil at a position corresponding to position 1,185 according to SEQ ID NO:6, a uracil at a position corresponding to position 1,260 according to SEQ ID NO:7, a uracil at a position corresponding to position 1,056 according to SEQ ID NO:8, a thymine at a position corresponding to position 1,185 according to SEQ ID NO:12, a thymine at a position corresponding to position 1,260 according to SEQ ID NO:13, or a thymine at a position corresponding to position 1,056 according to SEQ ID NO:14, the biological sample may be subjected to an amplification method using a primer pair that includes a first primer derived from the 5' flanking sequence adjacent to a thymine at a position corresponding to position 17,922 according to SEQ ID NO:2, a uracil at a position corresponding to position 1,185 according to SEQ ID NO:6, a uracil at a position corresponding to position 1,260 according to SEQ ID NO:7, a uracil at a position corresponding to position 1,056 according to SEQ ID NO:8, a thymine at a position corresponding to position 1,185 according to SEQ ID NO:12, a thymine at a position corresponding to position 1,260 according to SEQ ID NO:13, or a thymine at a position corresponding to position 1,056 according to SEQ ID NO:14, and a second primer derived from the 3' flanking sequence adjacent to a thymine at a position corresponding to position 17,922 according to SEQ ID NO:2, a uracil at a position corresponding to position 1,185 according to SEQ ID NO:6, a uracil at a position corresponding to position 1,260 according to SEQ ID NO:7, a uracil at a position corresponding to position 1,056 according to SEQ ID NO:8, a thymine at a position corresponding to position 1,185 according to SEQ ID NO:12, a thymine at a position corresponding to position 1,260 according to SEQ ID NO:13, or a thymine at a position corresponding to position 1,056 according to SEQ ID NO:14, to produce an amplicon that is indicative of the presence of the SNP at positions encoding a thymine at a position corresponding to position 17,922 according to SEQ ID NO:2, a uracil at a position corresponding to position 1,185 according to SEQ ID NO:6, a uracil at a position corresponding to position 1,260 according to SEQ ID NO:7, a uracil at a position corresponding to position 1,056 according to SEQ ID NO:8, a thymine at a position corresponding to position 1,185 according to SEQ ID NO:12, a thymine at a position corresponding to position 1,260 according to SEQ ID NO:13, or a thymine at a position corresponding to position 1,056 according to SEQ ID NO:14. In some embodiments, the amplicon may range in length from the combined length of the primer pairs plus one nucleotide base pair to any length of amplicon producible by a DNA amplification protocol. This distance can range from one nucleotide base pair up to the limits of the amplification reaction, or about twenty thousand nucleotide base pairs. Optionally, the primer pair flanks a region including positions encoding a thymine at a position corresponding to position 17,922 according to SEQ ID NO:2, a uracil at a position corresponding to position 1,185 according to SEQ ID NO:6, a uracil at a position corresponding to position 1,260 according to SEQ ID NO:7, a uracil at a position corresponding to position 1,056 according to SEQ ID NO:8, a thymine at a position corresponding to position 1,185 according to SEQ ID NO:12, a thymine at a position corresponding to position 1,260 according to SEQ ID NO:13, or a thymine at a position corresponding to position 1,056 according to SEQ ID NO:14, and at least 1, 2, 3, 4, 5, 6, 7, 8, 9, 10, or more nucleotides on each side of positions encoding a thymine at a position corresponding to position 17,922 according to SEQ ID NO:2, a uracil at a position corresponding to position 1,185 according to SEQ ID NO:6, a uracil at a position corresponding to position 1,260 according to SEQ ID NO:7, a uracil at a position corresponding to position 1,056 according to SEQ ID NO:8, a thymine at a position corresponding to position 1,185 according to SEQ ID NO:12, a thymine at a position corresponding to position 1,260 according to SEQ ID NO:13, or a thymine at a position corresponding to position 1,056 according to SEQ ID NO:14. Similar amplicons can be generated from the mRNA and/or cDNA sequences. PCR primer pairs can be derived from a known sequence, for example, by using computer programs intended for that purpose, such as the PCR primer analysis tool in Vector NTI version 10 (Informax Inc., Bethesda Md.); PrimerSelect (DNASTAR Inc., Madison, Wis.); and Primer3 (Version 0.4.0.COPYRGT., 1991, Whitehead Institute for Biomedical Research, Cambridge, Mass.). Additionally, the sequence can be visually scanned and primers manually identified using known guidelines.

A variety of techniques including, for example, nucleic acid sequencing, nucleic acid hybridization, and nucleic acid amplification can be used. Illustrative examples of nucleic acid sequencing techniques include, but are not limited to, chain terminator (Sanger) sequencing and dye terminator sequencing.

Other methods involve nucleic acid hybridization methods other than sequencing, including using labeled primers or probes directed against purified DNA, amplified DNA, and fixed cell preparations (fluorescence in situ hybridization (FISH)). In some methods, a target nucleic acid molecule may be amplified prior to or simultaneous with detection. Illustrative examples of nucleic acid amplification techniques include, but are not limited to, polymerase chain reaction (PCR), ligase chain reaction (LCR), strand displacement amplification (SDA), and nucleic acid sequence based amplification (NASBA). Other methods include, but are not limited to, ligase chain reaction, strand displacement amplification, and thermophilic SDA (tSDA).

In hybridization techniques, stringent conditions can be employed such that a probe or primer will specifically hybridize to its target. In some embodiments, a polynucleotide primer or probe under stringent conditions will hybridize to its target sequence to a detectably greater degree than to other non-target sequences, such as, at least 2-fold, at least 3-fold, at least 4-fold, or more over background, including over 10-fold over background. In some embodiments, a polynucleotide primer or probe under stringent conditions will hybridize to its target nucleotide sequence to a detectably greater degree than to other nucleotide sequences by at least 2-fold. In some embodiments, a polynucleotide primer or probe under stringent conditions will hybridize to its target nucleotide sequence to a detectably greater degree than to other nucleotide sequences by at least 3-fold. In some embodiments, a polynucleotide primer or probe under stringent conditions will hybridize to its target nucleotide sequence to a detectably greater degree than to other nucleotide sequences by at least 4-fold. In some embodiments, a polynucleotide primer or probe under stringent conditions will hybridize to its target nucleotide sequence to a detectably greater degree than to other nucleotide sequences by over 10-fold over background. Stringent conditions are sequence-dependent and will be different in different circumstances.

Appropriate stringency conditions which promote DNA hybridization, for example, 6× sodium chloride/sodium citrate (SSC) at about 45° C., followed by a wash of 2×SSC at 50° C., are known or can be found in Current Protocols in Molecular Biology, John Wiley & Sons, N.Y. (1989), 6.3.1-6.3.6. Typically, stringent conditions for hybridization and detection will be those in which the salt concentration is less than about 1.5 M $Na^+$ ion, typically about 0.01 to 1.0 M $Na^+$ ion concentration (or other salts) at pH 7.0 to 8.3 and the temperature is at least about 30° C. for short probes (such as, for example, 10 to 50 nucleotides) and at least about 60° C. for longer probes (such as, for example, greater than 50 nucleotides). Stringent conditions may also be achieved with the addition of destabilizing agents such as formamide. Optionally, wash buffers may comprise about 0.1% to about 1% SDS. Duration of hybridization is generally less than about 24 hours, usually about 4 to about 12 hours. The duration of the wash time will be at least a length of time sufficient to reach equilibrium.

The present disclosure also provides methods of detecting the presence of a human SREBF1 predicted loss-of-function variant polypeptide comprising performing an assay on a sample obtained from a human subject to determine whether an SREBF1 polypeptide in the subject contains one or more variations that causes the polypeptide to have a loss-of-function (partial or complete). In some embodiments, the methods detect the presence of a human SREBF1 predicted loss-of-function variant polypeptide, such as, for example, the SREBF1 Arg334Cys variant polypeptide, and comprise performing an assay on a sample obtained from a human subject to determine whether an SREBF1 polypeptide in the sample comprises a cysteine at a position corresponding to position 334 according to SEQ ID NO:18. In some embodiments, the detecting step comprises sequencing at least a portion of the polypeptide that comprises a position corresponding to position 334 according to SEQ ID NO:15 or SEQ ID NO:18. In some embodiments, the detecting step comprises sequencing the entire polypeptide. In some embodiments, the detecting step comprises an immunoassay for detecting the presence of a polypeptide that comprises a position corresponding to position 334 according to SEQ ID NO:15 or SEQ ID NO:18.

In some embodiments, the methods detect the presence of a human SREBF1 predicted loss-of-function variant polypeptide, such as, for example, the SREBF1 Arg364Cys variant polypeptide, and comprise performing an assay on a sample obtained from a human subject to determine whether an SREBF1 polypeptide in the sample comprises a cysteine at a position corresponding to position 364 according to SEQ ID NO:19. In some embodiments, the detecting step comprises sequencing at least a portion of the polypeptide that comprises a position corresponding to position 364 according to SEQ ID NO:16 or SEQ ID NO:19. In some embodiments, the detecting step comprises sequencing the entire polypeptide. In some embodiments, the detecting step comprises an immunoassay for detecting the presence of a polypeptide that comprises a position corresponding to position 364 according to SEQ ID NO:16 or SEQ ID NO:19.

In some embodiments, the methods detect the presence of a human SREBF1 predicted loss-of-function variant polypeptide, such as, for example, the SREBF1 Arg310Cys variant polypeptide, and comprise performing an assay on a sample obtained from a human subject to determine whether an SREBF1 polypeptide in the sample comprises a cysteine at a position corresponding to position 310 according to SEQ ID NO:20. In some embodiments, the detecting step comprises sequencing at least a portion of the polypeptide that comprises a position corresponding to position 310 according to SEQ ID NO:17 or SEQ ID NO:20. In some embodiments, the detecting step comprises sequencing the entire polypeptide. In some embodiments, the detecting step comprises an immunoassay for detecting the presence of a polypeptide that comprises a position corresponding to position 310 according to SEQ ID NO:17 or SEQ ID NO:20.

The present disclosure also provides isolated nucleic acid molecules that hybridize to SREBF1 predicted loss-of-function variant genomic nucleic acid molecules (such as SEQ ID NO:2), SREBF1 predicted loss-of-function variant mRNA molecules (such as SEQ ID NO:6, SEQ ID NO:7, and SEQ ID NO:8), and/or SREBF1 predicted loss-of-function variant cDNA molecules (such as SEQ ID NO:12, SEQ ID NO:13, and SEQ ID NO:14). In some embodiments, the isolated nucleic acid molecules hybridize to the portion of the SREBF1 nucleic acid molecule that includes a position corresponding to position 17,922 according to SEQ ID NO:2, and include a position corresponding to position 1,185 according to SEQ ID NO:6 or SEQ ID NO:12, include a position corresponding to position 1,260 according to SEQ ID NO:7 or SEQ ID NO:13, or include a position corresponding to position 1,056 according to SEQ ID NO:8 or SEQ ID NO:14.

In some embodiments, such isolated nucleic acid molecules comprise or consist of at least about 5, at least about 8, at least about 10, at least about 11, at least about 12, at least about 13, at least about 14, at least about 15, at least about 16, at least about 17, at least about 18, at least about 19, at least about 20, at least about 21, at least about 22, at least about 23, at least about 24, at least about 25, at least about 30, at least about 35, at least about 40, at least about 45, at least about 50, at least about 55, at least about 60, at least about 65, at least about 70, at least about 75, at least about 80, at least about 85, at least about 90, at least about 95, at least about 100, at least about 200, at least about 300, at least about 400, at least about 500, at least about 600, at least about 700, at least about 800, at least about 900, at least about 1000, at least about 2000, at least about 3000, at least about 4000, at least about 5000, at least about 6000, at least about 7000, at least about 8000, at least about 9000, at least about 10000, at least about 11000, at least about 12000, at least about 13000, at least about 14000, at least about 15000, at least about 16000, at least about 17000, at least about 18000, at least about 19000, or at least about 20000 nucleotides. In some embodiments, such isolated nucleic acid molecules comprise or consist of at least about 5, at least about 8, at least about 10, at least about 11, at least about 12, at least about 13, at least about 14, at least about 15, at least about 16, at least about 17, at least about 18, at least about 19, at least about 20, at least about 21, at least about 22, at least about 23, at least about 24, or at least about 25 nucleotides. In preferred embodiments, the isolated nucleic acid molecules comprise or consist of at least about 18 nucleotides. In some embodiments, the isolated nucleic acid molecules comprise or consists of at least about 15 nucleotides. In some embodiments, the isolated nucleic acid molecules comprise or consist of from about 10 to about 35, from about 10 to about 30, from about 10 to about 25, from about 12 to about 30, from about 12 to about 28, from about 12 to about 24, from about 15 to about 30, from about 15 to about 25, from about 18 to about 30, from about 18 to about 25, from about 18 to about 24, or from about 18 to about 22 nucleotides. In preferred embodiments, the isolated nucleic acid molecules comprise or consist of from about 18 to about 30 nucleotides. In some embodiments, the isolated nucleic acid molecules comprise or consist of at least about 15 nucleotides to at least about 35 nucleotides.

In some embodiments, such isolated nucleic acid molecules hybridize to SREBF1 predicted loss-of-function variant genomic nucleic acid molecules (such as SEQ ID NO:2), SREBF1 predicted loss-of-function variant mRNA molecules (such as SEQ ID NO:6, SEQ ID NO:7, and SEQ ID NO:8), and/or SREBF1 predicted loss-of-function variant cDNA molecules (such as SEQ ID NO:12, SEQ ID NO:13, and SEQ ID NO:14) under stringent conditions. Such nucleic acid molecules can be used, for example, as probes, primers, alteration-specific probes, or alteration-specific primers as described or exemplified herein, and include, without limitation primers, probes, antisense RNAs, shRNAs, and siRNAs, each of which is described in more detail elsewhere herein, and can be used in any of the methods described herein.

In some embodiments, the isolated nucleic acid molecules hybridize to at least about 15 contiguous nucleotides of a nucleic acid molecule that is at least about 70%, at least about 75%, at least about 80%, at least about 85%, at least about 90%, at least about 95%, at least about 96%, at least about 97%, at least about 98%, at least about 99%, or 100% identical to SREBF1 predicted loss-of-function variant genomic nucleic acid molecules (such as SEQ ID NO:2), SREBF1 predicted loss-of-function variant mRNA molecules (such as SEQ ID NO:6, SEQ ID NO:7, and SEQ ID NO:8), and/or SREBF1 predicted loss-of-function variant cDNA molecules (such as SEQ ID NO:12, SEQ ID NO:13, and SEQ ID NO:14). In some embodiments, the isolated nucleic acid molecules comprise or consist of from about 15 to about 100 nucleotides, or from about 15 to about 35 nucleotides. In some embodiments, the isolated nucleic acid molecules comprise or consist of from about 15 to about 100 nucleotides. In some embodiments, the isolated nucleic acid molecules comprise or consist of from about 15 to about 35 nucleotides.

In some embodiments, the isolated alteration-specific probes or alteration-specific primers comprise at least about 15 nucleotides, wherein the alteration-specific probe or alteration-specific primer comprises a nucleotide sequence which is complementary to a portion of a nucleotide sequence encoding a human SREBF1 polypeptide, wherein the portion comprises a position corresponding to: position 17,922 according to SEQ ID NO:2, or the complement thereof; position 1,185 according to SEQ ID NO:6, or the complement thereof; position 1,260 according to SEQ ID NO:7, or the complement thereof; position 1,056 according to SEQ ID NO:8, or the complement thereof; position 1,185 according to SEQ ID NO:12, or the complement thereof; position 1,260 according to SEQ ID NO:13, or the complement thereof; or position 1,056 according to SEQ ID NO:14, or the complement thereof.

In some embodiments, the alteration-specific probe or alteration-specific primer comprises a nucleotide sequence which is complementary to a portion of a nucleotide sequence comprising a position corresponding to position 17,922 according to SEQ ID NO:2, or the complement thereof. In some embodiments, the alteration-specific probe or alteration-specific primer comprises a nucleotide sequence which is complementary to a portion of a nucleotide sequence comprising positions corresponding to positions 17,922 to 17,924 according to SEQ ID NO:2, or the complement thereof.

In some embodiments, the alteration-specific probe or alteration-specific primer comprises a nucleotide sequence which is complementary to a portion of a nucleotide sequence comprising a position corresponding to position 1,185 according to SEQ ID NO:6, or the complement thereof. In some embodiments, the alteration-specific probe or alteration-specific primer comprises a nucleotide sequence which is complementary to a portion of a nucleotide sequence comprising positions corresponding to positions 1,185 to 1,187 according to SEQ ID NO:6, or the complement thereof.

In some embodiments, the alteration-specific probe or alteration-specific primer comprises a nucleotide sequence which is complementary to a portion of a nucleotide sequence comprising a position corresponding to position 1,260 according to SEQ ID NO:7, or the complement thereof. In some embodiments, the alteration-specific probe or alteration-specific primer comprises a nucleotide sequence which is complementary to a portion of a nucleotide sequence comprising positions corresponding to positions 1,260 to 1,262 according to SEQ ID NO:7, or the complement thereof.

In some embodiments, the alteration-specific probe or alteration-specific primer comprises a nucleotide sequence which is complementary to a portion of a nucleotide sequence comprising a position corresponding to position 1,056 according to SEQ ID NO:8, or the complement thereof. In some embodiments, the alteration-specific probe or alteration-specific primer comprises a nucleotide sequence which is complementary to a portion of a nucleotide sequence comprising positions corresponding to positions 1,056 to 1,058 according to SEQ ID NO:8, or the complement thereof.

In some embodiments, the alteration-specific probe or alteration-specific primer comprises a nucleotide sequence which is complementary to a portion of a nucleotide sequence comprising a position corresponding to position 1,185 according to SEQ ID NO:12, or the complement thereof. In some embodiments, the alteration-specific probe or alteration-specific primer comprises a nucleotide sequence which is complementary to a portion of a nucleotide sequence comprising positions corresponding to positions 1,185 to 1,187 according to SEQ ID NO:12, or the complement thereof.

In some embodiments, the alteration-specific probe or alteration-specific primer comprises a nucleotide sequence which is complementary to a portion of a nucleotide sequence comprising a position corresponding to position 1,260 according to SEQ ID NO:13, or the complement thereof. In some embodiments, the alteration-specific probe or alteration-specific primer comprises a nucleotide sequence which is complementary to a portion of a nucleotide sequence comprising positions corresponding to positions 1,260 to 1,262 according to SEQ ID NO:13, or the complement thereof.

In some embodiments, the alteration-specific probe or alteration-specific primer comprises a nucleotide sequence which is complementary to a portion of a nucleotide sequence comprising a position corresponding to position 1,056 according to SEQ ID NO:14, or the complement thereof. In some embodiments, the alteration-specific probe or alteration-specific primer comprises a nucleotide sequence which is complementary to a portion of a nucleotide sequence comprising positions corresponding to positions 1,056 to 1,058 according to SEQ ID NO:14, or the complement thereof.

In some embodiments, the alteration-specific probes and alteration-specific primers comprise DNA. In some embodiments, the alteration-specific probes and alteration-specific primers comprise RNA.

In some embodiments, the probes and primers described herein (including alteration-specific probes and alteration-specific primers) have a nucleotide sequence that specifically hybridizes to any of the nucleic acid molecules disclosed herein, or the complement thereof. In some embodiments, the probes and primers specifically hybridize to any of the nucleic acid molecules disclosed herein under stringent conditions.

In some embodiments, the primers, including alteration-specific primers, can be used in second generation sequencing or high throughput sequencing. In some instances, the primers, including alteration-specific primers, can be modified. In particular, the primers can comprise various modifications that are used at different steps of, for example, Massive Parallel Signature Sequencing (MPSS), Polony sequencing, and 454 Pyrosequencing. Modified primers can be used at several steps of the process, including biotinylated primers in the cloning step and fluorescently labeled primers used at the bead loading step and detection step. Polony sequencing is generally performed using a paired-end tags library wherein each molecule of DNA template is about 135 bp in length. Biotinylated primers are used at the bead loading step and emulsion PCR. Fluorescently labeled degenerate nonamer oligonucleotides are used at the detection step. An adaptor can contain a 5'-biotin tag for immobilization of the DNA library onto streptavidin-coated beads.

The probes and primers described herein can be used to detect the C17,922T variation within the SREBF1 variant genomic nucleic acid molecule (such as SEQ ID NO:2), the C1,185U variation within the SREBF1 variant mRNA molecule (such as SEQ ID NO:6), the C1,260U variation within the SREBF1 variant mRNA molecule (such as SEQ ID NO:7), the C1,056U variation within the SREBF1 variant mRNA molecule (such as SEQ ID NO:8), the C1,185T variation within the SREBF1 variant cDNA molecule (such as SEQ ID NO:12), the C1,260T variation within the SREBF1 variant cDNA molecule (such as SEQ ID NO:13), or the C1,056T variation within the SREBF1 variant cDNA molecule (such as SEQ ID NO:14). For example, the primers can be used to amplify SREBF1 variant genomic nucleic acid molecules or a fragment thereof comprising the C17,922T variation. The primers can also be used to amplify SREBF1 variant mRNA or a fragment thereof comprising the C1,185U variation, C1,260U variation, and/or C1,056U variation. The primers can also be used to amplify SREBF1 variant cDNA or a fragment thereof comprising the C1,185T variation, C1,260T variation, and/or C1,056T variation.

The present disclosure also provides pairs of primers comprising any of the primers described above. If one of the primers' 3'-ends hybridizes to a cytosine at position 17,922 (rather than thymine) in a particular SREBF1 nucleic acid molecule, then the presence of the amplified fragment would indicate the presence of an SREBF1 reference genomic nucleic acid molecule. Conversely, if one of the primers' 3'-ends hybridizes to a thymine at position 17,922 (rather than cytosine) in a particular SREBF1 nucleic acid molecule, then the presence of the amplified fragment would indicate the presence of the SREBF1 variant genomic nucleic acid molecule. In some embodiments, the nucleotide of the primer complementary to the thymine at a position corresponding to position 17,922 in SEQ ID NO:2 can be at the 3' end of the primer.

If one of the primers' 3'-ends hybridizes to a cytosine at position 1,185 (rather than uracil) in a particular SREBF1 mRNA molecule, then the presence of the amplified fragment would indicate the presence of an SREBF1 reference mRNA molecule. Conversely, if one of the primers' 3'-ends hybridizes to a uracil at position 1,185 (rather than cytosine) in a particular SREBF1 mRNA molecule, then the presence of the amplified fragment would indicate the presence of the SREBF1 variant mRNA molecule. In some embodiments, the nucleotide of the primer complementary to the uracil at a position corresponding to position 1,185 in SEQ ID NO:6 can be at the 3' end of the primer. In addition, if one of the primers' 3'-ends hybridizes to a cytosine at position 1,260 (rather than uracil) in a particular SREBF1 mRNA molecule, then the presence of the amplified fragment would indicate the presence of an SREBF1 reference mRNA molecule. Conversely, if one of the primers' 3'-ends hybridizes to a uracil at position 1,260 (rather than cytosine) in a particular SREBF1 mRNA molecule, then the presence of the amplified fragment would indicate the presence of the SREBF1 variant mRNA molecule. In some embodiments, the nucleotide of the primer complementary to the uracil at a position corresponding to position 1,260 in SEQ ID NO:7 can be at the 3' end of the primer. In addition, if one of the primers' 3'-ends hybridizes to a cytosine at position 1,056 (rather than uracil) in a particular SREBF1 mRNA molecule, then the presence of the amplified fragment would indicate the presence of an SREBF1 reference mRNA molecule. Conversely, if one of the primers' 3'-ends hybridizes to a uracil at position 1,056 (rather than cytosine) in a particular SREBF1 mRNA molecule, then the presence of the amplified fragment would indicate the presence of the SREBF1 variant mRNA molecule. In some embodiments, the nucleotide of the primer complementary to the uracil at a position corresponding to position 1,056 in SEQ ID NO:8 can be at the 3' end of the primer.

If one of the primers' 3'-ends hybridizes to a cytosine at position 1,185 (rather than thymine) in a particular SREBF1 cDNA molecule, then the presence of the amplified fragment would indicate the presence of an SREBF1 reference cDNA molecule. Conversely, if one of the primers' 3'-ends hybridizes to a thymine at position 1,185 (rather than cytsone) in a particular SREBF1 cDNA molecule, then the presence of the amplified fragment would indicate the presence of the SREBF1 variant cDNA molecule. In some embodiments, the nucleotide of the primer complementary to the thymine at a position corresponding to position 1,185 in SEQ ID NO:12 can be at the 3' end of the primer. In addition, if one of the primers' 3'-ends hybridizes to a cytosine at position 1,260 (rather than thymine) in a particular SREBF1 cDNA molecule, then the presence of the amplified fragment would indicate the presence of an SREBF1 reference cDNA molecule. Conversely, if one of the primers' 3'-ends hybridizes to a thymine at position 1,260 (rather than cytsone) in a particular SREBF1 cDNA molecule, then the presence of the amplified fragment would indicate the presence of the SREBF1 variant cDNA molecule. In some embodiments, the nucleotide of the primer complementary to the thymine at a position corresponding to position 1,260 in SEQ ID NO:13 can be at the 3' end of the primer. In addition, if one of the primers' 3'-ends hybridizes to a cytosine at position 1,056 (rather than thymine) in a particular SREBF1 cDNA molecule, then the presence of the amplified fragment would indicate the presence of an SREBF1 reference cDNA molecule. Conversely, if one of the primers' 3'-ends hybridizes to a thymine at position 1,056 (rather than cytsone) in a particular SREBF1 cDNA molecule, then the presence of the amplified fragment would indicate the presence of the SREBF1 variant cDNA molecule. In some embodiments, the nucleotide of the primer complementary to the thymine at a position corresponding to position 1,056 in SEQ ID NO:14 can be at the 3' end of the primer.

In some embodiments, the probes or primers comprise a nucleotide sequence which hybridizes to a portion of an SREBF1 genomic nucleic acid molecule, wherein the portion comprises a thymine at a position corresponding to position 17,922 according to SEQ ID NO:2, or which hybridizes to the complement of this nucleic acid molecule. In some embodiments, the probes or primers comprise a nucleotide sequence which hybridizes to an SREBF1 genomic nucleic acid molecule comprising SEQ ID NO:2 at a portion comprising a thymine at a position corresponding to position 17,922 according to SEQ ID NO:2, or which hybridizes to the complement of this nucleic acid molecule.

In some embodiments, the probes or primers comprise a nucleotide sequence which hybridizes to a portion of an SREBF1 mRNA molecule, wherein the portion comprises a uracil at a position corresponding to position 1,185 according to SEQ ID NO:6, or which hybridizes to the complement of this nucleic acid molecule. In some embodiments, the probes or primers comprise a nucleotide sequence which hybridizes to an SREBF16 mRNA molecule comprising SEQ ID NO:6 at a portion comprising a uracil at a position corresponding to position 1,185 according to SEQ ID NO:6, or which hybridizes to the complement of this nucleic acid molecule.

In some embodiments, the probes or primers comprise a nucleotide sequence which hybridizes to a portion of an SREBF1 mRNA molecule, wherein the portion comprises a uracil at a position corresponding to position 1,260 according to SEQ ID NO:7, or which hybridizes to the complement of this nucleic acid molecule. In some embodiments, the probes or primers comprise a nucleotide sequence which hybridizes to an SREBF16 mRNA molecule comprising SEQ ID NO:7 at a portion comprising a uracil at a position corresponding to position 1,260 according to SEQ ID NO:7, or which hybridizes to the complement of this nucleic acid molecule.

In some embodiments, the probes or primers comprise a nucleotide sequence which hybridizes to a portion of an SREBF1 mRNA molecule, wherein the portion comprises a uracil at a position corresponding to position 1,056 according to SEQ ID NO:8, or which hybridizes to the complement of this nucleic acid molecule. In some embodiments, the probes or primers comprise a nucleotide sequence which hybridizes to an SREBF16 mRNA molecule comprising SEQ ID NO:8 at a portion comprising a uracil at a position corresponding to position 1,056 according to SEQ ID NO:8, or which hybridizes to the complement of this nucleic acid molecule.

In some embodiments, the probes or primers comprise a nucleotide sequence which hybridizes to a portion of an SREBF1 cDNA molecule, wherein the portion comprises a thymine at a position corresponding to position 1,185 according to SEQ ID NO:12, or which hybridizes to the complement of this nucleic acid molecule. In some embodiments, the probes or primers comprise a nucleotide sequence which hybridizes to an SREBF1 cDNA molecule comprising SEQ ID NO:12 at a portion comprising a thymine at a position corresponding to position 1,185 according to SEQ ID NO:12, or which hybridizes to the complement of this nucleic acid molecule.

In some embodiments, the probes or primers comprise a nucleotide sequence which hybridizes to a portion of an SREBF1 cDNA molecule, wherein the portion comprises a thymine at a position corresponding to position 1,260 according to SEQ ID NO:13, or which hybridizes to the complement of this nucleic acid molecule. In some embodiments, the probes or primers comprise a nucleotide sequence which hybridizes to an SREBF1 cDNA molecule comprising SEQ ID NO:13 at a portion comprising a thymine at a position corresponding to position 1,260 according to SEQ ID NO:13, or which hybridizes to the complement of this nucleic acid molecule.

In some embodiments, the probes or primers comprise a nucleotide sequence which hybridizes to a portion of an SREBF1 cDNA molecule, wherein the portion comprises a thymine at a position corresponding to position 1,056 according to SEQ ID NO:14, or which hybridizes to the complement of this nucleic acid molecule. In some embodiments, the probes or primers comprise a nucleotide sequence which hybridizes to an SREBF1 cDNA molecule comprising SEQ ID NO:14 at a portion comprising a thymine at a position corresponding to position 1,056 according to SEQ ID NO:14, or which hybridizes to the complement of this nucleic acid molecule.

In the context of the disclosure "specifically hybridizes" means that the probe or primer (such as, for example, the alteration-specific probe or alteration-specific primer) does not hybridize to a nucleic acid sequence encoding an SREBF1 reference genomic nucleic acid molecule, an SREBF1 reference mRNA molecule, and/or an SREBF1 reference cDNA molecule.

In some embodiments, the probes (such as, for example, an alteration-specific probe) comprise a label. In some embodiments, the label is a fluorescent label, a radiolabel, or biotin.

The present disclosure also provides supports comprising a substrate to which any one or more of the probes disclosed herein is attached. Solid supports are solid-state substrates or supports with which molecules, such as any of the probes disclosed herein, can be associated. A form of solid support is an array. Another form of solid support is an array detector. An array detector is a solid support to which multiple different probes have been coupled in an array, grid, or other organized pattern. A form for a solid-state substrate is a microtiter dish, such as a standard 96-well type. In some embodiments, a multiwell glass slide can be employed that normally contains one array per well.

The present disclosure also provides molecular complexes comprising or consisting of any of the SREBF1 nucleic acid molecules (genomic nucleic acid molecules, mRNA molecules, or cDNA molecules), or complement thereof, described herein and any of the alteration-specific primers or alteration-specific probes described herein. In some embodiments, the SREBF1 nucleic acid molecules (genomic nucleic acid molecules, mRNA molecules, or cDNA molecules), or complement thereof, in the molecular complexes are single-stranded. In some embodiments, the SREBF1 nucleic acid molecule is any of the genomic nucleic acid molecules described herein. In some embodiments, the SREBF1 nucleic acid molecule is any of the mRNA molecules described herein. In some embodiments, the SREBF1 nucleic acid molecule is any of the cDNA molecules described herein. In some embodiments, the molecular complex comprises or consists of any of the SREBF1 nucleic acid molecules (genomic nucleic acid molecules, mRNA molecules, or cDNA molecules), or complement thereof, described herein and any of the alteration-specific primers described herein. In some embodiments, the molecular complex comprises or consists of any of the SREBF1 nucleic acid molecules (genomic nucleic acid molecules, mRNA molecules, or cDNA molecules), or complement thereof, described herein and any of the alteration-specific probes described herein.

In some embodiments, the molecular complex comprises or consists of an alteration-specific primer or an alteration-specific probe hybridized to a genomic nucleic acid molecule comprising a nucleotide sequence encoding a human SREBF1 polypeptide, wherein the alteration-specific primer or the alteration-specific probe is hybridized to: a thymine at a position corresponding to position 17,922 according to SEQ ID NO:2, or the complement thereof. In some embodiments, the molecular complex comprises or consists of an alteration-specific primer or an alteration-specific probe that is hybridized to: a TGC codon at positions corresponding to positions 17,922 to 17,924 according to SEQ ID NO:2. In some embodiments, the molecular complex comprises or consists of a genomic nucleic acid molecule that comprises SEQ ID NO:2.

In some embodiments, the molecular complex comprises or consists of an alteration-specific primer or an alteration-specific probe hybridized to an mRNA molecule comprising a nucleotide sequence encoding a human SREBF1 polypeptide, wherein the alteration-specific primer or the alteration-specific probe is hybridized to: uracil at a position corresponding to position 1,185 according to SEQ ID NO:6, or the complement thereof; a uracil at a position corresponding to position 1,260 according to SEQ ID NO:7, or the complement thereof; or a uracil at a position corresponding to position 1,056 according to SEQ ID NO:8, or the complement thereof. In some embodiments, the molecular complex comprises or consists of an alteration-specific primer or an alteration-specific probe that is hybridized to: a UGC codon at positions corresponding to positions 1,185 to 1,187 according to SEQ ID NO:6, a UGC codon at positions corresponding to positions 1,260 to 1,262 according to SEQ ID NO:6, or a UGC codon at positions corresponding to positions 1,056 to 1,058 according to SEQ ID NO:8. In some embodiments, the molecular complex comprises or consists of an mRNA molecule that comprises SEQ ID NO:6, SEQ ID NO:7, or SEQ ID NO:8.

In some embodiments, the molecular complex comprises or consists of an alteration-specific primer or an alteration-specific probe hybridized to a cDNA molecule comprising a nucleotide sequence encoding a human SREBF1 polypeptide, wherein the alteration-specific primer or the alteration-specific probe is hybridized to: a thymine at a position corresponding to position 1,185 according to SEQ ID NO:12, or the complement thereof; a thymine at a position corresponding to position 1,260 according to SEQ ID NO:13, or the complement thereof; or a thymine at a position corresponding to position 1,056 according to SEQ ID NO:14, or the complement thereof. In some embodiments, the molecular complex comprises or consists of an alteration-specific primer or an alteration-specific probe that is hybridized to: a TGC codon at positions corresponding to positions 1,185 to 1,187 according to SEQ ID NO:12, a TGC codon at positions corresponding to positions 1,260 to 1,262 according to SEQ ID NO:13, or a TGC codon at positions corresponding to positions 1,056 to 1,058 according to SEQ ID NO:14. In some embodiments, the molecular complex comprises or consists of a cDNA molecule that comprises SEQ ID NO:12, SEQ ID NO:13, or SEQ ID NO:14.

In some embodiments, the molecular complex comprises an alteration-specific probe or an alteration-specific primer comprising a label. In some embodiments, the label is a fluorescent label, a radiolabel, or biotin. In some embodiments, the molecular complex further comprises a non-human polymerase.

The present disclosure also provides isolated nucleic acid molecules comprising a nucleotide sequence encoding a human SREBF1 polypeptide, wherein the polypeptide comprises a cysteine at a position corresponding to: position 334 according to SEQ ID NO:18, or the complement thereof; position 364 according to SEQ ID NO:19, or the complement thereof; or position 310 according to SEQ ID NO:20, or the complement thereof.

In some embodiments, the isolated nucleic acid molecule encodes an SREBF1 polypeptide having an amino acid sequence that has at least about 90%, at least about 91%, at least about 92%, at least about 93%, at least about 94%, at least about 95%, at least about 96%, at least about 97%, at least about 98%, or at least about 99% sequence identity to: SEQ ID NO:18, and comprises a cysteine at a position corresponding to position 334 according to SEQ ID NO:18; SEQ ID NO:19, and comprises a cysteine at a position corresponding to position 364 according to SEQ ID NO:19; or SEQ ID NO:20, and comprises a cysteine at a position corresponding to position 310 according to SEQ ID NO:20.

In some embodiments, the nucleic acid molecule encodes an SREBF1 polypeptide comprising SEQ ID NO:18, SEQ ID NO:19, or SEQ ID NO:20. In some embodiments, the nucleic acid molecule encodes an SREBF1 polypeptide consisting of SEQ ID NO:18, SEQ ID NO:19, or SEQ ID NO:20.

The nucleotide sequence of an SREBF1 reference genomic nucleic acid molecule is set forth in SEQ ID NO:1. Referring to SEQ ID NO:1, position 17,922 of the SREBF1 reference genomic nucleic acid molecule is a cytosine. A variant genomic nucleic acid molecule of SREBF1 exists, wherein the cytosine at position 17,922 is replaced with thymine. The nucleotide sequence of this SREBF1 predicted loss-of-function variant genomic nucleic acid molecule is set forth in SEQ ID NO:2.

The present disclosure provides isolated genomic nucleic acid molecules comprising or consisting of a nucleotide sequence encoding a human SREBF1 polypeptide, wherein the nucleotide sequence comprises a thymine at a position corresponding to position 17,922 (C17,922T) according to SEQ ID NO:2, or the complement thereof. In some embodiments, the isolated genomic nucleic acid molecules comprise a nucleotide sequence encoding a human SREBF1 polypeptide, wherein the nucleotide sequence comprises a TGC codon at positions corresponding to positions 17,922 to 17,924 according to SEQ ID NO:2.

In some embodiments, the isolated genomic nucleic acid molecules comprise or consist of a nucleotide sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:2, and comprises a thymine at a position corresponding to position 17,922 according to SEQ ID NO:2, or the complement thereof. Herein, if reference is made to percent sequence identity, the higher percentages of sequence identity are preferred over the lower ones.

In some embodiments, the isolated genomic nucleic acid molecules comprise or consist of a nucleotide sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:2, and comprises a TGC codon at positions corresponding to positions 17,922 to 17,924 according to SEQ ID NO:2, or the complement thereof. Herein, if reference is made to percent sequence identity, the higher percentages of sequence identity are preferred over the lower ones.

In some embodiments, the isolated genomic nucleic acid molecules comprise SEQ ID NO:2. In some embodiments, the isolated genomic nucleic acid molecules consist of SEQ ID NO:2.

In some embodiments, the isolated genomic nucleic acid molecules comprise less than the entire genomic DNA sequence. In some embodiments, the isolated genomic nucleic acid molecules comprise or consist of at least about 15, at least about 20, at least about 25, at least about 30, at least about 35, at least about 40, at least about 45, at least about 50, at least about 60, at least about 70, at least about 80, at least about 90, at least about 100, at least about 200, at least about 300, at least about 400, at least about 500, at least about 600, at least about 700, at least about 800, at least about 900, at least about 1000, at least about 2000, at least about 3000, at least about 4000, at least about 5000, at least about 6000, at least about 7000, at least about 8000, at least about 9000, at least about 10000, at least about 11000, at least about 12000, at least about 13000, at least about 14000, at least about 15000, at least about 16000, at least about 17000, or at least about 18000 contiguous nucleotides of SEQ ID NO:2. In some embodiments, the isolated genomic nucleic acid molecules comprise or consist of at least about 1000 to at least about 2000 contiguous nucleotides of SEQ ID NO:2. In some embodiments, these isolated genomic nucleic acid molecules comprise the thymine at a position corresponding to position 17,922 according to SEQ ID NO:2.

The nucleotide sequences of three SREBF1 reference mRNA molecules are set forth in SEQ ID NO:3, SEQ ID NO:4, and SEQ ID NO:5. Referring to SEQ ID NO:3, position 1,185 of the SREBF1 reference mRNA molecule is a cytosine. Referring to SEQ ID NO:4, position 1,260 of the SREBF1 reference mRNA molecule is a cytosine. Referring to SEQ ID NO:5, position 1,056 of the SREBF1 reference mRNA molecule is a cytosine. Three variant mRNA molecules of SREBF1 exist, wherein the cytosine is replaced with thymine. Referring to SEQ ID NO:6, position 1,185 of the variant SREBF1 mRNA molecule is a thymine. Referring to SEQ ID NO:7, position 1,260 of the variant SREBF1 mRNA molecule is a thymine. Referring to SEQ ID NO:8, position 1,056 of the variant SREBF1 mRNA molecule is a thymine.

The present disclosure provides isolated mRNA molecules comprising or consisting of a nucleotide sequence encoding a human SREBF1 polypeptide, wherein the nucleotide sequence comprises: a uracil at a position corresponding to position 1,185 according to SEQ ID NO:6, or the complement thereof; a uracil at a position corresponding to position 1,260 according to SEQ ID NO:7, or the complement thereof; or a uracil at a position corresponding to position 1,056 according to SEQ ID NO:8, or the complement thereof.

In some embodiments, the isolated mRNA molecules comprise or consist of a nucleotide sequence encoding a human SREBF1 polypeptide, wherein the nucleotide sequence comprises: a UGC codon at positions corresponding to positions 1,185 to 1,187 according to SEQ ID NO:6; a UGC codon at positions corresponding to positions 1,260 to 1,262 according to SEQ ID NO:7; or a UGC codon at positions corresponding to positions 1,056 to 1,058 according to SEQ ID NO:8.

In some embodiments, the isolated mRNA molecules comprise or consist of a nucleotide sequence that has at least about 90%, at least about 91%, at least about 92%, at least about 93%, at least about 94%, at least about 95%, at least about 96%, at least about 97%, at least about 98%, or at least about 99% sequence identity to: SEQ ID NO:6, and comprise a uracil at a position corresponding to position 1,185 according to SEQ ID NO:6, or the complement thereof; SEQ ID NO:7, and comprise a uracil at a position corresponding to position 1,260 according to SEQ ID NO:7, or the complement thereof; SEQ ID NO:8, and comprise a uracil at a position corresponding to position 1,056 according to SEQ ID NO:8, or the complement thereof. Herein, if reference is made to percent sequence identity, the higher percentages of sequence identity are preferred over the lower ones.

In some embodiments, the isolated mRNA molecules comprise or consist of a nucleotide sequence that has at least about 90%, at least about 91%, at least about 92%, at least about 93%, at least about 94%, at least about 95%, at least about 96%, at least about 97%, at least about 98%, or at least about 99% sequence identity to: SEQ ID NO:6, and comprise a UGC codon at positions corresponding to positions 1,185 to 1,187 according to SEQ ID NO:6, or the complement thereof; SEQ ID NO:7, and comprise a UGC codon at positions corresponding to positions 1,260 to 1,262 according to SEQ ID NO:7, or the complement thereof; or SEQ ID NO:8, and comprise a UGC codon at positions corresponding to positions 1,056 to 1,058 according to SEQ ID NO:8, or the complement thereof. Herein, if reference is made to percent sequence identity, the higher percentages of sequence identity are preferred over the lower ones.

In some embodiments, the isolated mRNA molecules comprise SEQ ID NO:6, SEQ ID NO:7, or SEQ ID NO:8. In some embodiments, the isolated mRNA molecules consist of SEQ ID NO:6, SEQ ID NO:7, or SEQ ID NO:8. In some embodiments, the isolated mRNA molecules consist of SEQ ID NO:6.

The nucleotide sequences of three SREBF1 reference cDNA molecules are set forth in SEQ ID NO:9, SEQ ID NO:10, and SEQ ID NO:11. Referring to SEQ ID NO:9, position 1,185 of the SREBF1 reference cDNA molecule is a cytosine. Referring to SEQ ID NO:10, position 1,260 of the SREBF1 reference cDNA molecule is a cytosine. Referring to SEQ ID NO:11, position 1,056 of the SREBF1 reference cDNA molecule is a cytosine. Three variant cDNA molecules of SREBF1 exist, wherein the cytosine is replaced with thymine. Referring to SEQ ID NO:12, position 1,185 of the variant SREBF1 cDNA molecule is a thymine. Referring to SEQ ID NO:13, position 1,260 of the variant SREBF1 cDNA molecule is a thymine. Referring to SEQ ID NO:14, position 1,056 of the variant SREBF1 cDNA molecule is a thymine.

The present disclosure provides isolated cDNA molecules comprising or consisting of a nucleotide sequence encoding a human SREBF1 polypeptide, wherein the nucleotide sequence comprises: a thymine at a position corresponding to position 1,185 according to SEQ ID NO:12, or the complement thereof; a thymine at a position corresponding to position 1,260 according to SEQ ID NO:13, or the complement thereof; or a thymine at a position corresponding to position 1,056 according to SEQ ID NO:14, or the complement thereof.

In some embodiments, the isolated cDNA molecule comprises or consists of a nucleotide sequence encoding a human SREBF1 polypeptide, wherein the nucleotide sequence comprises: a TGC codon at positions corresponding to positions 1,185 to 1,187 according to SEQ ID NO:12; a TGC codon at positions corresponding to positions 1,260 to 1,262 according to SEQ ID NO:13; or a TGC codon at positions corresponding to positions 1,056 to 1,058 according to SEQ ID NO:14.

In some embodiments, the isolated cDNA molecules comprise or consist of a nucleotide sequence that has at least about 90%, at least about 91%, at least about 92%, at least about 93%, at least about 94%, at least about 95%, at least about 96%, at least about 97%, at least about 98%, or at least about 99% sequence identity to: SEQ ID NO:12, and comprise a thymine at a position corresponding to position 1,185 according to SEQ ID NO:12, or the complement thereof; SEQ ID NO:13, and comprise a thymine at a position corresponding to position 1,260 according to SEQ ID NO:13, or the complement thereof; or SEQ ID NO:14, and comprise a thymine at a position corresponding to position 1,056 according to SEQ ID NO:14, or the complement thereof. Herein, if reference is made to percent sequence identity, the higher percentages of sequence identity are preferred over the lower ones.

In some embodiments, the isolated cDNA molecules comprise or consist of a nucleotide sequence that has at least about 90%, at least about 91%, at least about 92%, at least about 93%, at least about 94%, at least about 95%, at least about 96%, at least about 97%, at least about 98%, or at least about 99% sequence identity to: SEQ ID NO:12, and comprise a TGC codon at positions corresponding to positions 1,185 to 1,187 according to SEQ ID NO:12, or the complement thereof; SEQ ID NO:13, and comprise a TGC codon at positions corresponding to positions 1,260 to 1,262 according to SEQ ID NO:13, or the complement thereof; or SEQ ID NO:14, and comprise a TGC codon at positions corresponding to positions 1,056 to 1,058 according to SEQ ID NO:14, or the complement thereof. Herein, if reference is made to percent sequence identity, the higher percentages of sequence identity are preferred over the lower ones.

In some embodiments, the isolated cDNA molecules comprise SEQ ID NO:12, SEQ ID NO:13, or SEQ ID NO:14. In some embodiments, the isolated cDNA molecules consist of SEQ ID NO:12, SEQ ID NO:13, or SEQ ID NO:14.

In some embodiments, the isolated mRNA molecules or cDNA molecules comprise less than the entire mRNA or cDNA sequence. In some embodiments, the isolated cDNA molecules comprise or consist of at least about 5, at least about 8, at least about 10, at least about 12, at least about 15, at least about 20, at least about 25, at least about 30, at least about 35, at least about 40, at least about 45, at least about 50, at least about 60, at least about 70, at least about 80, at least about 90, at least about 100, at least about 200, at least about 300, at least about 400, at least about 500, at least about 600, at least about 700, at least about 800, at least about 900, at least about 1000, at least about 1100, at least about 1200, at least about 1300, at least about 1400, at least about 1500, at least about 1600, at least about 1700, at least about 1800, at least about 1900, at least about 2000, at least about 2100, at least about 2200, at least about 2300, at least about 2400, at least about 2500, at least about 2600, at least about 2700, at least about 2800, at least about 2900, at least about 3000, at least about 3100, at least about 3200, or at least about 3300 contiguous nucleotides of SEQ ID NO:6, SEQ ID NO:7, or SEQ ID NO:8 (for mRNA) or SEQ ID NO:12, SEQ ID NO:13, or SEQ ID NO:14 (for cDNA).

The genomic nucleic acid molecules, mRNA molecule, and cDNA molecules can be from any organism. For example, the genomic nucleic acid molecules, mRNA molecules, and cDNA molecules can be human or an ortholog from another organism, such as a non-human mammal, a rodent, a mouse, or a rat. It is understood that genomic nucleic acid molecules, mRNA molecules, and cDNA sequences within a population can vary due to polymorphisms such as single-nucleotide polymorphisms. The examples provided herein are only exemplary sequences. Other sequences are also possible.

Also provided herein are functional polynucleotides that can interact with the disclosed nucleic acid molecules. Functional polynucleotides are nucleic acid molecules that have a specific function, such as binding a target molecule or catalyzing a specific reaction. Examples of functional polynucleotides include, but are not limited to, antisense molecules, aptamers, ribozymes, triplex forming molecules, and external guide sequences. The functional polynucleotides can act as effectors, inhibitors, modulators, and stimulators of a specific activity possessed by a target molecule, or the functional polynucleotides can possess a de novo activity independent of any other molecules.

The isolated nucleic acid molecules disclosed herein can comprise RNA, DNA, or both RNA and DNA. The isolated nucleic acid molecules can also be linked or fused to a heterologous label. Such labels include, for example, chemiluminescents, metals, tags, enzymes, radiolabels, pigments, dyes, chromogens, spin labels, and fluorescent labels. Labels also include, for example, particles, fluorophores, haptens, enzymes and their calorimetric, fluorogenic and chemiluminescent substrates and other labels.

The disclosed nucleic acid molecules can comprise, for example, nucleotides or non-natural or modified nucleotides, such as nucleotide analogs or nucleotide substitutes. Such nucleotides include a nucleotide that contains a modified base, modified sugar, or modified phosphate group, or that incorporates a non-natural moiety in its structure.

The present disclosure also provides vectors comprising any one or more of the nucleic acid molecules disclosed herein. In some embodiments, the vectors comprise any one or more of the nucleic acid molecules disclosed herein and a heterologous nucleic acid. The vectors can be viral or nonviral vectors capable of transporting a nucleic acid molecule. In some embodiments, the vector is a plasmid or cosmid.

Percent identity (or percent complementarity) between particular stretches of nucleotide sequences within nucleic acid molecules or amino acid sequences within polypeptides can be determined routinely using BLAST programs (basic local alignment search tools) and PowerBLAST programs (Altschul et al., J. Mol. Biol., 1990, 215, 403-410; Zhang and Madden, Genome Res., 1997, 7, 649-656) or by using the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489). Herein, if reference is made to percent sequence identity, the higher percentages of sequence identity are preferred over the lower ones.

The present disclosure also provides compositions comprising any one or more of the isolated nucleic acid molecules, genomic nucleic acid molecules, mRNA molecules, and/or cDNA molecules disclosed herein. In some embodiments, the composition is a pharmaceutical composition. In some embodiments, the compositions comprise a carrier and/or excipient.

The amino acid sequences of three SREBF1 reference polypeptides are set forth in SEQ ID NO:15, SEQ ID NO:16, and SEQ ID NO:17. Referring to SEQ ID NO:15, position 334 of the SREBF1 reference polypeptide is an arginine. Referring to SEQ ID NO:16, position 364 of the SREBF1 reference polypeptide is an arginine. Referring to SEQ ID NO:17, position 310 of the SREBF1 reference polypeptide is an arginine. Three variant SREBF1 polypeptides exist, wherein the arginine is replaced with cysteine. Referring to SEQ ID NO:18, position 334 of the variant SREBF1 polypeptide is a cysteine. Referring to SEQ ID NO:19, position 364 of the variant SREBF1 polypeptide is a cysteine. Referring to SEQ ID NO:20, position 310 of the variant SREBF1 polypeptide is a cysteine.

The present disclosure also provides isolated human SREBF1 polypeptides having an amino acid sequence at least about 90%, at least about 91%, at least about 92%, at least about 93%, at least about 94%, at least about 95%, at least about 96%, at least about 97%, at least about 98%, or at least about 99% identical to: SEQ ID NO:18, wherein the polypeptide comprises a cysteine at a position corresponding to position 334 according to SEQ ID NO:18; SEQ ID NO:19, wherein the polypeptide comprises a cysteine at a position corresponding to position 364 according to SEQ ID NO:19; or SEQ ID NO:20, wherein the polypeptide comprises a cysteine at a position corresponding to position 310 according to SEQ ID NO:20. Herein, if reference is made to percent sequence identity, the higher percentages of sequence identity are preferred over the lower ones.

In some embodiments, the amino acid sequence of the isolated human SREBF1 polypeptide comprises SEQ ID NO:18, SEQ ID NO:19, or SEQ ID NO:20. In some embodiments, the amino acid sequence of the isolated human SREBF1 polypeptide consists of SEQ ID NO:18, SEQ ID NO:19, or SEQ ID NO:20.

In some embodiments, the isolated polypeptides comprise or consist of an amino acid sequence at least about 90%, at least about 91%, at least about 92%, at least about 93%, at least about 94%, at least about 95%, at least about 96%, at least about 97%, at least about 98%, at least about 99%, or 100% identical to at least about 8, at least about 10, at least about 15, at least about 20, at least about 25, at least about 30, at least about 35, at least about 40, at least about 45, at least about 50, at least about 60, at least about 70, at least about 80, at least about 90, at least about 100, at least about 150, at least about 200, at least about 250, at least about 300, at least about 350, at least about 400, at least about 450, at least about 500, at least about 550, at least about 600 at least about 650, at least about 700, at least about 750, at least about 800, at least about 850, at least about 900, at least about 950, at least about 1000, at least about 1050, or at least about 1100 contiguous amino acids of SEQ ID NO:18, SEQ ID NO:19, or SEQ ID NO:20. In some embodiments, the isolated polypeptides also comprise: a cysteine at a position corresponding to position 334 of SEQ ID NO:18; a cysteine at a position corresponding to position 364 of SEQ ID NO:19; or a cysteine at a position corresponding to position 310 of SEQ ID NO:20.

The isolated polypeptides disclosed herein can comprise an amino acid sequence of a naturally occurring SREBF1 polypeptide, or can comprise a non-naturally occurring sequence. In some embodiments, the naturally occurring sequence can differ from the non-naturally occurring sequence due to conservative amino acid substitutions.

In some embodiments, the isolated polypeptides comprise non-natural or modified amino acids or peptide analogs. For example, there are numerous D-amino acids or amino acids which have a different functional substituent than the naturally occurring amino acids.

The SREBF1 reference polypeptides can be used, for example, to screen for compounds that act as antagonists, which can be used to treat subjects who are either SREBF1 reference or heterozygous for an SREBF1 predicted loss-of-function nucleic acid molecule. The variant SREBF1 polypeptides (such as the SREBF1 predicted loss-of-function polypeptides described herein) can be used, for example, to screen for compounds that act as agonists, which can be used to treat subjects who are either SREBF1 reference or heterozygous for an SREBF1 predicted loss-of-function nucleic acid molecule.

The present disclosure also provides nucleic acid molecules encoding any of the polypeptides disclosed herein. This includes all degenerate sequences related to a specific polypeptide sequence. Thus, while each particular nucleic acid sequence may not be written out herein, each and every sequence is in fact disclosed and described herein through the disclosed polypeptide sequences.

The present disclosure also provides compositions comprising any one or more of the nucleic acid molecules and/or any one or more of the polypeptides disclosed herein. In some embodiments, the compositions comprise a carrier.

The present disclosure also provides methods of producing any of the SREBF1 polypeptides or fragments thereof disclosed herein. Such SREBF1 polypeptides or fragments thereof can be produced by any suitable method.

The present disclosure also provides cells comprising any one or more of the nucleic acid molecules and/or any one or more of the polypeptides disclosed herein. The cells can be in vitro, ex vivo, or in vivo. Nucleic acid molecules can be linked to a promoter and other regulatory sequences so they are expressed to produce an encoded protein.

The nucleotide and amino acid sequences listed in the accompanying sequence listing are shown using standard letter abbreviations for nucleotide bases, and three-letter code for amino acids. The nucleotide sequences follow the standard convention of beginning at the 5' end of the sequence and proceeding forward (i.e., from left to right in each line) to the 3' end. Only one strand of each nucleotide sequence is shown, but the complementary strand is understood to be included by any reference to the displayed strand. The amino acid sequence follows the standard convention of beginning at the amino terminus of the sequence and proceeding forward (i.e., from left to right in each line) to the carboxy terminus.

As used herein, the phrase "corresponding to" or grammatical variations thereof when used in the context of the numbering of a particular nucleotide or nucleotide sequence or position refers to the numbering of a specified reference sequence when the particular nucleotide or nucleotide sequence is compared to the reference sequence. In other words, the residue (such as, for example, nucleotide or amino acid) number or residue (such as, for example, nucleotide or amino acid) position of a particular polymer is designated with respect to the reference sequence rather than by the actual numerical position of the residue within the particular nucleotide or nucleotide sequence. For example, a particular nucleotide sequence can be aligned to a reference sequence by introducing gaps to optimize residue matches between the two sequences. In these cases, although the gaps are present, the numbering of the residue in the particular nucleotide or nucleotide sequence is made with respect to the reference sequence to which it has been aligned.

For example, a nucleic acid molecule comprising a nucleotide sequence encoding a human SREBF1 polypeptide, wherein the nucleotide sequence comprises a thymine at a position corresponding to position 17,922 according to SEQ ID NO:2 means that if the nucleotide sequence of the SREBF1 genomic nucleic acid molecule is aligned to the sequence of SEQ ID NO:2, the SREBF1 sequence has a thymine residue at the position that corresponds to position 17,922 of SEQ ID NO:2. The same applies for mRNA molecules comprising a nucleotide sequence encoding a human SREBF1 polypeptide, wherein the nucleotide sequence comprises: a uracil at a position corresponding to position 1,185 according to SEQ ID NO:6; a uracil at a position corresponding to position 1,260 according to SEQ ID NO:7; or a uracil at a position corresponding to position 1,056 according to SEQ ID NO:8, and cDNA molecules comprising a nucleotide sequence encoding a human SREBF1 polypeptide, wherein the nucleotide sequence comprises: a thymine at a position corresponding to position 1,185 according to SEQ ID NO:12; a thymine at a position corresponding to position 1,260 according to SEQ ID NO:13; or a thymine at a position corresponding to position 1,056 according to SEQ ID NO:14. In other words, these phrases refer to a nucleic acid molecule encoding an SREBF1 polypeptide, wherein the genomic nucleic acid molecule has a nucleotide sequence that comprises a thymine residue that is homologous to the thymine residue at position 17,922 of SEQ ID NO:2 (or wherein the mRNA molecule has a nucleotide sequence that comprises a uracil residue that is: homologous to the uracil residue at position 1,185 of SEQ ID NO:6; homologous to the uracil residue at position 1,260 of SEQ ID NO:7; or homologous to the uracil residue at position 1,056 of SEQ ID NO:8, or wherein the cDNA molecule has a nucleotide sequence that comprises a thymine residue that is: homologous to the thymine residue at position 1,185 of SEQ ID NO:12; homologous to the thymine residue at position 1,260 of SEQ ID NO:13; or homologous to the thymine residue at position 1,056 of SEQ ID NO:14). Herein, such a sequence is also referred to as an "SREBF1 sequence with the C17,922T alteration" or "SREBF1 sequence with the C17,922T variation" referring to genomic nucleic acid molecules (or "SREBF1 sequence with the C1,185U alteration" or "SREBF1 sequence with the C1,185U variation" or "SREBF1 sequence with the C1,260U alteration" or "SREBF1 sequence with the C1,260U variation" or "SREBF1 sequence with the C1,056U alteration" or "SREBF1 sequence with the C1,056U variation" referring to mRNA molecules, and "SREBF1 sequence with the C1,185T alteration" or "SREBF1 sequence with the C1,185T variation" or "SREBF1 sequence with the C1,260T alteration" or "SREBF1 sequence with the C1,260T variation" or "SREBF1 sequence with the C1,056T alteration" or "SREBF1 sequence with the C1,056T variation" referring to cDNA molecules).

As described herein, a position within an SREBF1 genomic nucleic acid molecule that corresponds to position 17,922 according to SEQ ID NO:2 can be identified by performing a sequence alignment between the nucleotide sequence of a particular SREBF1 nucleic acid molecule and the nucleotide sequence of SEQ ID NO:2. A variety of computational algorithms exist that can be used for performing a sequence alignment to identify a nucleotide position that corresponds to, for example, position 17,922 in SEQ ID NO:2. For example, by using the NCBI BLAST algorithm (Altschul et al., Nucleic Acids Res., 1997, 25, 3389-3402) or CLUSTALW software (Sievers and Higgins, Methods Mol. Biol., 2014, 1079, 105-116) sequence alignments may be performed. However, sequences can also be aligned manually.

The present disclosure also provides therapeutic agents that treat or inhibit an increased lipid level for use in the treatment of an increased lipid level (or for use in the preparation of a medicament for treating an increased lipid level) in a human subject, wherein the human subject has: i) a genomic nucleic acid molecule having a nucleotide sequence encoding a human SREBF1 polypeptide, wherein the nucleotide sequence comprises a thymine at a position corresponding to position 17,922 according to SEQ ID NO:2, or the complement thereof; ii) an mRNA molecule having a nucleotide sequence encoding a human SREBF1 polypeptide, wherein the nucleotide sequence comprises a uracil at a position corresponding to position 1,185 according to SEQ ID NO:6, or the complement thereof; iii) an mRNA molecule having a nucleotide sequence encoding a human SREBF1 polypeptide, wherein the nucleotide sequence comprises a uracil at a position corresponding to position 1,260 according to SEQ ID NO:7, or the complement thereof; iv) an mRNA molecule having a nucleotide sequence encoding a human SREBF1 polypeptide, wherein the nucleotide sequence comprises a uracil at a position corresponding to position 1,056 according to SEQ ID NO:8, or the complement thereof; v) a cDNA molecule having a nucleotide sequence encoding a human SREBF1 polypeptide, wherein the nucleotide sequence comprises a thymine at a position corresponding to position 1,185 according to SEQ ID NO:12, or the complement thereof; vi) a cDNA molecule having a nucleotide sequence encoding a human SREBF1 polypeptide, wherein the nucleotide sequence comprises a thymine at a position corresponding to position 1,260 according to SEQ ID NO:13, or the complement thereof; vii) a cDNA molecule having a nucleotide sequence encoding a human SREBF1 polypeptide, wherein the nucleotide sequence comprises a thymine at a position corresponding to position 1,056 according to SEQ ID NO:14, or the complement thereof; viii) an SREBF1 polypeptide comprising a cysteine at a position corresponding to position 334 according to SEQ ID NO:18; ix) an SREBF1 polypeptide comprising a cysteine at a position corresponding to position 364 according to SEQ ID NO:19; and/or x) an SREBF1 polypeptide comprising a cysteine at a position corresponding to position 310 according to SEQ ID NO:20. The therapeutic agents that treat or inhibit an increased lipid level can be any of the therapeutic agents that treat or inhibit an increased lipid level described herein.

The present disclosure also provides SREBF1 inhibitors for use in the treatment of an increased lipid level (or for use in the preparation of a medicament for treating an increased lipid level) in a human subject, wherein the human subject has: i) a genomic nucleic acid molecule having a nucleotide sequence encoding a human SREBF1 polypeptide, wherein the nucleotide sequence comprises a thymine at a position corresponding to position 17,922 according to SEQ ID NO:2, or the complement thereof; ii) an mRNA molecule having a nucleotide sequence encoding a human SREBF1 polypeptide, wherein the nucleotide sequence comprises a uracil at a position corresponding to position 1,185 according to SEQ ID NO:6, or the complement thereof; iii) an mRNA molecule having a nucleotide sequence encoding a human SREBF1 polypeptide, wherein the nucleotide sequence comprises a uracil at a position corresponding to position 1,260 according to SEQ ID NO:7, or the complement thereof; iv) an mRNA molecule having a nucleotide sequence encoding a human SREBF1 polypeptide, wherein the nucleotide sequence comprises a uracil at a position corresponding to position 1,056 according to SEQ ID NO:8, or the complement thereof; v) a cDNA molecule having a nucleotide sequence encoding a human SREBF1 polypeptide, wherein the nucleotide sequence comprises a thymine at a position corresponding to position 1,185 according to SEQ ID NO:12, or the complement thereof; vi) a cDNA molecule having a nucleotide sequence encoding a human SREBF1 polypeptide, wherein the nucleotide sequence comprises a thymine at a position corresponding to position 1,260 according to SEQ ID NO:13, or the complement thereof; vii) a cDNA molecule having a nucleotide sequence encoding a human SREBF1 polypeptide, wherein the nucleotide sequence comprises a thymine at a position corresponding to position 1,056 according to SEQ ID NO:14, or the complement thereof; viii) an SREBF1 polypeptide comprising a cysteine at a position corresponding to position 334 according to SEQ ID NO:18; ix) an SREBF1 polypeptide comprising a cysteine at a position corresponding to position 364 according to SEQ ID NO:19; and/or x) an SREBF1 polypeptide comprising a cysteine at a position corresponding to position 310 according to SEQ ID NO:20. The SREBF1 inhibitors can be any of the SREBF1 inhibitors described herein.

All patent documents, websites, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise, if different versions of a publication, website or the like are published at different times, the version most recently published at the effective filing date of the application is meant unless otherwise indicated. Any feature, step, element, embodiment, or aspect of the present disclosure can be used in combination with any other feature, step, element, embodiment, or aspect unless specifically indicated otherwise. Although the present disclosure has been described in some detail by way of illustration and example for purposes of clarity and understanding, it will be apparent that certain changes and modifications may be practiced within the scope of the appended claims.

The following examples are provided to describe the embodiments in greater detail. They are intended to illustrate, not to limit, the claimed embodiments. The following examples provide those of ordinary skill in the art with a disclosure and description of how the compounds, compositions, articles, devices and/or methods described herein are made and evaluated, and are intended to be purely exemplary and are not intended to limit the scope of any claims. Efforts have been made to ensure accuracy with respect to numbers (such as, for example, amounts, temperature, etc.), but some errors and deviations may be accounted for. Unless indicated otherwise, parts are parts by weight, temperature is in ° C. or is at ambient temperature, and pressure is at or near atmospheric.

EXAMPLES

Example 1: A Missense Variant In SREBF1 (SREBP) is Significantly Associated with Decreased LDL-C and Total Cholesterol in the Old Order Amish pLoF polymorphisms and missense variants obtained from the Old Order Amish cohort were analyzed. The results (see, Table 1 and FIG. 1) show significant association of SREBF1 variant with decreased LDL-C and total cholesterol. The variant is present at an allele frequency of 0.032 in the Old Order Amish and is drifted about 2900-fold compared to gnomAD.

TABLE 1

Association of SREBF1 Variant with Decreased LDL-C, non-HDL Cholesterol, and Total Cholesterol

| | Trait | P-Value | Effect | P-Value* | Effect* | Ref-Het-Alt |
|---|---|---|---|---|---|---|
| SREBF1 | LDL-C | 5.85e−6 | −11.31 mg/dL | 1.43e−9 | −12.23 mg/dL | 5554-370-8 |
| 17:17819081:G:A | nonHDL Cholesterol | 2.52e−6 | −12.41 mg/dL | 1.58e−9 | −13.24 mg/dL | 5559-371-8 |
| p.Arg364Cys, p.Arg334Cys | Total Cholesterol | 6.26e−6 | −12.34 mg/dL | 1.62e−8 | −13.20 mg/dL | 5559-371-8 |

*The p-value and effect have been adjusted for APOB p.R3527Q genotype, which is more common in the Old Order Amish. All traits are also adjusted for age, age$^2$, sex, and study.

Example 2: SREBF1 Variants Modulate LDLR Promoter Activity

Figure 2:
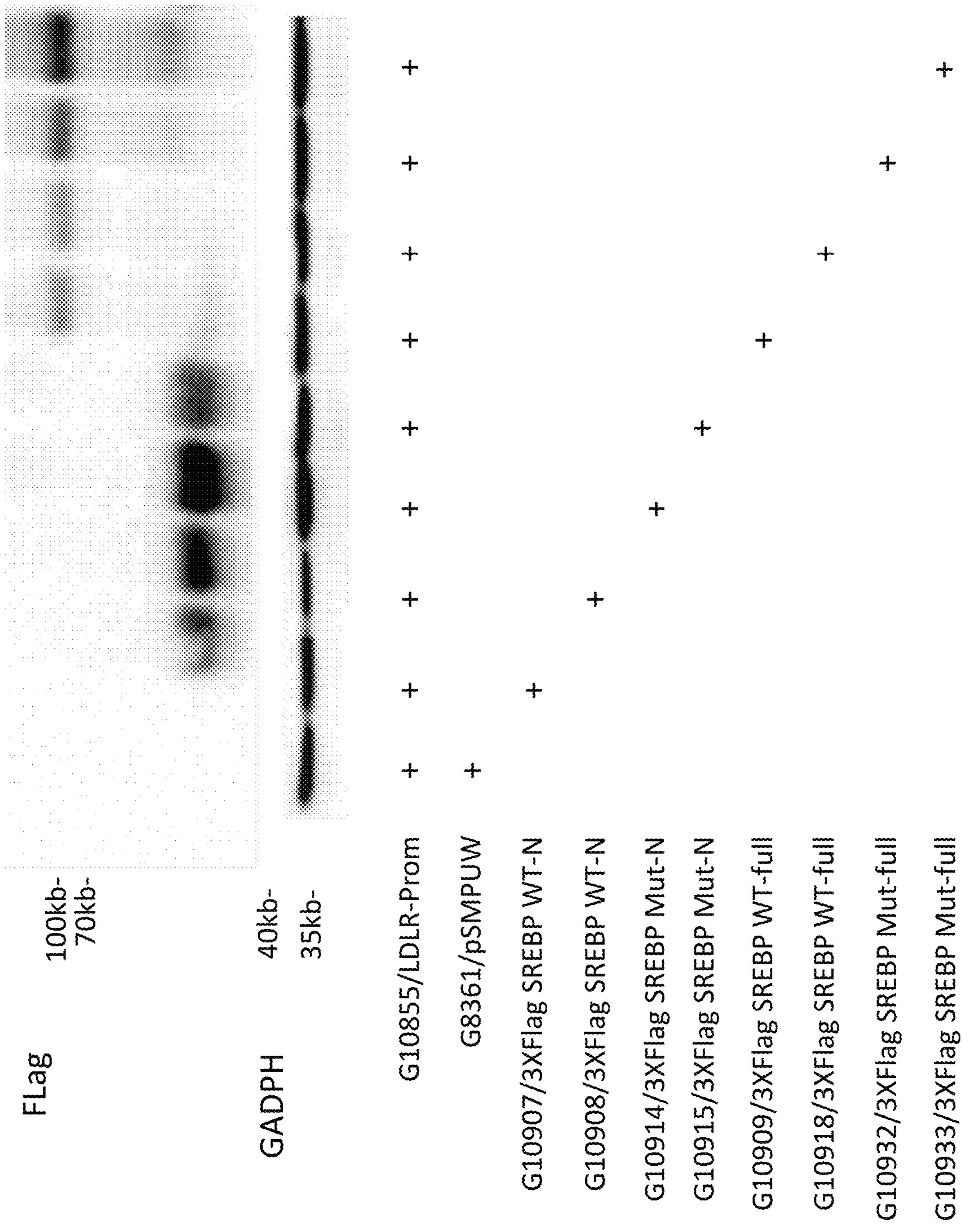
FIG. 2 shows an anti-flag Western blot protein analysis of 3×flag tagged nuclear and full-length SREBP-wt and SREBP-R334C plasmid construct transactivating activities on an LDLR-promoter luciferase reporter.
Figure 3:
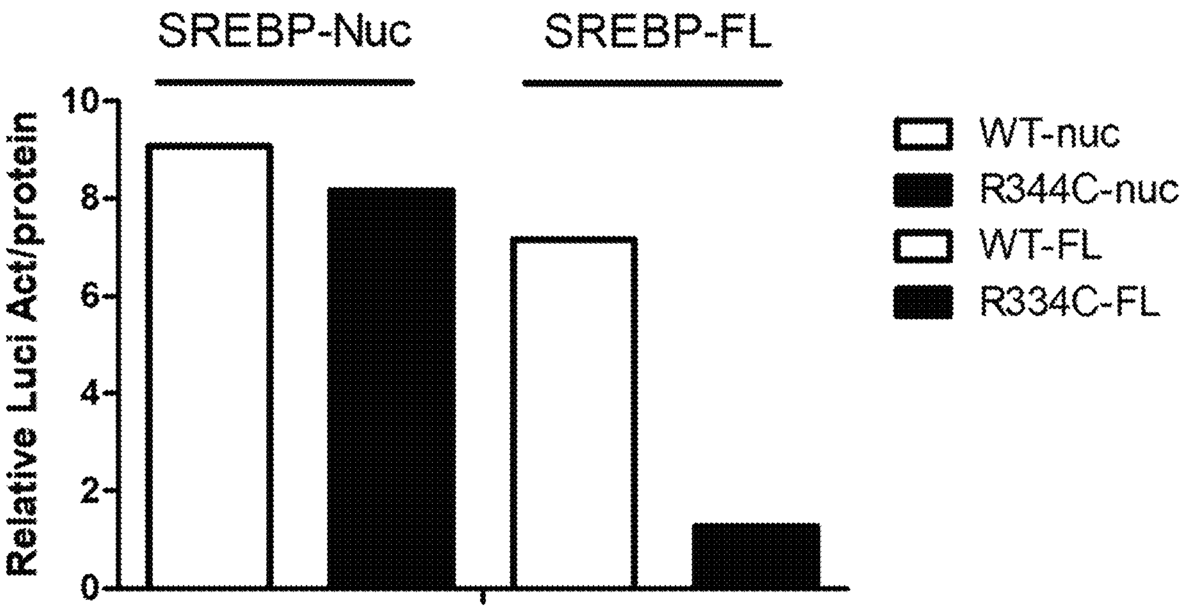
FIG. 3 shows relative activity of luc reporter with SREBP-wt and SREBP-R334C from FIG. 2.

Transient transfections of plasmids containing a pLDLR-luc reporter (G10855) were conducted with 0.4 μg each of SREBF1 WT or Mut SREBF1 (R334C) variant in the nuclear form or full-length form and a control pSMPUW plasmid at constant and titrated dosages in HEK293 cells. The cells were collected 48 hours later for luciferase assay and anti-flag Western blot protein analysis. Luciferase activities were measured as a surrogate of LDLR promoter activity, Western blots (FIG. 2) were performed with anti-flag antibodies to measure flag-tagged SREBP protein expression, and the protein bands were quantified using ImageLab software (FIG. 3).

Figure 4:
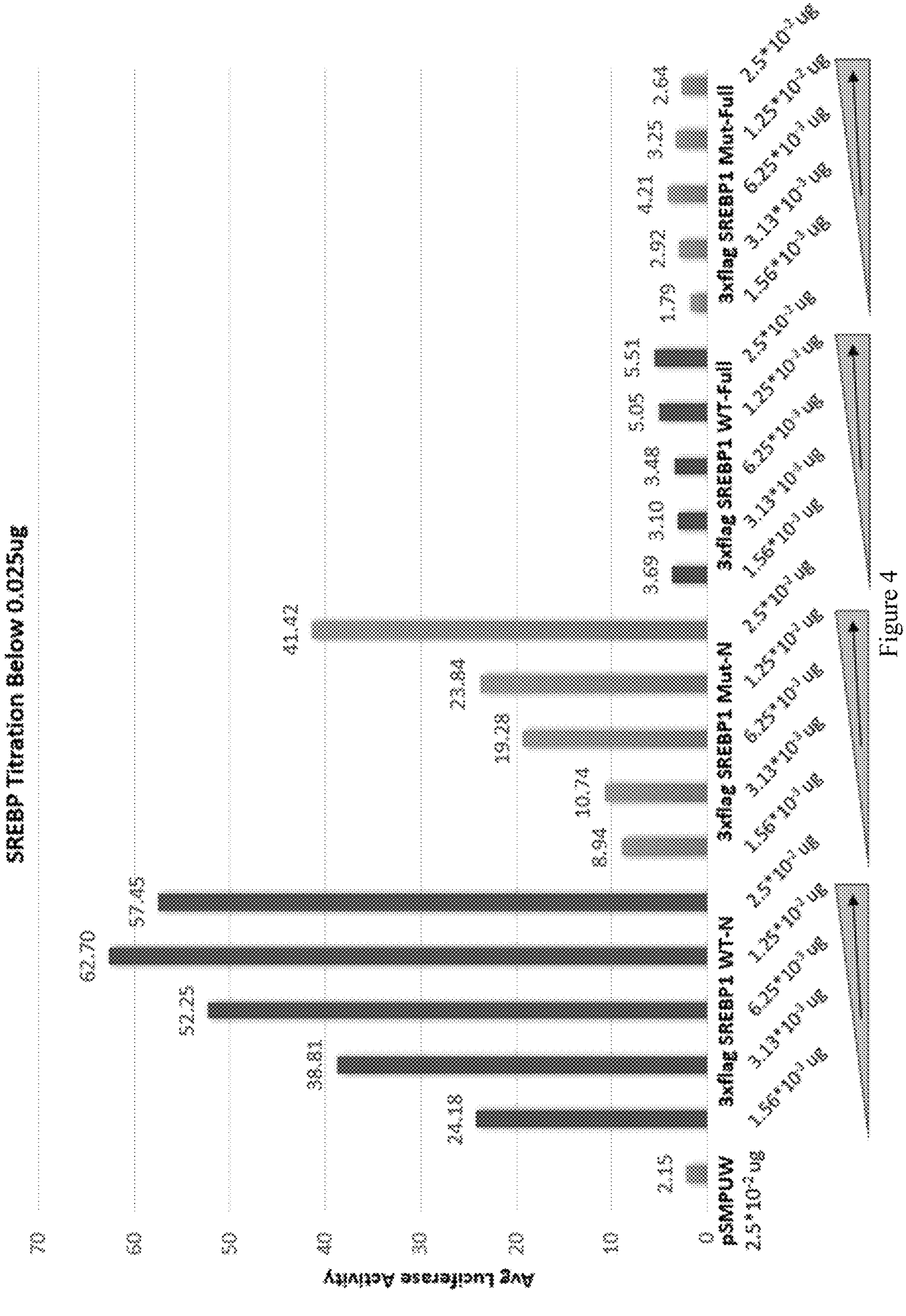
FIG. 4 shows results of an SREBP titration transfection below 0.025 μg.

Results have shown that the full-length and cleaved nuclear and full-length variants of SREBF1 (R334C) have less LDLR promoter trans-activating reporter activity than the wild-type on the LDLR promoter reporter, as indicated by luciferase and ImageLab results (FIG. 4), indicating that the SREBP variant may have less regulatory activities on LDLR and other target genes. The R334C variation falls in the HLH domain of SREBP, which binds to the promoter DNA of target genes.

Various modifications of the described subject matter, in addition to those described herein, will be apparent to those skilled in the art from the foregoing description. Such modifications are also intended to fall within the scope of the appended claims. Each reference (including, but not limited to, journal articles, U.S. and non-U.S. patents, patent application publications, international patent application publications, gene bank accession numbers, and the like) cited in the present application is incorporated herein by reference in its entirety and for all purposes.

What is claimed is:

1. A method of treating a subject having increased total cholesterol and/or increased low density lipoprotein (LDL), the method comprising administering a Sterol Regulatory Element Binding Transcription Factor 1 (SREBF1) inhibitor to the subject, wherein the SREBF1 inhibitor comprises a small interfering RNA (siRNA) that hybridizes to an SREBF1 mRNA, and wherein the subject is either SREBF1 reference or heterozygous for an SREBF1 variant nucleic acid molecule, wherein the SREBF1 variant nucleic acid molecule comprises:

i) a genomic nucleic acid molecule having a nucleotide sequence comprising a thymine at a position corresponding to position 17,922 according to SEQ ID NO:2, or the complement thereof, ii) an mRNA molecule having a nucleotide sequence comprising a uracil at a position corresponding to position 1,185 according to SEQ ID NO:6, or the complement thereof, iii) an mRNA molecule having a nucleotide sequence comprising a uracil at a position corresponding to position 1,260 according to SEQ ID NO:7, or the complement thereof, and/or iv) an mRNA molecule having a nucleotide sequence comprising a uracil at a position corresponding to position 1,056 according to SEQ ID NO:8, or the complement thereof, and when the subject is SREBF1 reference, the subject is also administered a therapeutic agent that treats or inhibits an increased lipid level in a standard dosage amount, and when the subject is heterozygous for the SREBF1 variant nucleic acid molecule, the subject is also administered a therapeutic agent that treats or inhibits an increased lipid level in a dosage amount that is the same as or lower than the standard dosage amount.

2. A method of treating a subject with a therapeutic agent that treats or inhibits an increased lipid level, wherein the subject is suffering from an increased lipid level, the method comprising the steps of:

determining whether the subject has an SREBF1 variant nucleic acid molecule encoding a human SREBF1 polypeptide by:

obtaining or having obtained a biological sample from the subject; and performing or having performed a genotyping assay on the biological sample to determine if the subject has a genotype comprising the SREBF1 variant nucleic acid molecule; and when the subject is SREBF1 reference, then administering or continuing to administer to the subject the therapeutic agent that treats or inhibits the increased lipid level in a standard dosage amount, and administering to the subject an SREBF1 inhibitor; and when the subject is heterozygous for the SREBF1 variant nucleic acid molecule, then administering or continuing to administer to the subject the therapeutic agent that treats or inhibits the increased lipid level in an amount that is the same as or lower than a standard dosage amount, and administering to the subject an SREBF1 inhibitor;

wherein the presence of a genotype having the SREBF1 variant nucleic acid molecule encoding the human SREBF1 polypeptide indicates the subject has a reduced risk of developing the increased lipid level;

wherein the increased lipid level is increased serum lipid level, increased total cholesterol, or increased LDL; and wherein the SREBF1 variant nucleic acid molecule is: i) a genomic nucleic acid molecule having a nucleotide sequence comprising a thymine at a position corresponding to position 17,922 according to SEQ ID NO:2, or the complement thereof, ii) an mRNA molecule having a nucleotide sequence comprising a uracil at a position corresponding to position 1,185 according to SEQ ID NO:6, or the complement thereof, iii) an mRNA molecule having a nucleotide sequence comprising a uracil at a position corresponding to position 1,260 according to SEQ ID NO:7, or the complement thereof, iv) an mRNA molecule having a nucleotide sequence comprising a uracil at a position corresponding to position 1,056 according to SEQ ID NO: 8, or the complement thereof, v) a cDNA molecule produced from an mRNA molecule in the sample, wherein the cDNA molecule has a nucleotide sequence comprising a thymine at a position corresponding to position 1,185 according to SEQ ID NO:12, or the complement thereof, vi) a cDNA molecule produced from an mRNA molecule in the sample, wherein the cDNA molecule has a nucleotide sequence comprising a thymine at a position corresponding to position 1,260 according to SEQ ID NO:13, or the complement thereof, and/or vii) a cDNA molecule produced from an mRNA molecule in the sample, wherein the cDNA molecule has a nucleotide sequence comprising a thymine at a position corresponding to position 1,056 according to SEQ ID NO: 14, or the complement thereof.

3. The method according to claim 1, wherein the subject is a human.

4. The method according to claim 1, wherein a subject having increased low density lipoprotein (LDL) is treated.

5. The method according to claim 1, wherein a subject having increased total cholesterol is treated.

6. The method according to claim 1, wherein a subject having increased low density lipoprotein (LDL) and increased total cholesterol is treated.

* * * * *